United States Patent [19]

Colerick Bird et al.

[11] Patent Number: 5,196,422
[45] Date of Patent: Mar. 23, 1993

[54] 5-LIPOXYGENASE INHIBITING THIAZOLES

[75] Inventors: Thomas G. Colerick Bird, Witry-les-Reims, France; Graham C. Crawley, Cheshire, United Kingdom; Martin P. Edwards, Cheshire, United Kingdom; Philip N. Edwards, Cheshire, United Kingdom; Jean-Marc M. M. Girodeau, Rilly la Montagne, France; John F. Kingston, Macclesfield, United Kingdom

[73] Assignees: ICI Pharma, Cergy Cedex, France; Imperial Chemical Industries plc, London, England

[21] Appl. No.: 791,375

[22] Filed: Nov. 14, 1991

Related U.S. Application Data

[62] Division of Ser. No. 378,163, Jul. 11, 1989, Pat. No. 5,089,513.

[30] Foreign Application Priority Data

Jul. 12, 1988 [FR] France .................. 88 401816

[51] Int. Cl.$^5$ ................ A61K 31/50; A61K 31/505; A61K 31/495; A61K 31/38
[52] U.S. Cl. ................... 514/252; 514/256; 514/269; 514/342; 514/365
[58] Field of Search ............ 514/252, 256, 269, 342, 514/365

[56] References Cited

U.S. PATENT DOCUMENTS 4,897,397  1/1990  Shih et al. .................. 514/365
4,962,117  10/1990  Young et al. ................ 514/342
5,089,495  2/1992  Crawley et al. .............. 514/342

FOREIGN PATENT DOCUMENTS 0200101  12/1986  European Pat. Off. .

*Primary Examiner*—Joseph Paul Brust
*Assistant Examiner*—MarySusan H. Gabilan
*Attorney, Agent, or Firm*—Cushman, Darby & Cushman

[57] ABSTRACT

The invention concerns a thiazole of the formula I,

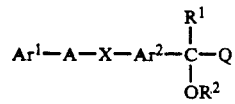

wherein
  $Ar^1$ is optionally substituted aryl of up to 10 carbon atoms;
  A is a direct link to X, or is (1–6C)alkylene, (3–6C)alkenylene, (3–6C)alkynylene or cyclo(3–6C)alkylene;
  X is oxy, thio, sulphinyl, sulphonyl or imino;
  $Ar^2$ is optionally substituted phenylene, or a 6-membered heterocyclene moiety containing up to three nitrogen atoms;
  $R^1$ is hydrogen, (1–6C)alkyl, (2–6C)alkenyl, (2–6C)alkynyl or substituted (1–4C)alkyl;
  $R^2$ is hydrogen, (1–6C)alkyl, (3–6C)alkenyl, (3–6C)alkynyl, substituted (1–4C)alkyl or (2–6C)alkanoyl;
  Q is optionally substituted thiazolyl;
or a pharmaceutically-acceptable salt thereof.

The invention also concerns processes for the manufacture of a thiazole of the formula I, or a pharmaceutically-acceptable salt thereof, and pharmaceutical compositions containing said thiazole.

5 Claims, No Drawings

5-LIPOXYGENASE INHIBITING THIAZOLES

This is a division of application Ser. No. 07/378,163, filed Jul. 11, 1989, now U.S. Pat. No. 5,089,513.

This invention concerns novel heterocyclic compounds and more particularly novel thiazoles which are inhibitors of the enzyme 5-lipoxygenase (hereinafter referred to as 5-LO). The invention also concerns processes for the manufacture of said thiazoles and novel pharmaceutical compositions containing said thiazoles. Also included in the invention is the use of said thiazoles in the treatment of various inflammatory and/or allergic diseases in which the direct or indirect products of 5-LO catalysed oxidation of arachidonic acid are involved, and the production of new medicaments for such use.

As stated above the thiazoles described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain thiazoles are effective as inhibitors of the enzyme 5-LO and thus of leukotriene biosyntheses. Thus, such compounds are of value as therapeutic agents in the treatment of, for example, allergic conditions, asthma, cardiovascular and cerebrovascular disorders, and/or inflammatory and arthritic conditions, mediated alone or in part by one or more leukotrienes.

According to the invention there is provided a thiazole of the formula I (set out hereinafter) wherein $Ar^1$ is aryl of up to 10 carbon atoms which may optionally bear one or more substituents selected from halogen, amino, hydroxy, cyano, formyl, carbamoyl, (1–6C)alkyl, (2–6C)alkenyl, (2–6C)alkynyl, (1–6C)alkoxy, (1–6C)alkylthio, (1–6C)alkysulphinyl, (1–6C)alkylsulphonyl, (1–6C)alkylamino, di-[(1–4C)alkyl]amino, (1–4C)alkoxycarbonyl, N-[(1–6C)alkyl]carbamoyl, N,N-di-[(1–4C)alkyl]carbamoyl, (2–6C)alkanoyl, (2–6C)alkanoylamino, (1–4C)alkylureido, hydroxy-(1–4C)alkyl and fluoro-(1–4C)alkyl; wherein A is a direct link to X, or is (1–6C)alkylene, (3–6C)alkenylene, (3–6C)alkynylene or cyclo(3–6C)alkylene; wherein X is oxy, thio, sulphinyl, sulphonyl or imino; wherein $Ar^2$ is phenylene which may optionally bear one or two substituents selected from halogen, hydroxy, amino, nitro, cyano, carbamoyl, (1–6C)alkyl, (1–6C)alkoxy, (3–4C)alkenyloxy, (1–6C)alkylthio, (1–6C)alkylsulphinyl, (1–6C)alkylsulphonyl, (1–6C)alkylamino, di-[(1–4C)alkyl]amino, (1–4C)alkoxycarbonyl, N-[(1–6C)alkyl]carbamoyl, N,N-di-[(1–4C)alkyl]carbamoyl, (2–6C)alkanoylamino, fluoro-(1–4C)alkoxy, hydroxy-(2–4C)alkoxy, (1–4C)alkoxy-(2–4C)alkoxy, amino-(2–4C)alkoxy, cyano-(1–4C)alkoxy, carbamoyl-(1–4C)alkoxy, (1–6C)alkylamino-(2–4C)alkoxy, di-[(1–4C)alkyl]amino-(2–4C)alkoxy, (1–4C)alkoxycarbonyl-(1–4C)alkoxy, N-[(1–6C)alkyl]carbamoyl-(1–4C)alkoxy, N,N-[di(1–4C)alkyl]carbamoyl-(1–4C)alkoxy, fluoro-(1–4C)alkyl, hydroxy-(1–4C)alkyl, amino-(1–4C)alkyl, cyano-(1–4C)alkyl, (1–4C)alkoxy-(1–4C)alkyl, (1–4C)alkylamino-(1–4C)alkyl, di-[(1–4C)alkyl]amino-(1–4C)alkyl, (2–6C)alkanoylamino-(1–4C)alkyl, (1–4C)alkoxycarbonyl-(1–4C)alkylamino, carbamoyl-(1–4C)alkylamino, cyano-(1–4C)alkylamino, hydroxy-(2–4C)alkylamino and (1–4C)alkylsulphonamido, or $Ar^2$ is a 6-membered heterocyclene moiety containing up to three nitrogen atoms which may optionally bear one or two substituents selected from halogeno, hydroxy, amino, cyano, (1–6C)alkyl, (1–6C)alkoxy, (1–6C)alkylamino and di-[(1–4C)alkyl]amino; wherein $R^1$ is hydrogen, (1–6C)alkyl, (2–6C)alkenyl, (2–6C)alkynyl, fluoro-(1–4C)alkyl, cyano-(1–4C)alkyl, hydroxy-(1–4C)alkyl, (1–4C)alkoxy-(1–4C)alkyl and (2–4C)alkanoyloxy-(1–4C)alkyl; wherein $R^2$ is hydrogen, (1–6C)alkyl, (3–6C)alkenyl, (3–6C)alkynyl, fluoro-(1–4C)alkyl, (1–4C)alkylthio-(1–4C)alkyl, cyano-(1–4C)alkyl, (1–4C)alkoxycarbonyl-(1–4C)alkyl, carboxy-(1–4C)alkyl, carbamoyl-(1–4C)alkyl or (2–6C)alkanoyl or $R^2$ is benzoyl which may optionally bear a substituent selected from halogeno, (1–6C)alkyl or (1–6C)alkoxy; and wherein Q is thiazolyl which may optionally bear one or two substituents selected from halogeno, amino, nitro, cyano, (1–6C)alkyl, (1–6C)alkoxy, (1–6C)alkylamino, di-[(1–4C)alkyl]amino, (1–4C)alkoxycarbonylamino, (2–6C)alkanoyl, (2–6C)alkanoylamino, (1–4C)alkoxycarbonylamino, fluoro-(1–4C)alkyl and hydroxy-(1–4C)alkyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for $Ar^1$ when it is aryl of up to 10 carbon atoms is, for example, phenyl or naphthyl, A suitable value for a halogeno substituent which may be present on Ar$^1$, Ar$^2$, R$^2$ or Q is, for example, fluoro, chloro, bromo or iodo.

A suitable value for a (1–6C)alkyl substituent which may be present on Ar$^1$, Ar$^2$, R$^2$ or Q is, for example, methyl, ethyl, propyl, isopropyl, butyl, isobutyl, sec-butyl, pentyl or hexyl.

A suitable value for a (2–6C)alkenyl substituent on Ar$^1$, is, for example, vinyl, allyl, 2-butenyl or 3-butenyl.

A suitable value for a (2–6C)alkynyl substituent on Ar$^1$ is, for example, ethynyl, 1-propynyl, 2-propynyl, 1-butynyl or 2-butynyl.

A suitable value for a (1–6C)alkoxy substituent which may be present on Ar$^1$, Ar$^2$, R$^2$ or Q is, for example, methoxy, ethoxy, propoxy, isopropoxy or butoxy.

Suitable values for substituents which may be present on Ar$^1$ or Ar$^2$ include, for example:

| | |
|---|---|
| for (1–6C)alkythio: | methylthio, ethylthio, propylthio, isopropylthio and butylthio; |
| for (1–6C)alkylsulphinyl: | methylsulphinyl, ethylsulphinyl, propylsulphinyl, isopropylsulphinyl and butylsulphinyl; |
| for (1–6C)alkylsulphonyl: | methylsulphonyl, ethylsulphonyl, propylsulphonyl, isopropylsulphonyl and butylsulphonyl; |
| for N-[(1–6C)alkyl]carbamoyl: | N-methylcarbamoyl, N-ethylcarbamoyl and N-propylcarbamoyl; |
| for N,N-di-[(1–4C)alkyl]-carbamoyl: | N,N-dimethylcarbamoyl and N,N-diethylcarbamoyl. |

A suitable value for a (2–6C)alkanoyl substituent which may be present on Ar$^1$ or Q is, for example, acetyl, propionyl or butyryl.

Suitable values for substituents which may be present on Ar$^1$, Ar$^2$ or Q include, for example:

| | |
|---|---|
| for (1–6C)alkylamino: | methylamino, ethylamino, propylamino and butylamino; |
| for di-[(1–4C)alkyl]amino: | dimethylamino, diethylamino and dipropylamino; |
| for (1–4C)alkoxycarbonyl: | methoxycarbonyl, ethoxycarbonyl and tert-butoxycarbonyl; |
| for (2–6C)alkanoylamino: | acetamido, propionamido, butyramido and hexanamido; |
| for hydroxy-(1–4C)alkyl: | hydroxymethyl, 1-hydroxyethyl, 2-hydroxyethyl, 1-hydroxypropyl, 2-hydroxypropyl and 3-hydroxypropyl; |
| for fluoro-(1–4C)alkyl: | fluoromethyl, difluormethyl, trifluoromethyl, 2-fluoroethyl, 2,2,2-trifluoroethyl and pentafluoroethyl. |

A suitable value for a (1–4C)alkylureido substituent which may be present on Ar$^1$ is, for example, a 3-(1–4C)alkylureido substituent such as 3-methylureido, 3-ethylureido or 3-propylureido.

A suitable value for the number of substituents which may be present on Ar$^1$ is, for example, one, two or three.

A suitable value for A when it is (1–6C)alkylene is, for example, methylene, ethylene, ethylidene, trimethylene, propylidene, tetramethylene or pentamethylene; when it is (3–6C)alkenylene is, for example, 1-propenylene, 2-methylprop-1-enylene, 3-methylprop-1-enylene, 1-butenylene or 2-butenylene; and when it is (3–6C)alkynylene is, for example, 1-propynylene, 3-methylprop-1-ynylene, 1-butynylene or 2-butynylene.

A suitable value for A when it is cyclo(3–6C)alkylene is, for example, cyclopropylidene, 1,2-cyclopropylene, cyclopentylidene, 1,2-cyclopentylene, cyclohexylidene or 1,4-cyclohexylene.

A suitable value for Ar$^2$ when it is phenylene is, for example, 1,3-phenylene or 1,4-phenylene.

A suitable value for Ar$^2$ when it is a 6-membered heterocyclene moiety containing up to three nitrogen atoms is, for example, pyridylene, pyrimidinylene, pyridazinylene, pyrazinylene or 1,3,5-triazinylene. Conveniently Ar$^2$ when it is a 6-membered heterocyclene moiety containing up to three nitrogen atoms is, for example, 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene.

Suitable values for substituents which may be present on Ar$^2$ include, for example:

| | |
|---|---|
| for (3–4C)alkenyloxy: | allyloxy, methylallyloxy, but-2-enyloxy and but-3-enyloxy; |
| for fluoro-(1–4C)alkoxy: | fluoromethoxy, difluoromethoxy and trifluoromethoxy; |
| for hydroxy-(2–4C)alkoxy: | 2-hydroxyethoxy and 3-hydroxypropoxy; |
| for (1–4C)alkoxy-(2–4C)alkoxy: | 2-methoxyethoxy, 3-methoxypropoxy and 2-ethoxyethoxy; |
| for amino-(2–4C)alkoxy: | 2-aminoethoxy and 3-aminopropoxy; |
| for cyano-(1–4C)alkoxy: | cyanomethoxy, 2-cyanoethoxy and 3-cyanopropoxy; |
| for carbamoyl-(1–4C)alkoxy; | carbamoylmethoxy, 2-carbamoylethoxy and 3-carbamoylpropoxy; |
| for [(1–6C)alkyl]amino-(2–4C)-alkoxy: | 2-methylaminoethoxy, 3-methylaminopropoxy and 2-ethylaminoethoxy; |
| for di-[(1–4C)alkyl]amino-(2–4C)-alkoxy: | 2-dimethylaminoethoxy, 3-dimethylaminopropoxy and 2-diethylaminoethoxy; |
| for (1–4C)alkoxycarbonyl-(1–4C)-alkoxy: | methoxycarbonylmethoxy, 2-methoxycarbonylethoxy, ethoxycarbonylmethoxy and 2-ethoxycarbonylethoxy; |
| for N-[(1–6C)alkyl]carbamoyl-(1–4C)alkoxy: | N-methylcarbamoylmethoxy, 2-(N-methylcarbamoyl)ethoxy, N-ethylcarbamoylmethoxy and 2-(N-ethylcarbamoyl)ethoxy; |
| for N,N-[di-(1–4C)alkyl]-carbamoyl-(1–4C)alkoxy: | N,N-dimethylcarbamoylmethoxy, 2-(N,N-dimethylcarbamoyl)-ethoxy, N,N-diethylcarbamoyl methoxy and 2-(N,N-diethyl carbamoyl)ethoxy; |
| for amino-(1–4C)alkyl: | aminomethyl, 2-aminoethyl and 3-aminopropyl; |
| for cyano-(1–4C)alkyl: | cyanomethyl, 2-cyanoethyl and 3-cyanopropyl; |
| for (1–4C)alkoxy-(1–4C)alkyl: | methoxymethyl, 2-methoxyethyl, 3-methoxypropyl, ethoxymethyl, 2-ethoxyethyl and 3-ethoxypropyl; |
| for (1–4C)alkylamino-(1–4C)alkyl: | methylaminomethyl, 2-methylaminoethyl, 3-methylaminopropyl, ethylaminomethyl, 2-ethylaminoethyl and 3-ethylaminopropyl; |
| for di-[(1–4C)alkyl]amino-(1–4C)-alkyl: | dimethylaminomethyl, 2-dimethylaminoethyl, 3-dimethylaminopropyl, diethylaminomethyl, 2-diethylaminoethyl and 3-diethylaminopropyl; |
| for (2–6C)alkanoylamino-(1–4C)-alkyl: | acetamidomethyl, 2-acetamidoethyl, 3-acetamidopropyl, propionamidomethyl, 2-propionamidoethyl and 3-propionamidopropyl; |
| for (1–4C)alkoxycarbonyl-(1–4C)-alkylamino: | methoxycarbonylmethylamino, ethoxycarbonylmethylamino, |

-continued

| | 2-methoxycarbonylethylamino and 2-ethoxycarbonylethylamino; |
|---|---|
| for carbamoyl-(1–4C)alkylamino: | carbamoylmethylamino, 2-carbamoylethylamino and 3-carbamoylpropylamino; |
| for cyano-(1–4C)alkylamino: | cyanomethylamino, 2-cyanoethylamino and 3-cyanopropylamino; |
| for hydroxy-(2–4C)alkylamino: | 2-hydroxyethylamino and 3-hydroxypropylamino; |
| for hydroxy-(2–4C)alkylamino: | 2-hydroxyethylamino and 3-hydroxypropylamino; |
| for (1–4C)alkylsulphonamido: | methylsulphonamido, ethylsulphonamido and propylsulphonamido. |

A suitable value for $R^1$ when it is (1–6C)alkyl is, for example, methyl, ethyl, propyl, butyl, pentyl or hexyl; when it is (2–6C)alkenyl is, for example, vinyl, allyl, 2-butenyl or 3-butenyl; when it is (2–6C)alkynyl is, for example, ethynyl, 1-propynyl, 2-propynyl, 1-butynyl or 2-butynyl; when it is fluoro-(1–4C)alkyl is, for example, fluoromethyl, difluoromethyl, trifluoromethyl, 2-fluoroethyl, 2,2,2-trifluoroethyl or pentafluoroethyl; when it is cyano-(1–4C)alkyl is, for example, cyanomethyl, 2-cyanoethyl or 3-cyanopropyl; when it is hydroxy-(1–4C)alkyl is, for example, hydroxymethyl, 2-hydroxyethyl or 3-hydroxypropyl; when it is (1–4C)alkoxy-(1–4C)alkyl is, for example, methoxymethyl, 2-methoxyethyl, 3-methoxypropyl, ethoxymethyl, 2-ethoxyethyl or 3-ethoxypropyl; and when it is (2–4C)alkanoyloxy-(1–4C)alkyl is, for example, acetoxymethyl, 2-acetoxyethyl, 3-acetoxypropyl, propionyloxymethyl, 2-propionyloxyethyl or 3-propionyloxypropyl.

A suitable value for $R^2$ when it is (1–6C)alkyl is, for example, methyl, ethyl, propyl, isopropyl, butyl, isobutyl, sec-butyl, pentyl or hexyl; when it is (3–6C)alkenyl is, for example allyl, 2-butenyl or 3-butenyl; when it is (3–6C)alkynyl is, for example 2-propynyl or 2-butynyl; and when it is (2–4C)alkanoyl is, for example, acetyl, propionyl or butyryl.

A suitable value for $R^2$ when it is (1–4C)alkoxycarbonyl-(1–4C)alkyl is, for example, methoxycarbonylmethyl, 2-methoxycarbonylethyl, ethoxycarbonylmethyl or 2-ethoxycarbonylethyl; when it is carboxy-(1–4C)alkyl is, for example, carboxymethyl, 2-carboxyethyl or 3-carboxypropyl; when it is carbamoyl-(1–4C)alkyl is, for example, carbamoylmethyl, 2-carbamoylethyl or 3-carbamoylpropyl; when it is cyano-(1–4C)alkyl is, for example, cyanomethyl, 2-cyanoethyl or 3-cyanopropyl; when it is fluoro-(1–4C)alkyl is, for example, trifluoromethyl, 2-fluoroethyl, 2,2-difluoroethyl, 2,2,2-trifluoroethyl or pentafluoroethyl; and when it is (1–4C)alkylthio-(1–4C)alkyl is, for example, methylthiomethyl, ethylthiomethyl, 2-methylthioethyl and 2-ethylthioethyl.

A suitable value for Q when it is thiazolyl is 2-, 4- or 5-thiazolyl.

A suitable value for (1–4C)alkoxycarbonylamino substituent which may be present on Q is, for example, methoxycarbonylamino, ethoxycarbonylamino and propoxycarbonylamino.

A suitable pharmaceutically-acceptable salt of a thiazole of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a thiazole of the invention which is sufficiently acidic (for example a thiazole of the invention which contains a carboxy group) is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, thiazoles of the formula I wherein:

(a) $Ar^1$ is phenyl, naphth-1-yl or naphth-2-yl which may optionally bear one, two or three substituents selected from fluoro, chloro, bromo, iodo, amino, hydroxy, cyano, formyl, carbamoyl, methyl, methoxy, methylthio, methylsulphinyl, methylsulphonyl, methoxycarbonyl, acetamido, 3-ethylureido, difluoromethyl and trifluoromethyl; and A, X, $Ar^2$, $R^1$, $R^2$ and Q have any of the meanings defined hereinbefore;

(b) $Ar^1$ is phenyl or naphth-2-yl which may optionally bear one, two or three substituents selected from fluoro, chloro, bromo, iodo, cyano, methyl, methoxy, methylthio, methylsulphinyl, methylsulphonyl, methoxycarbonyl and trifluoromethyl; and A, X, $Ar^2$, $R^1$, $R^2$ and Q have any of the meanings defined hereinbefore;

(c) A is a direct link to X, or is methylene, ethylene, trimethylene, 1-propenylene, 2-methylprop-1-enylene or 1-propynylene and $Ar^1$, X, $Ar^2$, $R^1$, $R^2$ and Q have any of the meanings defined hereinbefore;

(d) A is methylene, ethylene, trimethylene, 1-propenylene, 2-methylprop-1-enylene or 1-propynylene and $Ar^1$, X, $Ar^2$, $R^1$, $R^2$ and Q have any of the meanings defined hereinbefore;

(e) X is oxy, thio, sulphinyl or sulphonyl; and $Ar^1$, A, $Ar^2$, $R^1$, $R^2$ and Q have any of the meanings defined hereinbefore;

(f) X is oxy and $Ar^1$, A, $Ar^2$, $R^1$, $R^2$ and Q have any of the meanings defined hereinbefore;

(g) $Ar^2$ is 1,3-phenylene or 1,4-phenylene which may optionally bear one substituent selected from fluoro, chloro, hydroxy, amino, nitro, cyano, carbamoyl, methyl, ethyl, methoxy, allyloxy, methylthio, methylsulphinyl, methylsulphonyl, methylamino, dimethylamino, methoxycarbonyl, ethoxycarbonyl, tert-butoxycarbonyl, N-methylcarbamoyl, N,N-dimethylcarbamoyl, acetamido, cyanomethoxy, carbamoylmethoxy, methoxycarbonylmethoxy, ethoxycarbonylmethoxy, trifluoromethyl, methoxycarbonylmethylamino, ethoxycarbonylmethylamino, carbamoylmethylamino, cyanomethylamino, 2-hydroxyethylamino and methanesulphonamido; and $Ar^1$, A, X, $R^1$, $R^2$ and Q have any of the meanings defined hereinbefore;

(h) $Ar^2$ is 1,3-phenylene or 1,4-phenylene which may optionally bear one substituent selected from chloro, bromo, hydroxy, amino, nitro, methyl, ethyl, methoxy, methylthio, methylsulphinyl, methylsulphonyl, methylamino, dimethylamino, cyanomethoxy, carbamoylmethoxy, N-methylcarbamoylmethoxy and N,N-dimethylcarbamoylmethoxy; and $Ar^1$, A, X, $R^1$, $R^2$ and Q have any of the meanings defined hereinbefore;

(i) $Ar^2$ is 2,4-, 2,5-, 3,5- or 2,6-pyridylene or 4,6-pyrimidinylene; and $Ar^1$, A, X, $R^1$, $R^2$ and Q have any of the meanings defined hereinbefore;

(j) $Ar^2$ is 2,5-, 3,5- or 2,6-pyridylene or 4,6-pyrimidinylene which may optionally bear one substituent selected from chloro, methyl and methoxy; and $Ar^1$, A, X, $R^1$, $R^2$ and Q have any of the meanings defined hereinbefore;

(k) $R^1$ is hydrogen, methyl, ethyl, propyl, vinyl, ethynyl, 1-propynyl, 2-propynyl, trifluoromethyl, cyanomethyl, hydroxymethyl, methoxymethyl or acetoxymethyl; and $Ar^1$, A, X, $Ar^2$, $R^2$ and Q have any of the meanings defined hereinbefore;

(l) $R^1$ is hydrogen, methyl, ethyl, propyl, vinyl, ethynyl, trifluoromethyl, hydroxymethyl, methoxymethyl or acetoxymethyl; and $Ar^1$, A, X, $Ar^2$, $R^2$ and Q have any of the meanings defined hereinbefore;

(m) $R^2$ is hydrogen, methyl, ethyl, propyl, allyl, 2-butenyl, 2-propynyl, 2-butynyl, 2-fluoroethyl, 2,2-difluoroethyl, 2,2,2-trifluoroethyl, methylthiomethyl, cyanomethyl, 2-cyanoethyl, methoxycarbonylmethyl, ethoxycarbonylmethyl, carboxymethyl, carbamoylmethyl or acetyl; and $Ar^1$, A, X, $Ar^2$, $R^1$ and Q have any of the meanings defined hereinbefore;

(n) $R^2$ is hydrogen or methyl; and $Ar^1$, A, X, $Ar^2$, $R^1$ and Q have any of the meanings defined hereinbefore; or (o) Q is 2-, 4- or 5-thiazolyl which may optionally bear one or two substituents selected from chloro, methyl, methoxycarbonyl, acetyl and ethoxycarbonylamino; and $Ar^1$, A, X, $Ar^2$, $R^1$ and $R^2$ have any of the meanings defined hereinbefore;

(p) Q is 2- or 4-thiazolyl; and $Ar^1$, A, X, $Ar^2$, $R^1$ and $R^2$ have any of the meanings defined hereinbefore;

or a pharmaceutically-acceptable salt thereof.

A particular compound of the invention comprises a thiazole of the formula I wherein $Ar^1$ is phenyl, naphth-1-yl or naphth-2-yl which may optionally bear one, two or three substituents selected from fluoro, chloro, amino, hydroxy, cyano, formyl, carbamoyl, methyl, methoxy, methylthio, methylsulphinyl, methylsulphonyl, methoxycarbonyl, acetamido, difluoromethyl and trifluoromethyl;

A is a direct link to X, or is methylene, 1-propenylene, 2-methylprop-1-enylene or 1-propynylene;

X is oxy, thio, sulphinyl or sulphonyl;

$Ar^2$ is 1,3-phenylene or 1,4-phenylene which may optionally bear one substituent selected from fluoro, hydroxy, amino, nitro, cyano, carbamoyl, methyl, methoxy, allyloxy, methylamino, dimethylamino, tert-butoxycarbonyl, acetamido, cyanomethoxy, carbamoylmethoxy, ethoxycarbonylmethoxy, trifluoromethyl, carbamoylmethylamino, cyanomethylamino, 2-hydroxyethylamino and methanesulphonamido, or $Ar^2$ is 2,4-, 2,5- or 3,5-pyridylene, or 4,6-pyrimidinylene;

$R^1$ is methyl, ethyl, propyl, vinyl, ethynyl, 2-propynyl, trifluoromethyl, cyanomethyl, hydroxymethyl, methoxymethyl or acetoxymethyl;

$R^2$ is methyl, ethyl, allyl, 2-propynyl, 2-fluoroethyl, 2,2-difluoroethyl, methylthiomethyl or cyanomethyl; and Q is 2-, 4- or 5-thiazolyl which may optionally bear one substituent selected from chloro, methyl and methoxycarbonyl;

or a pharmaceutically-acceptable salt thereof.

A preferred compound of the invention comprises a thiazole of the formula I wherein $Ar^1$ is phenyl, naphth-1-yl or naphth-2-yl which may optionally bear one or two substituents selected from fluoro, chloro, cyano, methyl, methoxy, methylthio, methoxycarbonyl, difluoromethyl and trifluoromethyl;

A is a direct link to X, or is methylene, 1-propenylene, 2-methylprop-1-enylene or 1-propynylene;

X is oxy, thio, sulphinyl or sulphonyl;

$Ar^2$ is 1,3-phenylene or 1,4-phenylene which may optionally bear one subtituent selected from fluoro, hydroxy, amino, nitro, methyl, methoxy, methylamino, dimethylamino, cyanomethoxy and trifluoromethyl, or $Ar^2$ is 2,5- or 3,5-pyridylene;

$R^1$ is methyl, ethyl, vinyl, 2-propynyl or cyanomethyl;

$R^2$ is methyl, ethyl, allyl, 2-propynyl or cyanomethyl; and

Q is 2- or 4-thiazolyl;

or a pharmaceutically-acceptable salt thereof.

A further preferred compound of the invention comprises a thiazole of the formula I wherein $Ar^1$ is phenyl, naphth-2-yl, 3,4-dichlorophenyl, 3-iodophenyl, 3-cyanophenyl, 3,4-dimethoxyphenyl, 3,4,5-trimethoxyphenyl, 4-methylthiophenyl, 4-methylsulphinylphenyl, 3-trifluoromethylphenyl, 6-fluoronaphth-2-yl or 5-cyanonaphth-2-yl;

A is methylene, 1-propenylene, 2-methylprop-1-enylene or 1-propynylene;

X is oxy;

$Ar^2$ is 1,3-phenylene, 5-hydroxy-1,3-phenylene, 5-amino-1,3-phenylene, 5-nitro-1,3-phenylene, 4-methyl-1,3-phenylene, 5-methoxy-1,3-phenylene, 5-cyanomethoxy-1,3-phenylene, 5-carbamoylmethoxy-1,3-phenylene, 2,5-pyridylene, 3,5-pyridylene, 2,6-pyridylene or 4,6-pyrimidinylene;

$R^1$ is hydrogen, methyl, ethyl, propyl, vinyl, trifluoromethyl, hydroxymethyl, methoxymethyl or acetoxymethyl;

$R^2$ is hydrogen or methyl; and

Q is 2-thiazolyl or 4-thiazolyl;

or a pharmaceutically-acceptable salt thereof.

An especially preferred compound of the invention comprises a thiazole of the formula I wherein $Ar^1$ is phenyl, naphth-1-yl, naphth-2-yl, 2-fluorophenyl, 3-fluorophenyl, 4-fluorophenyl, 3,4-difluorophenyl, 6-fluoronaphth-2-yl, 7-fluoronaphth-2-yl, 2-chlorophenyl, 3-chlorophenyl, 2-tolyl, 6-methylnaphth-2-yl, 2-methoxyphenyl, 3-methoxyphenyl, 4-methoxyphenyl, 2-methylthiophenyl, 3-methoxycarbonylphenyl, 2-trifluoromethylphenyl, 3-trifluoromethylphenyl or 7-difluoromethylnaphth-2-yl;

A is a direct link to X, or is methylene, 1-propenylene or 1-propynylene;

X is oxy or thio;

$Ar^2$ is 1,3-phenylene, 5-fluoro-1,3-phenylene, 5-methoxy-1,3-phenylene, 2-methoxy-1,4-phenylene, 5-cyanomethoxy-1,3-phenylene, 5-trifluoromethyl-1,3-phenylene or 3,5-pyridylene;

$R^1$ is methyl or ethyl;

$R^2$ is methyl, ethyl, allyl, 2-propynyl or cyanomethyl; and

Q is 2-thiazolyl;

or a pharmaceutically-acceptable salt thereof.

A further especially preferred compound of the invention comprises a thiazole of the formula I wherein Ar¹ is phenyl, naphth-1-yl, 2-fluorophenyl, 3-fluorophenyl, 4-fluorophenyl, 3,4-difluorophenyl, 2-chlorophenyl, 3-chlorophenyl, 2-tolyl, 2-methoxyphenyl, 3-methoxyphenyl, 4-methoxyphenyl, 3-methoxycarbonylphenyl, 2-trifluoromethylphenyl or 3-trifluoromethylphenyl;

A is 1-propynylene;

X is oxy;

Ar² is 1,3-phenylene, 5-fluoro-1,3-phenylene, 5-methoxy-1,3-phenylene, 2-methoxy-1,4-phenylene or 5-trifluoromethyl-1,3-phenylene;

R¹ is methyl or ethyl;

R² is methyl; and

Q is 2-thiazolyl;

or a pharmaceutically-acceptable salt thereof.

A further especially preferred compound of the invention comprises a thiazole of the formula I wherein Ar¹ is phenyl or naphth-2-yl;

A is methylene or 1-propynylene;

X is oxy;

Ar² is 1,3-phenylene, 5-methoxy-1,3-phenylene or 3,5-pyridylene;

R¹ is ethyl; R² is methyl and Q is 2-thiazolyl;

or a pharmaceutically-acceptable salt thereof.

Specific especially preferred compounds of the invention include, for example, the following thiazoles of the formula I, or a pharmaceutically-acceptable salt thereof:

2-[1-methoxy-1-[3-(naphth-2

2-[1-methoxy-1-[3-(naphth-2-ylmethoxy)phenyl]-propyl]thiazole;

2-[1-methoxy-1-[3-methoxy-5-(naphth-2-ylmethoxy)-phenyl]propyl]-thiazole;

2-[1-methoxy-1-[5-(naphth-2-ylmethoxy)pyrid-3-yl]propyl]thiazole;

2-[1-methoxy-1-[3-(3-phenylprop-2-ynyloxy)phenyl]-propyl]thiazole;

2-[1-methoxy-1-(3-(6-methylnaphth-2-ylmethoxy)-phenyl)propyl]thiazole;

2-[1-methoxy-1-(5-methoxy-3-(naphth-2-ylmethoxy)-phenyl)propyl]thiazole;

2-[1-methoxy-1-(3-(naphth-2-ylmethoxy)-5-trifluoromethylphenyl)propyl]thiazole;

2-[1-ethoxy-1-(3-(naphth-2-ylmethoxy)-5-trifluoromethylphenyl)propyl]thiazole;

2-[1-allyloxy-1-(5-methoxy-3-(naphth-2-ylmethoxy)-phenyl)propyl]thiazole;

2-[1-(5-methoxy-3-(naphth-2-ylmethoxy)phenyl)-1-(propy-2-ynyloxy)propyl]thiazole;

2-[1-methoxy-1-[3-methoxy-(4-(3-phenylprop-2-ynyloxy)phenyl]propyl]thiazole;

2-[1-[3-(3-(3-chlorophenyl)prop-2-ynyloxy)phenyl]-1-methoxypropyl]thiazole;

2-[1-[3-(3-(2-fluorophenyl)prop-2-ynyloxy)phenyl]-1-methoxypropyl]thiazole;

2-[1-[3-(3-(3-fluorophenyl)prop-2-ynyloxy)phenyl]-1-methoxypropyl]thiazole;

2-[1-[3-(3-(4-fluorophenyl)prop-2-ynyloxy)phenyl]-1-methoxypropyl]thiazole;

2-[1-methoxy-1-[3-(3-(naphth-1-yl)prop-2-ynyloxy)-phenyl]propyl]thiazole;

2-[1-cyanomethoxy-1-(5-methoxy-3-(naphth-2-ylmethoxy)phenyl)propyl]thiazole; and 2-[1-methoxy-1-(3-(naphth-2-ylthio)phenyl)propyl]-thiazole.

A compound of the invention comprising a thiazole of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, Ar¹, A, X, Ar², R¹, R² and Q have any of the meanings defined hereinbefore.

(a) The alkylation, in the presence of a suitable base, of a compound of the formula II with a compound of the formula Ar¹—A—Z wherein Z is a displaceable group; provided that, when there is an amino, alkylamino, hydroxy or carboxy group in Ar¹, Ar², R¹ or Q, any amino, alkylamino or carboxy group is protected by a conventional protecting group and any hydroxy group may be protected by a conventional protecting group or alternatively any hydroxy group need not be protected; whereafter any undesired protecting group in Ar¹, Ar², R¹ or Q is removed by conventional means.

A suitable displaceable group Z is, for example, a halogeno, sulphonyloxy or hydroxy group, for example a chloro, bromo, iodo, methanesulphonyloxy, toluene-p-sulphonyloxy or hydroxy group.

A suitable reagent for the alkylation reaction when Z is a halogeno or sulphonyloxy group is, for example, a suitable base, for example, an alkali or alkaline earth metal carbonate, hydroxide or hydride, for example sodium carbonate, potassium carbonate, sodium hydroxide, potassium hydroxide, sodium hydride or potassium hyride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

A suitable reagent for the alkylation reaction when Z is a hydroxy group is, for example, the reagent obtained when a compound of the formula Ar¹—A—OH is reacted with a di-(1–4C)alkyl azodicarboxylate in the presence of a triarylphosphine, for example with diethyl azodicarboxylate in the presence of triphenylphosphine. The alkylation reaction is preferably performed in a suitable inert solvent or diluent, for example acetone, 1,2-dimethoxyethane or tetrahydrofuran, and at a temperature in the range, for example, 10° to 80° C., conveniently at or near ambient temperature.

A suitable protecting group for an amino or alkylamino group is, for example, an acyl group for example a (1–4C)alkanoyl group (especially acetyl), a (1–4C)alkoxycarbonyl group (especially methoxycarbonyl, ethoxycarbonyl or t-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulphuric or phosphoric acid and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a (1–4C)alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal.

A suitable protecting group for a hydroxy group is, for example, an acyl group, for example a (1–4C)alkanoyl group (especially acetyl), an aroyl group (especially benzoyl) or an arylmethyl group (especially benzyl). The deprotection conditions for the above protecting group will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting material of the formula II may be obtained, for example, by deprotecting a protected thiazole of the formula III wherein $R^3$ is a protecting group and X, $Ar^2$, $R^1$, $R^2$ and Q have the meanings defined hereinbefore.

A suitable protecting group $R^3$ is, for example, an arylmethyl group (especially benzyl), a tri-(1–4C)alkylsilyl group (especially trimethylsilyl or t-butyldimethylsilyl), an aryldi-(1–4C)alkylsilyl group (especially dimethylphenylsilyl), a (1–4C)alkyl group (especially methyl), a (1–4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryl dialkylsilyl group such as a t-butyldimethylsilyl or a dimethylphenylsilyl group may be removed, for example, by treatment with a suitable acid such as hydrochloric, sulphuric, phosphoric or trifluoroacetic acid or with an alkali metal or ammonium fluoride such as sodium fluoride or, preferably, tetrabutylammonium fluoride. Alternatively an alkyl group may be removed, for example, by treatment with an alkali metal (1–4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1–4C)alkoxymethyl group or tetrahydropyranyl group may be removed, for example, by treatment with a suitable acid such as hydrochloric or trifluoroacetic acid.

The protecting group $R^3$ may be, for example, a tri-(1–4C)alkylsilyl group which can be removed while the protecting group for any amino, alkylamino, carboxy or hydroxy group in $Ar^2$, $R^1$ or Q is retained.

The protected starting material of the formula III may be obtained by standard procedures of organic chemistry. The following process variants are described for the purposes of illustration only and as examples of the many routes available to the man skilled in the art of organic chemistry for the preparation of the starting material of formula III. Further process variants are provided within the Examples provided hereinafter to illustrate further the many options available to the man skilled in the art. Thus, for example, an alcohol of the formula $R^3—X—Ar^2—CH(OH)—Q$, wherein $R^3$ is a protecting group as defined hereinbefore, may be obtained by the reaction of an aldehyde of the formula $R^3—X—Ar^2—CHO$ with an organometallic compound of the formula Q—M, wherein Q has the meaning defined hereinbefore and M is a metallic group, for example lithium, and provided that any amino, alkylamino, carboxy or hydroxy group in $Ar^2$ or Q is protected by a conventional protecting group. The reaction may be carried out in, for example, a suitable solvent or diluent such as an ether (for example tetrahydrofuran, t-butylmethylether or diethyl ether) at a temperature in the range, for example, $-100°$ to $50°$ C. (especially $-80°$ to $30°$ C.).

The secondary alcohol of the formula $R^3—X—Ar^2—CH(OH)—Q$ may be oxidised to give a ketone of the formula $R^3—X—Ar^2—CO—Q$. A particular suitable oxidising agent is, for example, any agent known in the art for the oxidation of a secondary alcohol to a ketone, for example, manganese dioxide, chromium trioxide pyridine complex, 2,3-dichloro-5,6-dicyano-1,4-benzoquinone (hereinafter DDQ), a mixture of dimethylsulphoxide, oxalyl chloride and triethylamine, a mixture of acetic anhydride and dimethylsulphoxide or a mixture of dimethylsulphoxide and a dialkylcarbodiimide, for example N,N'-dicyclohexylcarbodiimide or N-ethyl-N'-(3-dimethylaminopropyl)carbodiimide.

A tertiary alcohol of the formula IV, wherein $R^3$ has the meaning defined hereinbefore, may be obtained by the reaction of the ketone $R^3—X—Ar^2—CO—Q$ with an organometallic compound of the formula $R^1—M—Z$, wherein M is a metallic group, for example magnesium, and Z is a halogeno group, for example chloro, bromo or iodo, and provided that any amino, alkylamino, carboxy or hydroxy group in $Ar^2$, $R^1$ or Q is protected by a conventional protecting group. The reaction may be carried out in a suitable solvent or diluent such as an ether (for example tetrahydrofuran, t-butyl methyl ether or diethyl ether) at a temperature in the range, for example, $-30°$ to $100°$ C. (especially ambient temperature to $80°$ C.).

It will be appreciated that the tertiary alcohol of the formula IV may be obtained from the aldehyde of the formula $R^3—X—Ar^2—CHO$ by reversing the order of introduction of the groups Q and $R^1$. Thus the aldehyde of the formula $R^3—X—Ar^2—CHO$ may be treated initially with the organometallic compound of the formula $R^1—M—Z$, the product so obtained may be oxidised using a suitable oxidising agent as described above and the resultant ketone may be treated with the organometallic compound Q—M to give the compound of the formula IV, and provided that any amino, alkylamino, carboxy or hydroxy group in $Ar^2$, $R^1$ or Q is protected by a conventional protecting group.

The protected thiazole of the formula III, wherein $R^3$ has the meaning defined hereinbefore, may be obtained by the alkylation of the tertiary alcohol of the formula IV with an alkylating agent of the formula $R^2—Z$, wherein Z is a displaceable group as defined hereinbefore other than hydroxy, in the presence of a suitable base as defined hereinbefore, and provided that any amino, alkylamino, carboxy or hydroxy group in $Ar^2$, $R^1$ or Q is protected by a conventional protecting group.

Alternatively the tertiary alcohol starting material of the formula IV may be obtained by the reaction of a compound of the formula $R^3$—X—$Ar^2$—Z, wherein $R^3$ and $Ar^2$ have the meanings defined hereinbefore and Z is a halogeno group as defined hereinbefore and provided that any amino, alkylamino or hydroxy group in $Ar^2$ is protected with a conventional protecting group, with either an organometallic compound of the formula $R^5$—M, wherein $R^5$ is a (1-6C)alkyl group such as butyl and M is a metallic group, for example lithium, to give an organometallic compound of the formula $R^3$—X—$Ar^2$—M, or with a metal such as magnesium to given an organometallic compound of the formula $R^3$—X—$Ar^2$—M—Z; whereafter either of these organometallic compounds may be reacted with a ketone of the formula $R^1$—CO—Q, wherein $R^1$ and Q have the meanings defined hereinbefore, and provided that any amino, alkylamino, carboxy or hydroxy group in $R^1$ or Q is protected by a conventional protecting group.

Alternatively the ketone of the formula $R^4$—X—Ar$^2$—CO—Q described hereinbefore may be obtained by the reaction of the nitrile of the formula $R^3$—X—Ar—CN with an organometallic compound of the formula Q—M using the conditions defined hereinbefore for the corresponding reaction of the aldehyde of the formula $R^3$—X—$Ar^2$—CHO.

(b) The alkylation, in the presence of a suitable base as defined hereinbefore, of a compound of the formula V with a compound of the formula $R^2$—Z, wherein $R^2$ and Z have the meanings defined hereinbefore, provided that, when there is an amino, imino, alkylamino, hydroxy or carboxy group in $Ar^1$, X, $Ar^2$, $R^1$ or Q, any amino, imino, alkylamino, hydroxy or carboxy group is protected by a conventional protecting group; whereafter any undesired protecting group in $Ar^1$, X, $Ar^2$, $R^1$ or Q is removed by conventional means.

A suitable protecting group for an imino group is, for example, any one of the protecting group defined hereinbefore as a suitable protecting group for an amino or alkylamino group.

The following process variants are described for the purposes of illustration only and as examples of the many routes available to the man skilled in the art of organic chemistry for the preparation of the starting material of formula V. Further purposes variants are provided within the Examples provided hereinafter to illustrate further the many options available to the man skilled in the art.

The tertiary alcohol starting material of the formula V may be obtained, for example, by the reaction of an aldehyde of the formula $Ar^1$—A—X—$Ar^2$—CHO with an organometallic compound of the formula Q—M, having the meaning defined hereinbefore and using the conditions defined hereinbefore, to give a secondary alcohol of the formula $Ar^1$—A—X—$Ar^2$—CH(OH)—Q and provided that any amino, imino, alkylamino, carboxy or hydroxy group in $Ar^1$, X, $Ar^2$ or Q is protected by a conventional protecting group. The product so obtained may be oxidised using a suitable oxidising agent, as defined hereinbefore, to give a ketone of the formula $Ar^1$—A—X—$Ar^2$—CO—Q, which in turn may be treated with an organometallic compound of the formula $R^1$—M—Z, having the meaning defined hereinbefore and using the conditions defined hereinbefore, to give the required tertiary alcohol starting material of the formula V.

It will be appreciated that the tertiary alcohol of the formula V may be obtained from the aldehyde of the formula $Ar^1$—A—X—$Ar^2$—CHO by reversing the order of the introduction of the groups Q and $R^1$, i.e. by reaction of the aldehyde of the formula $Ar^1$—A—X—$Ar^2$—CHO with the organometallic compound of the formula $R^1$—M—Z, oxidation of the secondary alcohol to a ketone of the formula $Ar^1$—A—X—$Ar^2$—CO—$R^1$ and reaction of said ketone with the organometallic compound of the formula Q—M, and provided that any amino, imino, alkylamino, carboxy or hydroxy group in Ar, X, $Ar^2$, $R^1$ or Q is protected by a conventional protecting group.

Alternatively the ketone intermediate of the formula $Ar^1$—A—X—$Ar^2$—CO—$R^1$ may be obtained, for example, by the alkylation, in the presence of a suitable base as defined hereinbefore, of a ketone of the formula H—X—$Ar^2$—CO—$R^1$ with a compound of the formula $Ar^1$—A—Z, wherein Z is a displaceable group as defined hereinbefore, and provided that any amino, alkylamino, carboxy or hydroxy group in $Ar^1$ or $Ar^2$ is protected by a conventional protecting group.

The aldehyde starting material of the formula $Ar^1$—A—X—$Ar^2$—CHO may be obtained, for example, by the alkylation, in the presence of a suitable base as defined hereinbefore, of an aldehyde of the formula H—X—$Ar^2$—CHO with a compound of the formula $Ar^1$—A—Z, wherein Z is a displaceable group, as defined hereinbefore, and provided that any amino, alkylamino, carboxy or hydroxy group in $Ar^1$ or $Ar^2$ is protected by a conventional protecting group.

Alternatively the tertiary alcohol starting material of the formula V may be obtained, for example, by the reaction of an ester of the formula $Ar^1$—A—X—$Ar^2$—$CO_2R^4$, wherein $R^4$ is a (1-4C)alkyl group such as methyl or ethyl, with an organometallic compound of the formula Q—M, having the meaning defined hereinbefore and using the conditions defined hereinbefore for the corresponding reaction of the aldehyde of the formula $R^3$—X—$Ar^2$—CHO, and provided that any amino, imino, alkylamino, carboxy or hydroxy group in $Ar^1$, X, $Ar^2$ or Q is protected by a conventional protecting group, to give a ketone of the formula $Ar^1$—A—X—$Ar^2$—CO—Q.

The product so obtained may be treated with an organometallic compound of the formula $R^1$—M—Z, having the meaning defined hereinbefore and using the conditions defined hereinbefore, to give the required tertiary alcohol starting material of the formula V.

It will be appreciated that the tertiary alcohol of the formula V may be obtained from the ester of the formula $Ar^1$—A—X—$Ar^2$—$CO_2R^4$ by reversing the order of the introduction of the groups Q and $R^1$, i.e. by reaction of the ester of the formula $Ar^1$—A—X—$Ar^2$—$CO_2R^4$ with the organometallic compound of the formula $R^1$—M—Z, to give a ketone of the formula $Ar^1$—A—X—$Ar^2$—CO—$R^1$ and reaction of said ketone with the organometallic compound of the formula Q—M, and provided that any amino, imino, alkylamino, carboxy or hydroxy group in $Ar^1$, X, $Ar^2$, $R^1$ or Q is protected by a conventional protecting group.

The ester starting material of the formula $Ar^1$—A—X—$Ar^2$—$CO_2R^4$ may be obtained, for example, by the alkylation, in the presence of a suitable base as defined hereinbefore, of an ester of the formula H—X—$Ar^2$—$CO_2R^4$, wherein $R^4$ has the meaning defined hereinbefore, with a compound of the formula $Ar^1$—A—Z, wherein Z is a displaceable group as defined hereinbefore, and provided that any amino, alkylamino, carboxy or hydroxy group in Ar$^1$ or Ar$^2$ is protected by a conventional protecting group.

Alternatively the tertiary alcohol starting material of the formula V may be obtained, for example, by the alkylation, in the presence of a suitable base, of a compound of the formula Ar$^1$—A—X—H, wherein Ar$^1$, A and X have the meanings defined hereinbefore, with a compound of the formula Z—Ar$^2$—Z, wherein Z is a displaceable group as defined hereinbefore, and provided that any amino, alkylamino, carboxy or hydroxy group in Ar$^1$ or Ar$^2$ is protected by a conventional protecting group, to give a compound of the formula Ar$^1$—A—X—Ar$^2$—Z. The product so obtained may be treated with an organometallic compound of the formula R$^5$—M, wherein R$^5$ is a (1-6C)alkyl group such as butyl and M is a metallic group, for example lithium, to give an organometallic compound of the formula Ar$^1$—A—X—Ar$^2$—M which may be reacted with a ketone of the formula Q.CO.R$^1$, provided that any amino, alkylamino or hydroxy group in Q or R$^1$ is protected by a conventional protecting group, to give the required tertiary alcohol starting material of the formula V.

(c) For the production of those compounds of the formula I wherein A is a (3-6C)alkynylene group, the coupling, in the presence of a suitable organometallic catalyst, of a compound of the formula Ar$^1$—Z wherein Ar$^1$ has the meaning defined hereinbefore and Z is a halogeno group such as iodo, with an ethynyl compound of the formula VI, wherein A$^1$ is (1-4C)alkylene and X, Ar$^2$, R$^1$, R$^2$ and Q have the meanings defined hereinbefore.

A suitable organometallic catalyst is, for example, any agent known in the art for such a coupling reaction. Thus, for example, a suitable reagent is formed when, for example, bis(triphenylphosphine)palladium chloride, and a copper halide, for example cuprous iodide, are mixed. The coupling is generally carried out in a suitable inert solvent or diluent, for example acetonitrile, 1,2-dimethoxyethane or tetrahydrofuran, at a temperature in the range, for example, 10° to 80° C., conveniently at or near 70° C., and in the presence of a suitable base such as, for example, a tri-(1-4C)alkylamine such as triethylamine.

The ethynyl compound of the formula VI, used as a starting material, may be obtained, for example, by the alkylation, in the presence of a suitable base, of a compound of the formula II, wherein X, Ar$^2$, R$^1$, R$^2$ and Q have the meanings defined hereinbefore, with an alkylating agent of the formula H—C≡C—A$^1$—Z, wherein A$^1$ has the meaning defined hereinbefore and Z is a halogeno group, and provided that any amino, alkylamino, carboxy or hydroxy group in Ar$^2$, R$^1$, R$^2$ or Q is protected by a convention protecting group.

(d) For the production of those compounds of the formula I wherein Ar$^1$ or Ar$^2$ bears an alkylsulphinyl or alkylsulphonyl substituent or X is a sulphinyl or sulphonyl group, the oxidation of a compound of the formula I wherein Ar$^1$ or Ar$^2$ bears an alkylthio substituent or wherein X is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or t-butyl methyl ether and at a temperature, for example, at or near ambient temperature, that is in the range 15° to 35° C. When a compound wherein X is sulphinyl and/or Ar$^1$ and/or Ar$^2$ bears an alkylsulphinyl substituent a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein Ar$^1$, Ar$^2$ or Q bears an alkanoylamino or alkanoylaminoalkyl substituent, the acylation of a compound of the formula I wherein Ar$^1$, Ar$^2$ or Q bears an amino or aminoalkyl substituent.

A suitable acylating agent is, for example, any agent known in the art for the acylation of amino to acylamino or of aminoalkyl to acylaminoalkyl, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or t-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein R$^2$ is alkanoyl or benzoyl optionally bearing a substituent as defined hereinbefore, the acylation of a compound of the formula I wherein R$^2$ is hydrogen. For the production of those compounds of the formula I wherein R$^2$ is alkanoyl the acylation reaction may be carried out using, for example, a suitable acylating agent as defined hereinbefore. For the production of those compounds of the formula I wherein R$^2$ is benzoyl optionally bearing a substituent the acylation may be carried out using, for example, a benzoyl halide, for example a benzoyl chloride or bromide, in the presence of a suitable base as defined hereinbefore.

(g) For the production of those compounds of the formula I wherein Ar$^1$ or Ar$^2$ bears an alkenyl substituent, A is alkenylene or R$^1$ is alkenyl, the reduction of the corresponding compound wherein Ar$^1$ or Ar$^2$ bears an alkynyl substituent, A is alkynylene or R$^1$ is alkynyl. In general conditions which are standard in the art for the reduction of an alkynyl or alkynylene group are used. Thus, for example, the reduction may be carried out by the hydrogenation of a solution of the alkynyl or alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate.

Preferably a palladium-on-barium sulphate catalyst is used to substantially prevent over-reduction of the alkynyl or alkynylene group to an alkyl or alkylene group respectively. The reaction is generally carried out at a temperature at or near ambient temperature, that is in the range 15° to 35° C.

Alternatively the reduction may be carried out by treating a solution of the alkynyl or alkynylene compound in an inert solvent or diluent with a suitable mixture such as a 1:1 mixture of an organometallic hydride, for example a di-(1-6C)alkylaluminium hydride such as diisobutylaluminium hydride, and an alkyl metal, for example a (1-6C)alkyl lithium such as methyl lithium. A suitable inert solvent or diluent is, for example, tetrahydrofuran, diethyl ether or t-butyl methyl ether and, in general, the reaction is carried out at a temperature, for example, in the range −25° C. to ambient temperature (especially −10° to 10° C.).

(h) For the production of those compounds of the formula I wherein $Ar^2$ bears an alkoxy or substituted alkoxy substituent, or an alkylamino or substituted alkylamino substituent, the alkylation of a compound of the formula I wherein $Ar^2$ bears a hydroxy or amino substituent.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-6C)alkyl chloride, bromide or iodide or a substituted (1-4C)alkyl chloride, bromide or iodide, in the presence of a suitable base. A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(i) For the production of those compounds of the formula I wherein $Ar^1$, $Ar^2$ or Q bears an amino substituent, the reduction of a compound of the formula I wherein $Ar^1$, $Ar^2$ or Q bears a nitro substituent.

A suitable reducing agent is, for example, any agent known in the art for the reduction of a nitro group to an amino group. Thus, for example, the reduction may be carried out by the hydrogenation of a solution of the nitro compound in an inert solvent or diluent in the presence of a suitable metal catalyst, for example finely divided platinum metal (obtained by the reduction of platinum oxide in situ). A suitable inert solvent or diluent is, for example, an alcohol, for example methanol, ethanol or isopropanol, or an ether, for example tetrahydrofuran.

A further suitable reducing agent is, for example, an activated metal such as activated iron produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example, 50° to 150° C., conveniently at or near 70° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae II, III, IV and V and these are provided as a further feature of the invention.

As stated previously, the thiazoles of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512-11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, *Brit. J. Pharmacol.* 1985, 84, 34P) which involves the use of a protein-$LTB_4$ conjugate produced using the procedure of Young et alia (*Prostaglandins*, 1983, 26(4),605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TXB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $T \times B_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319-2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431-438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a β-adrenergic blocking agent (propranolol) and a cyclooxygenase inhibitor (indomethacin), using the procedure of W. H. Anderson et alia (*British J Pharmacology*, 1983, 78(1), 67-574). This test provides a further in vivo test for detecting 5-LO inhibitors.

Although the pharmacological properties of the compounds of the formula I vary with structural changes as expected, in general compounds of the formula I possess 5-LO inhibitory effects at the following concentrations or doses in one or more of the above tests a)-f):

Test a):
$IC_{50}$ in the range, for example, 0.1-30 μM;
Test b):
$IC_{50}$ (LTB$_4$) in the range, for example, 0.01-10 μM
$IC_{50}$ (T×B$_2$) in the range, for example, 15-200 μM;
Test c):
oral $ED_{50}$ (LTB$_4$) in the range, for example, 1-200 mg/kg;
Test d):
$IC_{50}$ (LTC$_4$) in the range, for example, 0.001-1 μM,
$IC_{50}$ (PGE$_2$) in the range, for example, 20-1000 μM;
Test e):
inhibition of inflammation in the range, for example, 0.3-100 μg intradermally;
Test f):
$ED_{50}$ in the range, for example, 0.5-10 mg/kg i.v.

No overt toxicity or other untoward effects are present in tests c), e) and/or f) when compounds of the formula I are administered at several multiples of their minimum inhibitory dose or concentration.

Thus, by way of example, the compound 2-[1-methoxy-1-[3-(naphth-2-ylmethoxy)phenyl]propyl]-thiazole has an $IC_{50}$ of 0.1 μM in test a), an $IC_{50}$ of 0.3 μM against LTB$_4$ and of >100 μM against T×B$_2$ in test b), and an oral $ED_{50}$ of 10 mg/kg versus LTB$_4$ in test c); and the compound 2-[1-[3-(3-(4-fluorophenyl)prop-2-ynyloxy)phenyl]-1-methoxypropyl]thiazole has an $IC_{50}$ of 0.04 μM against LTB$_4$ in test b) and an oral $ED_{50}$ of 10 mg/kg versus LTB$_4$ in test c).

In general those compounds of the formula I which are particularly preferred have an $IC_{50}$ of <5 μM against LTB$_4$ and of >100 μM against T×B$_2$ in test b), and an oral $ED_{50}$ of <100 mg/kg against LTB$_4$ in test c).

These compounds are examples of thiazoles of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a thiazole of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is a thiazole of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

The invention also includes a thiazole of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a thiazole of the formula I will naturally vary according to the nature and severity of the conditions, the age and sex of the animal or patient and the route of administration, according to well known principles of medicine. As mentioned above, thiazoles of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovasular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a thiazole of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range 18°-20° and under an atmosphere of an inert gas such as argon;

(iii) column chromatography (by the flash procedure) and medium pressure liquid chromatography (MPLC) were performed on Merck Kieselgel silica (Art. 9385) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis; and (vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture.

EXAMPLE 1

A mixture of 2-[1-(3-hydroxyphenyl)-1-methoxypropyl]thiazole (1.5 g), 2-bromomethylnaphthalene (1.48 g), potassium carbonate (0.84 g) and dimethylformamide (15 ml) was stirred at ambient temperature for 18 hours. The mixture was filtered, the filtrate was added to water (100 ml) and the mixture was extracted with ethyl acetate (3×50 ml). The organic extracts were combined, washed with a dilute aqueous sodium hydroxide solution and with water, dried ($Na_2SO_4$) and evaporated. There was thus obtained 2-[1-methoxy-1-[3-(naphth-2-ylmethoxy)phenyl]propyl]thiazole (1.77 g, 75%), m.p. 91°-92° C. (recrystallised from methanol).

The thiazole starting material was obtained as follows:

A slurry of 3-hydroxybenzaldehyde (38 g) in diethyl ether (250 ml) was added over 1 hour to a diethyl ether solution of ethylmagnesium bromide [prepared from bromoethane (75 ml) and magnesium turnings (24 g) under diethyl ether (150 ml)] which had been cooled in an ice-bath to 0° C. The mixture was stirred for 16 hours and allowed to warm to ambient temperature. The mixture was poured into a 5% aqueous hydrochloric acid solution and the resulting mixture was extracted with ethyl acetate (2×500 ml). The combined organic extracts were washed with water, with a saturated aqueous sodium chloride solution, dried ($Na_2SO_4$) and evaporated. The residue was purified by recrystallisation from a mixture of petrol (b.p. 60°-80° C.) and ethyl acetate. There was thus obtained α-ethyl-3-hydroxybenzyl alcohol (26.7 g).

A mixture of the product so obtained (25 g), 2,3-dichloro-5,6-dicyano-1,4-benzoquinone (40 g) and 1,4-dioxan (900 ml) was stirred at ambient temperature for 3 days. The resulting suspension was filtered and the filtrate was evaporated. The residue was purified by recrystallisation from ethyl acetate to give 3-hydroxypropiophenone (18.8 g).

Tert-butyldimethylsilyl chloride (22.5 g) was added to a mixture of 3-hydroxypropiophenone (18.7 g), imidazole (21.3 g) and dimethylformamide (100 ml) and the solution was stirred at ambient temperature for 6 hours. The mixture was evaporated and the residue was partitioned between ethyl acetate and water. The organic layer was separated, washed with an aqueous sodium chloride solution, dried ($Na_2SO_4$) and evaporated. Petrol (b.p. 60°-80° C., 250 ml) was added to the residue, the resulting mixture was filtered and the filtrate was evaporated to give 3-(tert-butyldimethylsilyloxy)propiophenone as a pale yellow oil (31 g) which was used without further purification.

A solution of the product so obtained (31 g) in tetrahydrofuran (70 ml) was added dropwise to a cooled (−70° C.) solution of thiazol-2-yl-lithium [prepared by adding a solution of n-butyl-lithium (1.6M in hexane, 80 ml) to a mixture of thiazole (8.8 ml) and tetrahydrofuran (130 ml) which had been cooled to −70° C.]. The mixture was stirred at this temperature for 1 hour and at ambient temperature for 2 hours. The mixture was then poured into a cooled, dilute aqueous solution of ammonium acetate and extracted with diethyl ether (3×100 ml). The combined organic extracts were washed with water and with a saturated aqueous sodium chloride solution, dried (Na₂SO₄) and evaporated. The residue was purified by column chromatography eluting with toluene/ethyl acetate (5/1 v/v) to give 2-[1-(3-tert-butyldimethylsilyloxyphenyl)-1-hydroxypropyl]-thiazole as a pale red oil (31 g).

A solution of the product so obtained (31 g) in tetrahydrofuran (150 ml) was added to a slurry of sodium hydride (55% w/w dispersion in oil, 5 g) in tetrahydrofuran (50 ml) and the mixture was stirred at ambient temperature for 1 hour. Methyl iodide (6.6 ml) was added dropwise and the mixture was stirred at ambient temperature for 5 hours. The mixture was poured into a saturated aqueous ammonium chloride solution and extracted with ethyl acetate (3×100 ml). The combined extracts were dried (Na₂SO₄) and evaporated and the residue was purified by column chromatography eluting with toluene/ethyl acetate (20/1 v/v) to give 2-[1-(3-tert-butyldimethylsilyloxyphenyl)-1-methoxypropyl]thiazole as a pale yellow oil (20.2 g).

A mixture of the product so obtained (20 g), trifluoroacetic acid (112 ml) and water (12 ml) was stirred at ambient temperature for 3 hours. The mixture was evaporated, toluene (100 ml) was added and the mixture was re-evaporated. The residue was partitioned between diethyl ether (150 ml) and dilute aqueous sodium hydroxide solution (150 ml). The aqueous solution was acidified to pH4 by the addition of dilute aqueous hydrochloric acid solution and an ethyl acetate extract (3×80 ml) was taken. The combined extracts were washed with water, dried (Na₂SO₄) and evaporated. The residue was recrystallised from a mixture of petrol (b.p. 60°–80° C.) and ethyl acetate to give 2-[1-(3-hydroxyphenyl)-1-methoxypropyl]thiazole (8 g), m.p. 101°–103° C.

EXAMPLE 2

Using a similar procedure to that described in Example 1 except that the appropriate alkylating agent was used in place of 2-bromomethylnaphthalene there were obtained the compounds described in the following table:

ture for 30 minutes. Methyl iodide (1 ml) was added and the mixture was stirred at ambient temperature for 3 hours. The mixture was poured into a saturated aqueous ammonium chloride solution and extracted with ethyl acetate (3×10 ml). The combined extracts were dried (MgSO₄) and evaporated and the residue was purified by column chromatography eluting with methylene chloride to give a gum which crystallised on standing and was recrystallised from methanol. There was thus obtained 2-[1-methoxy-1-[3-methoxy-5-(naphth-2-ylmethoxy)phenyl]propyl]thiazole (0.23 g, 32%), m.p. 88° C.

The thiazole starting material was obtained as follows:

Methyl iodide (36 ml) was added to a mixture of methyl 3,5-dihydroxybenzoate (104 g), potassium carbonate (79 g) and dimethylformamide (1200 ml) and the mixture was stirred at ambient temperature for 16 hours. The mixture was partitioned between water (2.5 liter) and petrol (b.p. 60°–80° C., 600 ml). The aqueous layer was washed with petrol (b.p. 60°–80° C., 600 ml) and then extracted with toluene (2×1 liter). The toluene extracts were combined, washed with water (4×800 ml), dried (MgSO₄) and evaporated to give methyl 3-hydroxy-5-methoxybenzoate as an oil (33 g, 30%).

The product so obtained (33 g) was alkylated with 2-bromomethylnaphthalene (36.5 g) using the procedure described in the first paragraph of Example 1. There was thus obtained methyl 3-methoxy-5-(naphth-2-ylmethoxy)benzoate (50.5 g, 91%), m.p. 85°–86° C. (recrystallised from petrol (b.p. 60°–80° C.)).

A solution of the product so obtained (50 g) in tetrahydrofuran (800 ml) was cooled to −70° C. and to this was added a cooled (−70° C.) solution of thiazol-2-yl-lithium [prepared by adding 2-bromothiazole (25.6 g) to a mixture of n-butyl-lithium (1.5M in hexane, 100 ml) and diethyl ether (300 ml) which had been cooled to −70° C.]. The mixture was stirred at −20° C. for 30 minutes, poured into a saturated aqueous ammonium chloride solution and extracted with diethyl ether (3×200 ml). The combined extracts were washed with water, dried (MgSO₄) and evaporated. The residue was purified by crystallisation from acetone to give 3-methoxy-5-(naphth-2-ylmethoxy)phenyl 2-thiazolyl ke-

TABLE I

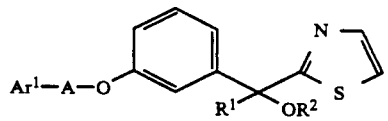

| Ex. 2 Compd. No. | Ar¹ | A | R¹ | R² | m.p. (°C.) | Yield (%) |
|---|---|---|---|---|---|---|
| 1ᵃ | 3-trifluoromethyl-phenyl | CH₂ | Et | Me | 48–50 | 82 |
| 2ᵇ | phenyl | —C≡C—CH₂— | Et | Me | oil | 60 |

Notes
ᵃ3-Trifluoromethylbenzyl chloride was used as the alkylating agent. The product was purified by column chromatography eluting with toluene/ethyl acetate (20/1 v/v).
ᵇ3-Phenylprop-2-ynyl bromide was used as the alkylating agent. The product was purified by column chromatography eluting with methylene chloride and then with methylene chloride/diethyl ether (9/1 v/v) to give an oil which was characterised by the following data:-
Mass Spectrum: m/e 364 (P + 1);
Analysis: Found C, 71.3; H, 5.8; N, 3.7;
C₂₂H₂₁NO₂S requires C, 72.7; H, 5.8; N, 3.9%.

EXAMPLE 3

A solution of 2-[1-hydroxy-1-[3-methoxy-5-(naphth-2-yl-methoxy)phenyl]propyl]thiazole (0.7 g) in tetrahydrofuran (8 ml) was added to slurry of sodium hydride (55% w/w dispersion in oil, 0.105 g) in tetrahydrofuran (2 ml) and the mixture was stirred at ambient temperatone (34 g, 60%), m.p. 105°–106° C.

A solution of the ketone so obtained (1.2 g) in tetrahydrofuran (20 ml) was added to a diethyl ether solution of ethylmagnesium iodide [prepared from iodoethane (0.6 ml) and magnesium turnings (0.154 g) under diethyl ether (10 ml)] and the mixture was heated to reflux for 15 minutes. The mixture was poured into a saturated aqueous ammonium chloride solution and extracted with ethyl acetate (3×15 ml). The combined extracts were washed with water, dried (MgSO$_4$) and evaporated. The residue was purified by column chromatography eluting with methylene chloride/ethyl acetate (17/3 v/v) to give 2-[1-hydroxy-1-[3-methoxy-5-(naphth-2-ylmethoxy)phenyl]propyl]thiazole (0.72 g, 55%), m.p. 105° C. (recrystallised from a mixture of petrol (b.p. 60°-80° C.) and ethyl acetate).

EXAMPLE 4

Powdered potassium hydroxide (0.155 g) was added to a solution of 2-[1-hydroxy-1-[5-(naphth-2-ylmethoxy)pyrid-3-yl]propyl]thiazole (0.218 g) in dimethylsulphoxide (2 ml) and the mixture was stirred at ambient temperature for 5 minutes. Methyl iodide (0.073 ml) was added and the mixture was stirred at ambient temperature for 30 minutes. The mixture was partitioned between water and methylene chloride (3×20 ml). The organic extracts were combined, dried (Na$_2$SO$_4$) and evaporated. The residue was purified by column chromatography eluting with increasingly polar mixtures of petrol (b.p. 60°-80° C.) and ethyl acetate to give 2-[1-methoxy-1-[5-(naphth-2-ylmethoxy)pyrid-3-yl]propyl]thiazole (0.14 g, 62%), m.p. 93°-95° C.

The thiazole starting material was obtained as follows:

A solution of 2-naphthylmethanol (1.58 g) in dimethylformamide (20 ml) was added to a slurry of sodium hydride (55% w/w dispersion in oil, 0.48 g) in dimethylformamide (2 ml) and the mixture was stirred at ambient temperature for 20 minutes. 3,5-Dibromopyridine (2.37 g) was added and the solution was heated to 120° C. for 5 hours and then allowed to stand at ambient temperature overnight. The mixture was poured into water (160 ml) and extracted with ethyl acetate (3×50 ml). The combined extracts were washed with water, dried (MgSO$_4$) and evaporated. The residue was purified by column chromatography eluting with increasingly polar mixtures of petrol (b.p. 60°-80° C.) and ethyl acetate to give 3-bromo-5-(naphth-2-ylmethoxy)pyridine (1.4 g), m.p. 108°-109° C.

A solution of the product so obtained (1.26 g) in diethyl ether (30 ml) was cooled to −50° C. and n-butyl-lithium (1.5M in hexane, 3.6 ml) was added dropwise over 10 minutes. The mixture was stirred at −40° C. for 10 minutes, cooled to −70° C. and a solution of ethyl 2-thiazolyl ketone (0.56 g; *Bull. Soc. Chim. France*, 1962, 2072) in diethyl ether (15 ml) was added. The mixture was stirred at −70° C. for 30 minutes, allowed to warm to ambient temperature, poured into a saturated aqueous ammonium chloride solution and extracted with ethyl acetate (3×30 ml). The combined extracts were washed with water, dried (MgSO$_4$) and evaporated. The residue was purified by column chromatography eluting with increasingly polar mixtures of petrol (b.p. 60°-80° C.) and ethyl acetate to give 2-[1-hydroxy-1-[5-(naphth-2-yl-methoxy)pyrid-3-yl]propyl]thiazole (0.5 g), m.p. 48°-50° C.

EXAMPLE 5

Using a similar procedure to that described in Example 1 except that the appropriate alkyl bromide was used in place of 2-bromomethylnaphthalene and, where appropriate, 2-[1-(3-hydroxyphenyl)-1-methoxyethyl]thiazole was used in place of 2-[1-(3-hydroxyphenyl)-1-methoxypropyl]thiazole there were obtained the compounds described in the following table. The products were purified by column chromatography eluting with increasingly polar mixtures of toluene and ethyl acetate.

TABLE II

| Ex. 5 Compd. No. | Ar$^1$ | A | R$^1$ | R$^2$ | m.p. (°C.) | Yield (%) |
|---|---|---|---|---|---|---|
| 1* | 1-naphthyl | CH$_2$ | Et | Me | 87–88 | 85 |
| 2 | 3-iodophenyl | CH$_2$ | Et | Me | oil | 86 |
| 3 | 3,4-dichlorophenyl | CH$_2$ | Et | Me | 60–62 | 73 |
| 4 | 3-cyanophenyl | CH$_2$ | Et | Me | 98–99 | 96 |
| 5* | 3,4-dimethoxyphenyl | CH$_2$ | Et | Me | 121–122 | 53 |
| 6 | 3-methoxycarbonylphenyl | CH$_2$ | Et | Me | oil | 98 |
| 7* | 4-methylthiophenyl | CH$_2$ | Et | Me | 75–76 | 40 |
| 8 | 4-cyanophenyl | CH$_2$ | Et | Me | oil | 81 |
| 9* | 4-chlorophenyl | CH$_2$ | Et | Me | oil | 75 |
| 10 | 4-trifluoromethylphenyl | CH$_2$ | Et | Me | 43–45 | 94 |
| 11 | phenyl | —CH=CH—CH$_2$— | Et | Me | 61–62 | 55 |
| 12 | 3-trifluoromethylphenyl | —CH=CH—CH$_2$— | Et | Me | 50–52 | 55 |
| 13 | 3-cyanophenyl | —CH=CH—CH$_2$— | Et | Me | 74–76 | 75 |
| 14 | 2-trifluoromethylphenyl | —CH=CH—CH$_2$— | Et | Me | oil | 95 |
| 15 | 2,6-dichlorophenyl | —CH=CH—CH$_2$— | Et | Me | 70–73 | 29 |
| 16** | 3,4,5-trimethoxyphenyl | —CH=CH—CH$_2$— | Et | Me | oil | 69 |
| 17 | 3,4-difluorophenyl | —CH=CH—CH$_2$— | Et | Me | 48–52 | 93 |
| 18 | 2,6-difluorophenyl | —CH=CH—CH$_2$— | Et | Me | 93–95 | 96 |
| 19 | phenyl | —CH=CH—CH$_2$— | Et | Me | oil | 53 |
| 20+ | 4-methylphenyl | —C≡C—CH$_2$— | Et | Me | oil | 70 |
| 21+ | 4-methylphenyl | —C≡C—CH$_2$— | Me | Me | oil | 74 |
| 22+ | 2-chlorophenyl | —C≡C—CH$_2$— | Et | Me | oil | 75 |
| 23+ | 2-chlorophenyl | —C≡C—CH$_2$— | Me | Me | oil | 77 |

TABLE II-continued

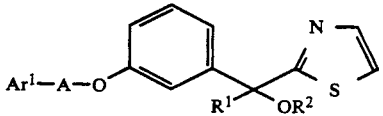

| Ex. 5 Compd. No. | Ar¹ | A | R¹ | R² | m.p. (°C.) | Yield (%) |
|---|---|---|---|---|---|---|
| 24+ | 3-chlorophenyl | —C≡C—CH₂— | Et | Me | oil | 75 |
| 25+ | 3-chlorophenyl | —C≡C—CH₂— | Me | Me | oil | 64 |
| 26+ | 4-chlorophenyl | —C≡C—CH₂— | Et | Me | oil | 57 |
| 27+ | 2-trifluoromethyl-phenyl | —C≡C—CH₂— | Et | Me | oil | 74 |
| 28+ | 2-trifluoromethyl-phenyl | —C≡C—CH₂— | Me | Me | oil | 67 |
| 29+ | 3-trifluoromethyl-phenyl | —C≡C—CH₂— | Et | Me | oil | 50 |
| 30+ | 3-trifluoromethyl-phenyl | —C≡C—CH₂— | Me | Me | oil | 50 |
| 31ª | 2-naphthyl | CH₂ | Me | Me | 90–91 | 80 |
| 32ᵇ | 6-methylnaphth-2-yl | CH₂ | Et | Me | 72–74 | 64 |
| 33 | 6-fluoronaphth-2-yl | CH₂ | Et | Me | 78–80 | 80 |
| 34 | 7-fluoronaphth-2-yl | CH₂ | Et | Me | 63–65 | 61 |
| 35 | 1-cyanonaphth-2-yl | CH₂ | Et | Me | 141–142 | 54 |
| 36 | 5-cyanonaphth-2-yl | CH₂ | Et | Me | 134–136 | 49 |
| 37 | 1-trifluoromethyl-naphth-2-yl | CH₂ | Et | Me | 98–100 | 57 |
| 38 | 3-difluoromethyl-naphth-2-yl | CH₂ | Et | Me | 83–85 | 34 |
| 39 | 7-difluoromethyl-naphth-2-yl | CH₂ | Et | Me | oil | 72 |

Notes
*The appropriate alkyl chloride was used in place of the corresponding alkyl bromide.
+Acetone was used in place of dimethylformamide as the reaction solvent.
The olefinic compounds Nos. 11 to 19, prepared using (E)-cinnamyl bromides, were obtained as the (E)-isomers.
**The alkylating agent was (E)-3-(3,4,5-trimethoxyphenyl)prop-2-en-1-yl methanesulphonate which was prepared as described below:-Methanesulphonyl chloride (0.31 g) was added to a mixture of (E)-3-(3,4,5-trimethoxyphenyl)prop-2-en-1-ol (0.56 g), triethylamine (0.38 ml) and methylene chloride (6 ml) which had been cooled to 0° C.. The mixture was stirred at 0° C. for 1.5 hours. The mixture was partitioned between methylene chloride and water and the organic layer was separated, dried (MgSO₄) and evaporated to give the required methanesulphonate which was used without further purification.
ªThe product was purified by recrystallisation from isopropanol.
ᵇThe alkylating agent, 2-Bromomethyl-6-methylnaphthalene is described in J. Chem. Soc., 1946, 830.

For those compounds within Example 5 which were oils the following NMR data were obtained (unless otherwise stated the compounds were all dissolved in CDCl₃ and chemical shift values are give on the δ scale):

Compound No. 2: (CD₃SOCD₃) 0.65 (t, 3H), 2.35 (m, 1H), 2.6 (m, 1H), 3.1 (s, 3H), 5.05 (s, 2H), 6.95 (m, 3H), 7.16 (t, 1H), 7.25 (d, 1H), 7.45 (d, 1H), 7.7 (m, 3H), 7.8 (s, 1H).

Compound No. 6: 0.75 (t, 3H), 2.4 (m, 1H), 2.7 (m, 1H), 3.2 (s, 3H), 5.1 (s, 2H), 7.25 and 7.7 (2d's, 2H, thiazole H's), 6.8–8.1 (m, 8H).

Compound No. 8: 0.76 (t, 3H), 2.34–2.49 (m, 1H), 2.57–2.72 (m, 1H), 3.20 (s, 3H), 5.09 (s, 2H), 6.8–7.69 (m, 10H).

Compound No. 9: 0.76 (t, 3H), 2.3–2.51 (m, 1H), 2.58–2.80 (m, 1H), 3.20 (s, 3H), 6.75–7.75 (m, 10H).

Compound No. 14: (CD₃SOCD₃) 0.7 (t, 3H), 2.3–2.7 (m, 2H), 3.1 (s, 3H), 4.8 (m, 2H), 7.2 and 7.7 (2d's, 2H, thiazole H's), 6.5–6.6 (2 t's, 1H, olefinic), 6.8–7.0 (d, 1H, olefinic), 6.8–7.7 (m, 8H).

Compound No. 16: 0.8 (t, 3H), 2.3–2.5 (m, 1H), 2.6–2.8 (m, 1H), 3.2 (s, 3H), 3.8–3.9 (3 s's, 9H), 4.6–4.7 (d, 2H), 6.2–6.4 (2 t's, 1H, olefinic), 6.6–6.7 (d, 1H, olefinic), 6.6–7.3 (m, 6H), 7.2 and 7.7 (2d's, 2H, thiazole H's).

Compound No. 19: 0.8 (t, 3H), 1.95 (s, 3H), 2.3–2.5 (m, 1H), 2.6–2.8 (m, 1H), 3.2 (s, 3H), 4.55 (s, 2H), 6.6 (s, 1H, olefinic), 6.8–7.4 (m, 10H), 7.7 (d, 1H, thiazole H).

Compound No. 20: 0.8 (t, 3H), 2.35 (s, 3H), 2.4 (m, 1H), 2.7 (m, 1H), 3.3 (s, 3H), 4.9 (s, 2H), 6.9–7.4 (m, 8H), 7.2 and 7.7 (2 d's, 2H, thiazole H's).

Compound No. 21: 2.05 (s, 3H), 2.35 (s, 3H), 3.3 (s, 3H), 4.9 (s, 2H), 6.9–7.4 (m, 8H), 7.2 and 7.7 (2 d's, 2H, thiazole H's).

Compound Nos. 22, 24, 26, 27 and 29 gave as expected very similar NMR data to those of Compound No. 20 except that the signal at 2.35δ (p-CH₃) was missing.

Compound Nos. 23, 25, 28 and 30 gave as expected very similar NMR data to those of Compound No. 21 except that the signal at 2.35δ (p-CH₃) was missing.

Compound No. 39: 0.75 (t, 3H), 2.4 (m, 1H), 2.7 (m, 1H), 3.2 (s, 3H), 5.2 (s, 2H), 6.8 (t, 1H, CHF₂, J=110 Hz, 6.9–7.9 (m, 12H).

Information concerning the preparation of appropriate starting materials is provided below:

2-[1-(3-Hydroxyphenyl)-1-methoxyethyl]thiazole, m.p. 158°–160° C., was prepared using the procedure described in Example 1 for the preparation of 2-[1-(3-hydroxyphenyl)-1-methoxypropyl]thiazole except that 3-hydroxyacetophenone was used in place of 3-hydroxypropiophenone.

The procedure used to prepare the appropriate (E)-cinnamyl bromide for use in the preparation of compounds Nos. 12 to 15, 17 and 18 is illustrated below by the description of the preparation of (E)-3-(3-trifluoromethylphenyl)prop-2-en-1-yl bromide. The other (E)-cinnamyl bromides were prepared in analogous fashion. Thus:

Ethyl chloroformate (1.4 ml) was added dropwise to a mixture of (E)-3-(3-trifluoromethylphenyl)propenoic acid (3.2 g), triethylamine (2.1 ml) and tetrahydrofuran (40 ml) which had been cooled to −20° C. The mixture was stirred at −20° C. for 30 minutes and filtered. The solid was washed with diethyl ether. The combined filtrate and washings were added dropwise to a solution of sodium borohydride (1.43 g) in water (15 ml) which had been cooled to 3° C. The mixture was stirred at ambient temperature for 3 hours then partitioned between diethyl ether and 2N hydrochloric acid solution. The organic layer was separated, washed with water and with 1N sodium hydroxide solution, dried (MgSO$_4$) and evaporated. The residue was purified by column chromatography using a 4:1 v/v mixture of toluene and ethyl acetate as eluent. There was thus obtained (E)-3-(3-trifluoromethylphenyl)prop-2-en-1-ol as a colorless oil (2.53 g).

Bromine (0.234 ml) was added dropwise to a mixture of triphenylphosphine (1.18 g) and methylene chloride (15 ml) which had been cooled to 3° C. A cooled (3° C.) solution of the prop-2-en-1-ol (0.8 g) described above in methylene chloride (5 ml) was added and the mixture was stirred for 10 minutes and then evaporated. The residue was triturated under diethyl ether (20 ml) and filtered. The filtrate was dried (MgSO$_4$) and evaporated. There was thus obtained (E)-3-(3-trifluoromethylphenyl)prop-2-en-1-yl bromide as an oil (1 g).

(E)-3-(3,4,5-Trimethoxyphenyl)prop-2-en-1-ol used in the preparation of the corresponding methanesulphonate for the preparation of Compound No. 16 was prepared in analogous fashion.

(E)-2-Methyl-3-phenylprop-2-en-1-yl bromide used as the alkylating agent for Compound No. 19 was prepared as follows:

A mixture of α-methylcinnamaldehyde (1.46 g), sodium cyanoborohydride (1.25 g), methyl orange indicator (1 drop) and methanol (20 ml) was acidified to pH3 by the addition of 2N hydrochloric acid solution. The mixture was stirred at ambient temperature for 1.5 hours with sufficient further additions of 2N hydrochloric acid solution to maintain the reaction mixture at pH3. The mixture was evaporated and the residue was partitioned between diethyl ether and 2N hydrochloric acid solution. The organic layer was washed with water, dried (MgSO$_4$) and evaporated. The residue was purified by column chromatography using a 7:1 v/v mixture of toluene and ethyl acetate as eluent. There was thus obtained (E)-2-methyl-3-phenylprop-2-en-1-ol as an oil (1.03 g) which was converted to (E)-2-methyl-3-phenylprop-2-en-1-yl bromide using the procedure described above involving bromine and triphenylphosphine.

The procedure used to prepare the appropriate 3-phenylprop-2-ynyl bromide for use in the preparation of Compounds Nos. 20 to 30 is illustrated below by the description of the preparation of 3-(2-chlorophenyl)-prop-2-ynyl bromide. The other 3-phenylprop-2-ynyl bromides were prepared in analogous fashion. Thus:

2-Propynyl alcohol (4.65 ml) was added in one portion to a stirred mixture of 2-chloroiodobenzene (4.76 g), bis(triphenylphosphine)palladium chloride (0.2 g), cuprous iodide (0.2 g), triethylamine (2.78 ml) and acetonitrile (80 ml) and the mixture was heated to 55° C. for 1 hour. The mixture was cooled to ambient temperature, poured into water (200 ml) and neutralised by the addition of dilute hydrochloric acid solution. The mixture was extracted with ethyl acetate (2×75 ml) and the combined extracts were washed with water (100 ml), with a saturated aqueous sodium chloride solution (100 ml), dried (MgSO$_4$) and evaporated. The residue was purified by column chromatography using methylene chloride as eluent. There was thus obtained 3-(2-chlorophenyl)prop-2-ynyl alcohol as an oil in 60% yield.

A solution of bromine (1.9 g) in methylene chloride (3 ml) was added to a solution of triphenylphosphine (3.46 g) in methylene chloride (40 ml) which had been cooled to 0° C. A solution of a portion (2 g) of the alcohol obtained immediately above in methylene chloride (36 ml) was added and the mixture was stirred for 1 hour and maintained at approximately 3° C. The mixture was evaporated and the residue was purified by column chromatography using methylene chloride as eluent. There was thus obtained 3-(2-chlorophenyl)prop-2-ynyl bromide as an oil in 53% yield.

The procedure used to prepare the appropriate 2-bromomethylnaphthalene for use in the preparation of Compounds Nos 33 to 39 is illustrated below by the description of the preparation of 2-bromomethyl-5-cyanonaphthalene. The other 2-bromomethylnaphthalenes were prepared in analogous fashion. Thus:

A mixture of 5-cyano-2-methylnaphthalene (0.75 g), N-bromosuccinimide (0.81 g), 2,2'-azobisisobutyronitrile (0.05 g) and carbon tetrachloride (25 ml) was heated to reflux and irradiated with the light from a 275 watt bulb for 1 hour. The mixture was cooled to ambient temperature and filtered. The filtrate was evaporated and the residue was recrystallized from carbon tetrachloride. There was thus obtained 2-bromoethyl-5-cyanonaphthalene (0.64 g), m.p. 104°–106° C.

The procedure described immediately above was repeated except that the appropriate 2-methylnaphthalene was used in place of 5-cyano-2-methylnaphthalene and the reaction product was purified by column chromatography using increasingly polar mixtures of petroleum ether (b.p. 60°–80° C.) and toluene as eluent. There were thus obtained the 2-bromomethylnaphthalenes listed below:

2-bromomethyl-6-fluoronaphthalene[a], m.p. 48° C.;
2-bromomethyl-7-fluoronaphthalene[b], m.p. 62° C.;
2-bromomethyl-1-cyanonaphthalene[c], oil;
2-bromomethyl-1-trifluoromethylnaphthalene[d], oil;
2-bromomethyl-7-difluoromethylnaphthalene[e], m.p. 70°–71° C.; and
2-bromomethyl-3-difluoromethylnaphthalene[f], oil.

Notes
a. 2-Methyl-6-fluoronaphthalene used as a starting material was obtained as follows: 4-Fluorobenzyl chloride was reacted with acetylacetaldehyde dimethylacetal using the procedure described for the corresponding reaction of 3-methylbenzyl chloride (*Synthesis*, 1974, 566). there was thus obtained 4-(4-fluorophenyl)-3-hydroxy-3-methylbutanal dimethylacetal (b.p. 122°–130° C. at 0.2 mm Hg). A mixture of the material so obtained (15 g), glacial acetic acid (60 ml) and hydrobromic acid (48% w/v. 48 ml) was heated on a steam bath for 1 hour. The mixture was evaporated and the residue was purified by column chromatography using petroleum ether (b.p. 60°–80° C.) as eluent. There was thus obtained 6-fluoro-2-methylnaphthalene (1 g).
b. The procedure described in Note a. above was repeated except that 3-fluorobenzyl chloride was used. There was thus obtained 7-fluoro-2-methylnaphthalene as a white solid.
c. 1-Cyano-2-methylnaphthalene used as a starting material is described in *J. Amer. Chem. Soc*, 1982, 104, 4644.
d. 2-Methyl-1-trifluoromethylnaphthalene used as a starting material was obtained as follows: A mixture of 1-bromo-2-methylnaphthalene (5 g), sodium trifluoroacetate (12.3 g), cuprous iodide (8.6 g) and N,N-dimethylacetamide (100 ml) was stirred and heated to 160° C. for 6 hours. The mixture was cooled, filtered and evaporated. The filtrate was washed with water and with a saturated sodium chloride solution, dried (MgSO$_4$) and evaporated. The residue was purified by column chromatography using a 49:1 v/v mixture of petroleum ether (b.p. 60°–80° C.) and toluene as eluent. There was thus obtained 2-methyl-1-trifluoromethylnaphthalene as a colorless oil (2.08 g).
e. 7-Difluoromethyl-2-methylnaphthalene used as a starting material was obtained as follows:

A mixture of 2-methyl-7-naphthaldehyde (0.37 g; *Bull. Soc. Chim. Belg.*, 1985, 94, 205), diethylaminosulphur trifluoride (0.3 ml) and methylene chloride (3 ml) was stirred at ambient temperature for 16 hours. A second portion of the trifluoride (0.6 ml) was added and the reaction was continued for a further 24 hours. The mixture was partitioned between methylene chloride and water. The organic layer was washed with water, dried (MgSO4) and evaporated. The residue was purified by column chromatography using a 19:1 v/v mixture of petroleum ether (b.p. 60°–80° C.) and toluene as eluent. There was thus obtained 7-difluoromethyl-2-methylnaphthalene as a solid (0.13 g).

f. The procedure described in Note e. above was repeated except that 2-methyl-3-naphthaldehyde was used as a starting material. There was thus obtained 3-difluoromethyl-2-methylnaphthalene as a white solid.

EXAMPLE 6

Using a similar procedure to that described in Example 1 a mixture of 2-[1-(4-hydroxy-3-methoxyphenyl)-1-methoxypropyl]thiazole (0.6 g), 3-(2-chlorophenyl)-prop-2-ynyl bromide (0.6 g), potassium carbonate (0.7 g) and dimethylformamide was stirred at ambient temperature for 16 hours. The crude product was purified by column chromatography using methylene chloride as eluent. There was thus obtained 2-[1-[4-(3-(2-chlorophenyl)prop-2-ynyloxy)-3-methoxyphenyl]-1-methoxypropyl]thiazole as an oil (0.3 g).

NMR Spectrum (CDCl3, δ values) 0.8 (t, 3H), 2.3–2.5 (m, 1H), 2.6–2.8 (m, 1H), 3.2 (s, 3H), 3.85 (s, 3H), 5.0 (s, 2H), 7.2–8.2 (m, 9H, aromatics).

The thiazole used as a starting material was obtained as follows:

Tert-butyldimethylsilyl chloride (12 g) was added to a mixture of ethyl vanillate (15 g), imidazole (13 g) and tetrahydrofuran (100 ml) and the mixture was stirred at ambient temperature for 48 hours. The mixture was filtered and evaporated to give ethyl 4-(tert-butyldimethylsilyloxy)-3-methoxybenzoate (25.1 g). A solution of the product so obtained in tetrahydrofuran (50 ml) was cooled to −70° C. and to this was added a cooled (−70° C.) solution of thiazol-2-yl-lithium [prepared by adding 2-bromothiazole (14.1 g) to a mixture of n-butyl-lithium (1.5M in hexane, 57.3 ml) and diethyl ether (30 ml) which had been cooled to −70° C.]. The mixture was stirred for 16 hours and allowed to warm to ambient temperature. The mixture was poured into a saturated aqueous ammonium chloride solution and extracted with ethyl acetate (3×100 ml). The combined extracts were washed with water and with a saturated aqueous sodium chloride solution, dried (MgSO4) and evaporated. The residue was purified by column chromatography using increasingly polar mixtures of methylene chloride and ethyl acetate as eluent. There was thus obtained 4-hydroxy-3-methoxyphenyl 2-thiazolyl ketone (4.5 g) in 24% yield, m.p. 103° C.

The product so obtained (4.0 g) was reacted with tert-butyldimethylsilyl chloride using the procedure described immediately above to give 4-tert-butyldimethylsilyloxy-3-methoxyphenyl 2-thiazolyl ketone (6.5 g). A solution of a portion of the ketone so obtained (5.9 g) in tetrahydrofuran (5 ml) was added to a diethyl ether solution of ethylmagnesium iodide [prepared from iodoethane (2.8 ml) and magnesium (0.816 g) under diethyl ether (10 ml)] and the mixture was heated to reflux for 15 minutes. The mixture was poured into a saturated aqueous ammonium chloride solution and extracted with ethyl acetate (3×25 ml). The combined extracts were washed with water (2×50 ml), with a saturated aqueous sodium chloride solution, dried (MgSO4) and evaporated. There was thus obtained 2-[1-(4-tert-butyldimethylsilyloxy-3-methoxyphenyl)-1-hydroxypropyl]thiazole (5.8 g).

The product so obtained was reacted with methyl iodide using the procedure described in Example 1 except that the product was purified by column chromatography using increasingly polar mixtures of methylene chloride and ethyl acetate as eluent. There was thus obtained 2-[1-(4-tert-butyldimethylsilyloxy-3-methoxyphenyl)-1-methoxypropyl]thiazole (3 g).

Tetra-n-butylammonium fluoride (1M in tetrahydrofuran; 16 ml) was added over 5 minutes to a solution of the product so obtained in tetrahydrofuran (50 ml). The mixture was poured into a saturated aqueous ammonium chloride solution and extracted with ethyl acetate (3×70 ml). The combined extracts were washed with water, with a saturated aqueous sodium chloride solution, dried (MgSO4) and evaporated. There was thus obtained 2-[1-(4-hydroxy-3-methoxyphenyl)-1-methoxypropyl]thiazole (1.3 g), m.p. 127°–129° C. (recrystallised from a mixture of petroleum ether (b.p 60°–80° C.) and methylene chloride).

EXAMPLE 7

The procedure described in Example 6 was repeated except that 3-(4-chlorophenyl)prop-2-ynyl bromide was used in place of the corresponding 2-chlorophenyl isomer. There was thus obtained 2-[1-[4-(3-(4-chlorophenyl)prop-2-ynyloxy)-3-methoxyphenyl]-1-methoxypropyl]-thiazole as an oil in 30% yield.

NMR Spectrum (CDCl3, δ values) 0.8 (t, 3H), 2.35–2.48 (m, 1H), 2.6–2.75 (m, 1H), 3.2 (s, 3H), 3.85 (s, 3H), 4.95 (s, 2H), 7.0 (s, 4H), 7.7 (d, 1H), 7.2–7.4 (m, 4H).

EXAMPLE 8

A mixture of 2-[1-(5-hydroxypyrid-3-yl)-1-methoxypropyl]thiazole (0.5 g), sodium hydride (50% w/w dispersion in oil, 0.096 g) and dimethylformamide (20 ml) was stirred at ambient temperature for 30 minutes. The mixture was cooled to −5° C. and a solution of 3-phenylprop-2-ynyl bromide (0.39 g) in dimethylformamide (5 ml) was added. The mixture was stirred at −5° C. for 1 hour and then partitioned between ethyl acetate and water. The organic layer was dried (MgSO4) and evaporated. The residue was purified by column chromatography using ethyl acetate as eluent. There was thus obtained 2-[1-methoxy-1-[5-(3-phenylprop-2-ynyloxy)pyrid-3-yl]propyl]thiazole as an oil (0.28 g).

NMR Spectrum (CDCl3, δ values) 0.8 (t, 3H), 2.7 (m, 1H), 3.2 (s, 3H), 4.95 (s, 2H), 7.3 (m, 7H), 7.7 (d, 1H), 8.35 (2 d's, 2H).

The 2-[1-(5-hydroxypyrid-3-yl)-1-methoxypropyl]-thiazole used as a starting material was obtained as follows:

The procedure described in the portion of Example 4 which is concerned with the preparation of starting materials was repeated except that benzyl alcohol was used in place of 2-naphthylmethanol. There was thus obtained 2-[1-(5-benzyloxypyrid-3-yl)-1-hydroxypropyl]thiazole as an oil in 40% yield.

NMR Spectrum (CDCl3, δ values) 5.1 (s, 2H), 7.4 (m, 6H), 8.25 (broad s, 2H).

A mixture of the 2-[1-(5-benzyloxypyrid-3-yl)-1-hydroxypropyl]thiazole so obtained (1.63 g), sodium hydride (50% w/w dispersion in oil, 0.24 g) and dimethylformamide (25 ml) was stirred at −8° C. for 30 minutes. Methyl iodide (0.71 g) was added and the mixture was stirred at −5° C. for 1 hour, poured into a mixture of ice and water and extracted with ethyl acetate (3×25 ml). The combined extracts were washed with water, dried (MgSO₄) and evaporated. There was thus obtained 2-[1-(5-benzyloxypyrid-3-yl)-1-methoxypropyl]thiazole as an oil (1.6 g).

NMR Spectrum (CDCl₃, δ values) 0.77 (t, 3H), 2.45 (m, 1H), 2.68 (m, 1H), 3.2 (s, 3H), 5.1 (s, 2H), 7.3 (m, 6H), 7.7 (d, 1H), 8.0 (s, 1H), 8.3 (broad d, 2H), A mixture of the product so obtained (1.5 g), 30% palladium-on-charcoal catalyst (1:1 w/w mixture with water, 1.5 g) and ethyl acetate (30 ml) was stirred under an atmosphere of hydrogen for 4 hours. The mixture was filtered. The filtrate was washed with water, dried (MgSO₄) and evaporated. There was thus obtained 2-[1-(5-hydroxypyrid-3-yl)-1-methoxypropyl]thiazole as a white solid (0.78 g), m.p. 133°-135° C.

EXAMPLE 9

Using a similar procedure to that described in either Example 3 or Example 4, except that the appropriate 2-[1-hydroxyalkyl]thiazole was used in place of 2-[1-hydroxy-1-[3-methoxy-5-(naphth-2-ylmethoxy)phenyl]-propyl]thiazole (Example 3) or 2-(1-hydroxy-1-[5-(naphth-2-ylmethoxy)pyrid-3-yl]propyl]thiazole (Example 4), and the appropriate alkylating agent was, where appropriate, used in place of methyl iodide, there were obtained the compounds described in the following tables.

An asterisk (*) is used to identify those compounds which were prepared using a similar procedure to that described in Example 4.

TABLE III

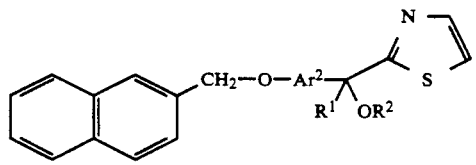

| Ex. 9 Compd. No. | Ar² | R¹ | R² | m.p. (°C.) | Yield (%) |
|---|---|---|---|---|---|
| 1ᵃ | 1,3-phenylene | H | Me | 72-74 | 60 |
| 2ᵇ | 1,3-phenylene | CF₃ | Me | 80-83 | 58 |
| 3ᶜ | 1,3-phenylene | Prⁿ | Me | 64-66 | 98 |
| 4ᵈ | 1,3-phenylene | H—C≡C— | Me | 129-130 | 75 |
| 5ᵉ | 1,3-phenylene | Me—C≡C— | Me | 108-110 | 53 |
| 6ᶠ | 1,3-phenylene | CH₂=CH— | Me | 83-85 | 55 |
| 7ᵍ | 1,3-phenylene | MeO—CH₂— | Me | 70-71 | 95 |
| 8ʰ | 1,3-phenylene | HO—CH₂— | Me | 131-132 | 63 |
| 9*,ⁱ | 1,3-phenylene | Me | —CH₂CH₂F | 87-88 | 58 |
| 10*,ʲ | 1,3-phenylene | Me | —CH₂CHF₂ | 109-111 | 13 |
| 11*,ᵏ | 2-methoxy-1,3-phenylene | Et | Me | 103-104 | 18 |
| 12ˡ | 2-methyl-1,3-phenylene | Me | Me | 101-102 | 86 |
| 13ᵐ | 6-methoxy-1,3-phenylene | Et | Me | 88-90 | 62 |
| 14* | 5-methoxy-1,3-phenylene | Et | Et | 56-58 | 78 |
| 15* | 5-methoxy-1,3-phenylene | Et | —CH₂—CH=CH₂ | 80-81 | 84 |
| 16*,ⁿ | 5-methoxy-1,3-phenylene | Et | —CH₂—C≡CH | oil | 49 |
| 17ᵒ | 5-methoxy-1,3-phenylene | Et | —CH₂CO₂Et | oil | 27 |
| 18ᵖ | 5-methoxy-1,3-phenylene | Et | —CH₂SMe | gum | 49 |
| 19ᵠ | 5-methoxy-1,3-phenylene | H—C≡C—CH₂— | Me | oil | 71 |
| 20ʳ | 5-methoxy-1,3-phenylene | NCCH₂ | Me | oil | 37 |
| 21ˢ | 5-allyloxy-1,3-phenylene | Et | Me | 85 | 64 |
| 22ᵗ | 5-hydroxy-1,3-phenylene | Et | Me | oil | 78 |
| 23ᵘ | 5-nitro-1,3-phenylene | Et | Me | 131-132 | 85 |
| 24*,ᵛ | 5-fluoro-1,3-phenylene | Et | Me | 96-98 | 77 |
| 25ʷ | 5-trifluoromethyl-1,3-phenylene | Et | Me | oil | 44 |
| 26*,ˣ | 5-trifluoromethyl-1,3-phenylene | Et | Et | oil | 42 |
| 27ʸ | 2-methoxy-1,4-phenylene | Et | Me | 88-90 | 61 |
| 28ᶻ | 2-hydroxy-1,4-phenylene | Et | Me | 131-132 | 64 |
| 29*,ᵃᵃ | 2-cyano-1,4-phenylene | Et | Me | 130 | 52 |
| 30*,ᵇᵇ | 2-tert-butoxycarbonyl-1,4-phenylene | Et | Me | 95-97 | 50 |

TABLE IV

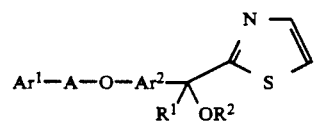

| Ex. 9 Compd. No. | Ar¹ | A | Ar² | R¹ | m.p. (°C.) | Yield (%) |
|---|---|---|---|---|---|---|
| 31*,ᶜᶜ | 2-naphthyl | CH₂ | 3,5-pyridylene | Me | 105-107 | 39 |
| 32*,ᵈᵈ | phenyl | CH₂ | 3,5-pyridylene | Et | 62-63 | 48 |
| 33*,ᵉᵉ | phenyl | —CH=CH—CH₂— | 3,5-pyridylene | Et | 47-49 | 51 |
| 34ᶠᶠ | 2-naphthyl | CH₂ | 2,6-pyridylene | Et | 58-60 | 86 |
| 35*,ᵍᵍ | 2-naphthyl | CH₂ | 4,6-pyridylene | Et | 125-126 | 67 |
| 36*,ʰʰ | 2-naphthyl | CH₂ | 2,5-pyridylene | Et | 91-93 | 62 |

TABLE IV-continued

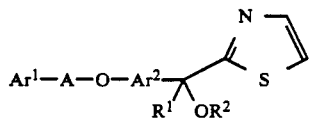

Ex. 9

| Compd. No. | Ar¹ | A | Ar² | R¹ | m.p. (°C.) | Yield (%) |
|---|---|---|---|---|---|---|
| 37*,ii | 2-naphthyl | $CH_2$ | 4,6-pyrimidinylene | Et | oil | 70 |
| 38jj | phenyl | $CH_2$ | 2-methoxy-1,4-phenylene | Et | oil | 64 |
| 39kk | phenyl | —C≡C—$CH_2$— | 2-methoxy-1,4-phenylene | Et | oil | 22 |

Notes

For the avoidance of doubt it is stated that, with regard to the location of substituents on Ar² when it is, for example, a substituted 1,3-phenylene ring, the numbering of the ring Ar² within these Tables is such that the position at which the group X is linked to Ar² is denoted by the number 1. Thus, for example, 6-methoxy-1,3-phenylene is used when the group of the formula —A—X—Ar²— is

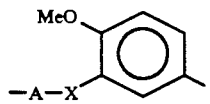

Similarly when Ar² is a heterocyclene group such as pyridylene the first number donotes the position to which the group X is attached. Thus within these Tables, for example, 4,6-pyridylene is used when the group of the formula —A—X—Ar²— is

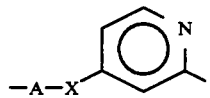

a. The 2-[3-(naphth-2-ylmethoxy)-α-hydroxybenzyl]thiazole, used as a starting material was obtained as follows:

2-Bromomethylnaphthalene was reacted with 3-hydroxybenzaldehyde using the procedure described in Example 1 to give 3-(naphth-2-ylmethoxy)benzaldehyde in 93% yield, m.p. 108°-110° C. (recrystallised from ethanol). The product so obtained was reacted with thiazol-2-yl-lithium using the procedure described in the 4th paragraph of the portion of Example 1 which is concerned with the preparation of starting materials except that the product was purified by column chromatography using a 1:1 v/v mixture of petroleum ether (b.p. 60°-80° C.) and diethyl ether as eluent. There was thus obtained the required starting material in 62% yield, m.p. 105°-106° C.

b. The product was recrystallised from petroleum ether (b.p. 60°-80° C.).

The 2-[1-hydroxy-1-(3-(naphth-2-ylmethoxy)phenyl)-2,2,2-trifluoroethyl]thiazole used as a starting material was obtained as follows:

A solution of 3-methoxy-α,α,α-trifluoroacetophenone (1.86 g; J. Med. Chem., 1986, 29, 322) in tetrahydrofuran (10 ml) was added dropwise to a cooled (−60° C.) solution of thiazol-2-yl-lithium [prepared by adding a solution of n-butyl-lithium (1.46M in hexane, 6.8 ml) to a mixture of thiazole (1 ml) and tetrahydrofuran (10 ml) which had been cooled to −60° C.]. The mixture was allowed to warm to ambient temperature and was stirred for 18 hours. The mixture was partitioned between ethyl acetate and a saturated aqueous ammonium chloride solution. The organic layer was washed with water and with a saturated aqueous sodium chloride solution, dried ($MgSO_4$) and evaporated. The solid residue was recrystallised from a mixture of hexane and ethyl acetate to give 2-[1-hydroxy-1-(3-methoxyphenyl)-2,2,2-trifluoroethyl]thiazole as a pale brown solid (1.56 g), m.p. 88°-92° C.

Boron tribromide (1.5 ml) was added dropwise to a mixture of the product so obtained (1.56 g) and methylene chloride (20 ml) which had been cooled to −70° C. The mixture was allowed to warm to ambient temperature and was stirred for 2 hours. A saturated aqueous sodium bicarbonate solution was added carefully until there was no further effervescence and the mixture was extracted with methylene chloride (3×30 ml). The combined extracts were washed with water and with a saturated aqueous sodium chloride solution, dried ($MgSO_4$) and evaporated to give 2-[1-hydroxy-1-(3-hydroxyphenyl)-2,2,2-trifluoroethyl]thiazole as a yellow solid (0.74 g), m.p. 133°-135° C. (recrystallised from a mixture of petroleum ether (b.p. 60°-80° C.) and ethyl acetate).

The product so obtained was reacted with 2-bromomethylnaphthalene using the procedure described in Example 1 except that the product was purified by column chromatography using a 4:1 v/v mixture of toluene and ethyl acetate as eluent. There was thus obtained the required starting material in 58% yield, m.p. 94°-96° C. (recrystallised from a mixture of petroleum ether (b.p. 60°-80° C.) and ethyl acetate).

c. The product was purified by column chromatography using a 19:1 v/v mixture of toluene and ethyl acetate as eluent. The 2-[1-hydroxy-1-(3-(naphth-2-ylmethoxy)phenyl)butyl]thiazole used as a starting material was obtained as follows:

The procedure described in the first two paragraphs of the portion of Example 1 which is concerned with the preparation of starting materials was repeated except that 1-bromopropane was used in place of bromoethane. There was thus obtained 3-hydroxybutyrophenone in 75% yield over the two stages. The product so obtained was reacted with 2-bromomethylnaphthalene using the procedure described in Example 1 except that the product was purified by column chromatography using a 1:2 v/v mixture of petroleum ether (b.p. 60°-80° C.) and toluene as eluent. There was thus obtained 3-(naphth-2-ylmethoxy)butyrophenone in 80% yield, m.p. 49°-51° C.

The product so obtained was reacted with thiazol-2-yl-lithium using the procedure described in the 4th paragraph of the portion of Example 1 which is concerned with the preparation of starting materials except that the product was purified by column chromatography using a 11:1 v/v mixture of toluene and ethyl acetate as eluent. There was thus obtained the required starting material in 85% yield, m.p. 102°–103° C.

d. The 2-[1-hydroxy-1-(3-(naphth-2-ylmethoxy)-phenyl)-3-trimethylsiliylprop-2-ynyl]thiazole used as a starting material was obtained as follows:

3-(Naphth-2-ylmethoxy)benzaldehyde was reacted with lithium trimethylsilylacetylide using the reaction conditions described in the 4th paragraph of the portion of Example 1 which is concerned with the preparation of starting materials except that the reaction was carried out at −40° C. rather than at −70° C. to give 1-(3-naphth-2-ylmethoxy)phenyl-3-trimethylsilylprop-2-ynyl alcohol in 90% yield.

The product so obtained was oxidised with Jones reagent using the reaction conditions described in *Helv. Chim. Acta.*, 1969, 69, 560 to give the corresponding ketone in 80% yield. The ketone so obtained was reacted with thiazol-2-yl-lithium using the procedure described in the 4th paragraph of the portion of Example 1 which is concerned with the preparation of starting materials to give the required starting material in 65% yield, m.p. 98° C.

e. This thiazole was obtained by alkylation of the preceding thiazole [Example 9, Compound No. 4] using the following procedure:

n-Butyl-lithium (1.5M in hexane, 0.92 ml) was added to a solution of 2-[1-methoxy-1-(3-(naphth-2-ylmethoxy)phenyl)prop-2-ynyl]thiazole (0.53 g) in tetrahydrofuran (6 ml) which had been cooled to −78° C. and the mixture was stirred for 10 minutes. Methyl iodide (0.087 ml) was added, the mixture was allowed to warm to ambient temperature and then the mixture was heated to 40° C. for 1 hour. The mixture was poured into a saturated aqueous ammonium chloride solution which had been cooled to 0° C. and the mixture was extracted with diethyl ether. The organic layer was dried (MgSO$_4$) and evaporated. The residue was purified by column chromatography using methylene chloride as eluent to give the required product (0.28 g) in 53% yield, m.p. 108°–110° C.

f. The 2-[1-hydroxy-1-(3-(naphth-2-ylmethoxy)-phenyl)prop-2-enyl]thiazole used as a starting material was obtained as follows:

Jones reagent (0.54 ml) was added to a mixture of 2-[3-(naphth-2-ylmethoxy)-α-hydroxybenzyl]thiazole (0.625 g; Note a. above) and acetone (70 ml) which had been cooled to 0° C. and the mixture was stirred at this temperature for 1 hour. Isopropanol (3.8 ml) was added and the mixture was evaporated. The residue was purified by column chromatography using methylene chloride as eluent. There was thus obtained 3-(naphth-2-ylmethoxy)phenyl 2-thiazolyl ketone (0.488 g) in 78% yield, m.p. 94°–95° C.

After repetition of the above described reaction steps vinylmagnesium bromide [prepared by adding a solution of vinyl bromide (1.8 g) in tetrahydrofuran (10 ml) to magnesium turnings (0.38 g)] was added to a mixture of the ketone so obtained (2.1 g), tetrahydrofuran (24 ml) and diethyl ether (36 ml). The mixture was heated to 60° C. for 90 minutes. The mixture was cooled to ambient temperature and partitioned between diethyl ether and a saturated aqueous ammonium chloride solution. The organic layer was dried (MgSO$_4$) and evaporated. The residue was purified by column chromatography using methylene chloride as eluent. There was thus obtained the required starting material (1.66 g) in 74% yield, m.p. 79°–81° C. (recrystallised from a mixture of pentane and diethyl ether).

g. 1,4,7,10,13-Pentaoxacyclopentadecane (15-crown-5; 0.2 equivalents) was used as an additional reagent within the reaction mixture. The reaction duration was 48 hours.

The 2-[1,2-dihydroxy-1-(3-(naphth-2-ylmethoxy)-phenyl)ethyl]thiazole used as a starting material was obtained as follows:

A solution of 3-(naphth-2-ylmethoxy)phenyl 2-thiazolyl ketone (4.84 g; Note f. above) in tetrahydrofuran (5 ml) was added dropwise to a solution of isopropoxydimethylsilylmethylmagnesium chloride [prepared as described in *J. Org. Chem.*, 1983, 48, 2120 from chloromethylisopropoxydimethylsilane (4.2 g) and magnesium powder (0.6 g) in tetrahydrofuran (7 ml)]. The mixture was stirred at ambient temperature for 1 hour, washed with saturated aqueous solution of ammonium chloride and then with a saturated aqueous solution of sodium chloride. The organic layer was separated, dried (Na$_2$SO$_4$) and evaporated to give 2-[1-hydroxy-2-isopropoxydimethylsilyl-1-(3-(naphth-2-ylmethoxy)phenyl)ethyl]thiazole as an oil.

A mixture of the product so obtained, sodium bicarbonate (1.22 g), hydrogen peroxide (13 ml, 30% w/v in water), methanol (40 ml) and tetrahydrofuran (40 ml) was heated to reflux for 1 hour. The mixture was evaporated to remove the organic solvents and the residue was extracted with methylene chloride. The organic layer was separated, washed with a saturated aqueous solution of sodium chloride, dried (MgSO$_4$) and evaporated. The residue was purified by column chromatography using a 9:1 v/v mixture of methylene chloride and acetone as eluent. There was so obtained the required starting material (3.36 g) in 64% yield, m.p. 100° C. (decomposes).

h. 2-[2-(Tert-butyldimethylsilyloxy)-1-hydroxy-1-(3-(naphth-2-ylmethoxy)phenyl)ethyl]thiazole used as the starting material was obtained as follows:

2-[1,2-Dihydroxy-1-(3-naphth-2-ylmethoxy)phenyl)ethyl]thiazole (2.4 g; Note g. above) was reacted at ambient temperature with tert-butyldimethylsilyl chloride (1.15 g) in the presence of imidazole (1.08 g) and dimethylformamide (15 ml). The mixture was stirred for 15 hours and then partitioned between methylene chloride and water. The organic layer was washed with a saturated aqueous sodium chloride solution, dried (MgSO$_4$) and evaporated to give the required starting material as an oil (3.2 g) in 100% yield.

After the methylation reaction which was carried out by following the procedure of Example 3 a mixture of the product so obtained as an oil (2.8 g) in 85% yield, tetra-n-butylammonium fluoride (1M solution in tetrahydrofuran, 16 ml) and tetrahydrofuran (5 ml) was stirred at ambient temperature for 2 hours. The mixture was evaporated and the residue was partitioned between ethyl acetate and water. The organic layer was washed with a saturated aqueous sodium chloride solution, dried (MgSO$_4$) and evaporated. The residue was purified by column chromatography using a 19:1 v/v mixture of methylene chloride and acetone as eluent. There was thus obtained 2-[2-hydroxy-1-methoxy-1-(naphth-2-ylmethoxy)phenyl)ethyl]thiazole (1.59 g) in 74% yield, m.p. 131°–132° C.

i. 1-Bromo-2-fluoroethane, used as the appropriate alkylating agent, was added in two portions; a first portion of 2 equivalents and a second portion of 2 equivalents added after 3 hours. The total reaction duration was 21 hours.

The 2-[1-hydroxy-1-(3-(naphth-2-ylmethoxy)phenyl)ethyl]thiazole used as a starting material was obtained by the reaction of 3-(naphth-2-ylmethoxy)acetophenone with 2-thiazolyl-lithium using the conditions described in the 4th paragraph of the portion of Example 1 which is concerned with the preparation of starting materials except that the reaction mixture was allowed to warm only to 0° C. There was thus obtained the required starting material in 79% yield, m.p. 114°–115° C.

The 3-(naphth-2-ylmethoxy)acetophenone used as a starting material immediately above was obtained by the reaction of 2-bromomethylnaphthalene and 3-hydroxyacetophenone using the conditions described in Example 1. There was thus obtained the required starting material in 66% yield, m.p. 89°–90° C.

j. 1-Bromo-2,2-difluoroethane was used as the appropriate alkylating agent and the conditions described in Note i. above were followed.

k. The 2-[1-hydroxy-1-[2-methoxy-3-(naphth-2-ylmethoxy)phenyl]propyl]thiazole used as a starting material was obtained as follows:

2-Bromomethylnaphthalene was reacted with 2-allyloxy-3-hydroxybenzaldehyde using the conditions described in Example 1 to give 2-allyloxy-3-(naphth-2-ylmethoxy)benzaldehyde as an oil in 95% yield. A mixture of the product so obtained (1.3 g), p-toluenethiol (0.8 g), sodium hydride (55% w/w dispersion in oil, 0.28 g) and dimethylformamide (10 ml) was heated to 100° C. for 1.3 hours. The mixture was partitioned between ethyl acetate and water. The organic layer was washed with water, dried (MgSO4) and evaporated. The residue was purified by column chromatography using a 4:1 v/v mixture of methylene chloride and ethyl acetate as eluent. There was thus obtained 2-hydroxy-3-(naphth-2-ylmethoxy)benzaldehyde (0.7 g), m.p. 105° C.

The product so obtained was methylated using the procedure described in Example 1 to give 2-methoxy-3-(naphth-2-ylmethoxy)benzaldehyde as an oil (0.66 g), in 90% yield. The product so obtained was reacted with thiazol-2-yl-lithium using the procedure described in the 4th paragraph of the portion of Example 1 which is concerned with the preparation of starting materials. There was thus obtained 2-[2-methoxy-3-(naphth-2-ylmethoxy)-α-hydroxybenzyl]thiazole as an oil (0.29 g), in 35% yield.

The above reactions were repeated and a solution of sodium dichromate (0.35 g) in water (2 ml) was added to a mixture of the product so obtained (0.4 g), tetra-n-butylammonium hydrogen sulphate (10 mg), glacial acetic acid (1 ml) and methylene chloride (10 ml). The mixture was stirred at ambient temperaure for 16 hours. The mixture was partitioned between methylene chloride and water. The organic layer was washed with water, dried (MgSO4) and evaporated. The residue was purified by column chromatography using methylene chloride as eluent to give 2-methoxy-3-(naphth-2-ylmethoxy)phenyl 2-thiazolyl ketone (0.3 g) in 75% yield, m.p. 100° C.

The product so obtained was reacted with ethylmagnesium iodide using the procedure described in the 4th paragraph of the portion of Example 3 which is concerned with starting materials. There was thus obtained the required starting material as a gum in 36% yield.

NMR Spectrum (CDCl3 δ values) 1.0 (t, 3H), 2.4 (m, 2H), 3.5 (s, 3H), 5.2 (s, 2H), 5.7 (s, 1H), 7.0–7.2 (m, 3H), 7.25 (d, 1H), 7.5 (m, 3H), 7.7 (d, 1H), 7.8–7.9 (m, 4H).

l. The product was purified by column chromatography using a 19:1 v/v mixture of toluene and ethyl acetate as eluent.

The 2-[1-hydroxy-1-(2-methyl-3-(naphth-2-ylmethoxy)phenyl)ethyl]thiazole used as a starting material was obtained as follows:

2-Bromomethylnaphthalene was reacted with methyl 3-hydroxy-2-methylbenzoate (Tetrahedron, 1969, 25, 4249) using the conditions described in Example 1 to give methyl 2-methyl-3-(naphth-2-ylmethoxy)benzoate in 92% yield, m.p. 47°–48° C. (recrystallised from a mixture of diethyl ether and pentane). The product so obtained was reacted with thiazol-2-yl-lithium using the procedure described in the 3rd paragraph of the portion of Example 3 which is concerned with the preparation of starting materials to give, after purification of the product by column chromatography using a 49:1 v/v mixture of toluene and ethyl acetate as eluent, 3-(naphth-2-ylmethoxy)-2-methylphenyl 2-thiazolyl ketone as an oil in 72% yield.

Methyl-lithium (1.4M in diethyl ether, 3.25 ml) was added to a solution of the product so obtained (1.42 g) in tetrahydrofuran (15 ml) and the mixture was stirred at ambient temperature for 10 minutes. The mixture was partitioned between ethyl acetate and a saturated aqueous ammonium chloride solution. The organic layer was dried (MgSO4) and evaporated. The residue was purified by column chromatography using a 17:3 v/v mixture of toluene and ethyl acetate as eluent. There was thus obtained the required starting material as an oil (1.03 g).

m. The 2-[1-hydroxy-1-(4-methoxy-3-(naphth-2-ylmethoxy)phenyl)propyl]thiazole used as a starting material was obtained as follows:

2-Bromomethylnaphthalene was reacted with 3-hydroxy-4-methoxybenzaldehyde using the conditions described in Example 1 to give 4-methoxy-3-(naphth-2-ylmethoxy)benzaldehyde in 50% yield, m.p. 80° C. Following the procedure described in Note k. above the product so obtained was reacted with thiazol-2-yl-lithium to give 2-[4-methoxy-3-(naphth-2-ylmethoxy)-α-hydroxybenzyl]thiazole as an oil in 62% yield; that product was oxidised with sodium dichromate to give 4-methoxy-3-(naphth-2-ylmethoxy)phenyl 2-thiazolyl ketone in 58% yield, m.p. 149°–150° C.; and the product so obtained was reacted with ethylmagnesium iodide to give the required starting material in 45% yield, m.p. 80° C.

n. Prop-2-ynyl bromide was used as the alkylating agent. The product gave the following NMR spectrum: (CDCl3, δ values) 0.82 (t, 3H), 2.4 (t, 1H), 2.5 (m, 2H), 3.76 (s, 3H), 4.0 (d, 2H), 5.16 (s, 2H), 6.48 (t, 1H), 6.68 (t, 1H), 6.76 (t, 1H), 7.25 (d, 1H), 7.45–7.55 (m, 3H), 7.67 (d, 1H), 7.8–7.9 (m, 4H).

o. Ethyl bromoacetate was used as the alkylating agent and the reaction duration was 48 hours. The product was purified by column chromatography using increasingly polar mixtures of petroleum ether (b.p. 60°–80° C.) and ethyl acetate as eluent. The product gave the following NMR spectrum: (CDCl3 δ values) 0.8 (t, 3H), 1.26 (t, 3H), 2.37 (m, 1H), 2.7 (m, 1H), 3.77 (s, 3H), 3.97 (s, 2H), 4.2 (q, 2H), 5.18 (s, 2H), 6.48 (t, 1H), 6.74 (t, 1H), 6.82 (t, 1H), 7.24 (d, 1H), 7.46–7.56 (m, 3H), 7.68 (d, 1H), 7.8–7.9 (m, 4H).

p. An equimolar mixture of chloromethyl methyl sulphide and sodium iodide was used to provide the alkylating agent. The reaction duration was 18 hours and the product was purified by column chromatography using increasingly polar mixtures of petroleum ether (b.p. 60°-80° C.) and ethyl acetate as eluent. The product gave the following NMR spectrum: (CDCl₃ δ values) 0.8 (t, 3H), 2.23 (s, 3H), 2.43 (m, 1H), 2.67 (m, 1H), 3.75 (s, 3H), 4.4 (s, 2H), 5.17 (s, 2H), 6.49 (t, 1H), 6.67 (t, 1H), 6.75 (t, 1H), 7.24 (d, 1H), 7.45-7.55 (m, 3H), 7.68 (d, 1H), 7.8-7.9 (m, 4H).

q. The product was purified by column chromatography using methylene chloride as eluent and it gave the following NMR spectrum: (CDCl₃, δ values) 1.9 (t, 1H), 3.3-3.6 (q, 2H), 3.35 (s, 3H), 3.75 (s, 3H), 5.17 (s, 2H), 6.5 (t, 1H), 6.65 (t, 1H) 6.75 (t, 1H) 7.25 (d, 1H), 7.45-7.55 (m, 3H), 7.67 (d, 1H), 7.8-7.86 (m, 4H).

The 2-[1-hydroxy-1-(3-methoxy-5-(naphth-2-ylmethoxy)phenyl)but-3-ynyl]thiazole used as a starting material was obtained as follows:

A solution of prop-2-ynyl bromide (8.4 ml of an 80% w/v solution in toluene) in diethyl ether (50 ml) was added dropwise to a suspension of a mixture of magnesium turnings (1.8 g) and mercuric chloride (0.1 g) in diethyl ether (20 ml). The mixture was heated to reflux until all of the magnesium had been consumed. A solution of 3-methoxy-5-(naphth-2-ylmethoxy)phenyl 2-thiazolyl ketone (0.5 g) in tetrahydrofuran (10 ml) was added dropwise and the mixture was maintained at reflux temperature for 30 minutes. The mixture was poured into a saturated aqueous ammonium chloride solution and extracted with ethyl acetate (3×50 ml). The combined extracts were washed with water and with a saturated aqueous sodium chloride solution, dried (MgSO₄) and evaporated. The residue was purified by column chromatography using methylene chloride as eluent. There was thus obtained the required starting material as a gum (0.3 g) in 54% yield.

NMR Spectrum (CDCl₃, δ values, major characterising signals) 2.05 (t, 1H), 3.1-3.5 (q, 2H), 3.8 (s, 4H), 5.25 (s, 2H).

r. n-Butyl-lithium (1.6M in hexane, 1.67 ml) was added dropwise to a solution of 2-[2-cyano-1-hydroxy-1-(5-methoxy-3-(naphth-2-ylmethoxy)phenyl)ethyl]-thiazole (2.1 g) in tetrahydrofuran (20 ml) which had been cooled to −75° C. The mixture was stirred at −75° C. for 1 hour. Methyl trifluoroacetate (0.35 ml) was added and the mixture was stirred at −75° C. for 2 hours. The mixture was poured into a saturated aqueous ammonium chloride solution and extracted with ethyl acetate (3×50 ml). The combined extracts were washed with water, with a saturated aqueous sodium chloride solution, dried (MgSO₄) and evaporated. The residue was purified by column chromatography using a 19:1 v/v mixture of methylene chloride and ethyl acetate as eluent. There was thus obtained 2-[2-cyano-1-methoxy-1-(5-methoxy-3-(naphth-2-ylmethoxy)phenyl)ethyl]-thiazole as an oil (0.42 g) in 37% yield.

NMR Spectrum (CDCl₃, δ values) 3.35 (s, 3H), 3.4-3.75 (q, 2H), 3.78 (s, 3H), 5.15 (s, 2H), 6.5 (t, 1H), 6.6 (t, 1H), 6.66 (t, 1H), 7.3 (d, 1H), 7.5 (m, 3H), 7.7 (d, 1H), 7.8 (m, 4H).

The 2-[2-cyano-1-hydroxy-1-(5-methoxy-3-(naphth-2-ylmethoxy)phenyl)ethyl]thiazole used as a starting material was obtained as follows:

Acetonitrile (0.84 ml) was added dropwise to a mixture of n-butyl-lithium (1.6M in hexane, 5.2 ml) and tetrahydrofuran (10 ml) which had been cooled to −78° C. The mixture was stirred at −78° C. for 45 minutes and a solution of 3-methoxy-5-(naphth-2-ylmethoxy)-phenyl 2-thiazolyl ketone (2.1 g) in tetrahydrofuran (10 ml) was added dropwise. The mixture was allowed to warm to ambient temperature and was stirred for 30 minutes. The mixture was partitioned between water and ethyl acetate. The organic layer was washed with water, dried (MgSO₄) and evaporated. The residue was purified by column chromatography using a 10:1 v/v mixture of methylene chloride and ethyl acetate as eluent. There was thus obtained the required starting material as an oil (1.1 g) in 48% yield.

s. The 2-[1-(5-allyloxy-3-(naphth-2-ylmethoxy)-phenyl)-1-hydroxypropyl]thiazole used as a starting material was prepared used as follows:

Ethyl 3,5-dihydroxybenzoate was reacted in turn with 2-bromomethylnaphthalene and allyl bromide using the conditions described in Example 1 to give ethyl 5-allyloxy-3-(naphth-2-ylmethoxy)benzoate in 15% yield, as an oil. Following the procedures described in the portion of Example 3 which is concerned with the preparation of starting materials the product so obtained was reacted with thiazol-2-yl-lithium to give 5-allyloxy-3-(naphth-2-ylmethoxy)phenyl 2-thiazolyl ketone in 52% yield, m.p. 65°-67° C., and that product was reacted with ethylmagnesium to give the required starting material in 49% yield, as a gum.

t. The product was obtained by the removal of the tert-butyldimethylsilyl group from 2-[1-(5-tert-butyldimethylsilyloxy-3-(naphth-2-ylmethoxy)phenyl-1-methoxypropyl]thiazole using the conditions described in the 4th paragraph of the portion of Example 6 which is concerned with the preparation of starting materials. There was thus obtained the corresponding 5-hydroxy-substituted thiazole as an oil in 78% yield. The product gave the following NMR spectrum: (CDCl₃, δ values) 0.75 (t, 3H), 2.4 (m, 1H), 2.7 (m, 1H), 3.2 (s, 3H), 5.15 (s, 2H), 6.4 (t, 1H), 6.6 (t, 1H), 6.7 (t, 1H), 7.25 (d, 1H), 7.5 (m, 3H), 7.65 (d, 1H), 7.8 (m, 4H).

The 2-[1-(5-tert-butyldimethylsilyloxy-3-(naphth-2-ylmethoxy)phenyl)-1-hydroxypropyl]thiazole used as the starting material for the methylation reaction was obtained as follows:

Ethyl 5-hydroxy-3-(naphth-2-ylmethoxy)benzoate, obtained from ethyl 3,5-dihydroxybenzoate and 2-bromomethylnaphthalene, was reacted with tert-butyldimethylsilyl chloride using the conditions described in the 1st paragraph of the portion of Example 6 which is concerned with the preparation of starting materials and the product so obtained was reacted in turn with thiazol-2-yl-lithium and ethylmagnesium iodide following the procedures described in the portion of Example 3 which is concerned with the preparation of starting materials. There was thus obtained the required starting material in 49% yield (from ethyl 5-hydroxy-3-(naphth-2-ylmethoxy)benzoate) as an oil. This starting material was methylated using the procedure described in Example 3 to give 2-[1-(5-tert-butyldimethylsilyloxy-3-(naphth-2-ylmethoxy)phenyl)-1-methoxypropyl]-thiazole as an oil, in 42% yield.

u. The product was purified by column chromatography using a 4:1 v/v mixture of petroleum ether (b.p. 60°-80° C.) and ethyl acetate as eluent and recrystallised from a mixture of ethyl acetate and methanol.

The 2-[1-hydroxy-1-(3-(naphth-2-ylmethoxy)-5-nitrophenyl)propyl]thiazole used as a starting material was obtained as follows:

A mixture of 1,3-dinitrobenzene (125 g), iodine (97 g) and concentrated sulphuric acid (500 ml) was heated to 140° C. for 3.5 hours. The mixture was cooled, poured onto crushed ice and filtered. The solid was washed with water and dried to give 3,5-dinitroiodobenzene (194 g) in 89% yield, m.p. 101°-102° C.

Sodium hydride (50% w/w dispersion in oil, 4.8 g) was added portionwise to a solution of 2-naphthylmethanol (15.8 g) in dimethylacetamide (500 ml) and the mixture was stirred at ambient temperature for 1 hour. 3,5-Dinitroiodobenzene (29.4 g) was added portionwise and the mixture was stirred at ambient temperature for 48 hours. The mixture was evaporated and the residue was partitioned between methylene chloride and water. The organic layer was washed with water and with a saturated aqueous sodium chloride solution, dried (MgSO$_4$) and evaporated. The residue was purified by column chromatography using a 9:1 v/v mixture of petroleum ether (b.p. 60°-80° C.) and ethyl acetate as eluent. There was thus obtained 3-(naphth-2-ylmethoxy)-5-nitroiodobenzene (28 g) in 69% yield, m.p. 114°-116° C.

A solution of the product so obtained (4 g) in tetrahydrofuran (120 ml) was cooled to −100° C. and n-butyllithium (1.6M in hexane, 6.3 ml) was added dropwise such that the mixture did not warm above −98° C. The mixture was stirred at −100° C. for 1 hour and a solution of ethyl 2-thiazolyl ketone (1.4 g) in tetrahydrofuran (10 ml) was added dropwise such that the mixture did not warm above −98° C. The mixture was stirred at −100° C. for 40 minutes. The mixture was acidified by the addition of a saturated solution of hydrogen chloride in diethyl ether and the mixture was allowed to warm to ambient temperature. The mixture was evaporated and the residue was partitioned between methylene chloride and water. The organic phase was washed with water, dried (MgSO$_4$) and evaporated. The residue was purified by column chromatography using a 4:1 v/v mixture of petroleum ether (b.p. 60°-80° C.) and ethyl acetate as eluent. There was thus obtained the required starting material as an oil (2 g) in 48% yield.

NMR Spectrum (CD$_3$SOCD$_3$, δ values) 0.66 (t, 3H), 2.48 (m, 1H), 2.60 (m, 1H), 3.18 (s, 3H), 5.40 (s, 2H), 7.47 (m, 1H), 7.47 (m, 1H), 7.54 (d, 1H), 7.54 (m, 1H), 7.58 (doublet of doublets, 1H) 7.69 (d, 1H), 7.74 (d, 1H), 7.82 (m, 2H), 7.90 (m, 3H), 8.01 (s, 1H).

v. The 2-[1-(5-fluoro-3-(naphth-2-ylmethoxy)-phenyl)-1-hydroxypropyl]thiazole used as a starting material was obtained as follows:

Sodium hydride (50% w/w dispersion in oil, 0.96 g) was added portionwise to a solution of 2-naphthylmethanol (3.16 g) in dimethylacetamide (80 ml) and the mixture was stirred at ambient temperature for 30 minutes. A solution of 3,5-difluorobenzonitrile (2.78 g) in dimethylacetamide (20 ml) was added and the mixture was stirred at ambient temperature for 30 minutes. The mixture was evaporated and the residue was partitioned between methylene chloride and water. The organic phase was washed with a saturated aqueous sodium chloride solution, dried (MgSO$_4$) and evaporated. The residue was purified by column chromatography using a 4:1 v/v mixture of petroleum ether (b.p. 60°-80° C.) and ethyl acetate as eluent. There was thus obtained 5-fluoro-3-(naphth-2-ylmethoxy)benzonitrile (5.1 g) in 92% yield, m.p. 90°-91° C.

A solution of the product so obtained (1.39 g) in tetrahydrofuran (10 ml) was added dropwise to a solution of thiazol-2-yl-lithium [prepared by adding 2-bromothiazole (1.64 g) in diethyl ether (10 ml) to a mixture of n-butyl-lithium (1.6M in hexane, 6.66 ml) and diethyl ether (10 ml) which had been cooled to −75° C.] such that the mixture did not warm above −70° C. The mixture was stirred at −75° C. for 30 minutes then acidified by the addition of a saturated solution of hydrogen chloride in diethyl ether. The mixture was allowed to warm to ambient temperature and was partitioned between methylene chloride and water. The organic phase was washed with a saturated aqueous sodium chloride solution, dried (MgSO$_4$) and evaporated. There was thus obtained 5-fluoro-3-(naphth-2-ylmethoxy)phenyl 2-thiazolyl ketone (1.97 g) in 54% yield, m.p. 118°-119° C. (recrystallised from ethanol).

A portion (1.45 g) of the product so obtained was reacted with ethylmagnesium iodide using the procedure described in the 4th paragraph of the portion of Example 3 which is concerned with the preparation of starting materials. There was thus obtained the required starting material (0.8 g) in 57% yield, m.p. 117°-118° C.

w. The product was purified by column chromatography using a 2:1 v/v mixture of methylene chloride and hexane as eluent. The product gave the following NMR spectrum (CDCl$_3$, δ values) 0.75 (t, 3H), 2.4 (m, 1H), 2.7 (m, 1H), 3.2 (s, 3H), 5.2 (s, 2H), 7.15 (t, 1H), 7.25 (d, 1H), 7.3 (t, 1H), 7.4 (t, 1H), 7.5 (m, 3H), 7.7 (d, 1H), 7.8-7.9 (m, 4H).

The 2-[1-hydroxy-1-(3-(naphth-2-ylmethoxy)-5-trifluoromethylphenyl)propyl]thiazole used as a starting material was obtained as follows:

Using conventional procedures 3-methoxy-5-trifluoromethylaniline (*J. Chem. Soc.*, 1951, 2013) was diazotised and reacted with potassium iodide to give 3-methoxy-5-trifluoromethyliodobenzene, as an oil. The product so obtained was reacted with boro tribromide using the conditions described in Note b. above to give 3-hydroxy-5-trifluoromethyliodobenzene in 95% yield, as an oil. The product so obtained was reacted with 2-bromomethylnaphthalene using the conditions described in Example 1 to give 3-(naphth-2-ylmethoxy)-5-trifluoromethyliodobenzene in 62% yield, m.p. 65°-66° C.

The product so obtained was reacted with ethyl 2-thiazolyl ketone using the conditions described in Note u. above to give the required starting material as an oil in 43% yield.

NMR Spectrum (CDCl$_3$, δ values) 0.9 (t, 3H), 2.3-2.5 (m, 2H), 3.6 (s, 1H), 5.25 (s, 2H), 7.15 (s, 1H), 7.25 (d, 1H), 7.5 (m, 5H), 7.7 (d, 1H), 7.8-8.0 (m, 4H).

x. The product gave the following NMR spectrum: (CDCl$_3$, δ values) 0.7 (t, 3H), 1.2 (t, 3H), 2.4 (m, 1H), 2.65 (m, 1H), 3.2-3.4 (q, 2H), 5.2 (s, 2H), 7.1 (t, 1H), 7.2 (d, 1H), 7.3 (t, 1H), 7.4 (t, 1H), 7.5 (m, 3H), 7.65 (d, 1H), 7.8-7.9 (m, 4H).

y. The 2-[1-hydroxy-1-(3-methoxy-4-(naphth-2-ylmethoxy)phenyl)propyl]thiazole used as a starting material was obtained as follows:

2-Bromomethylnaphthalene was reacted with ethyl vanillate using the conditions described in Example 1 to give ethyl 3-methoxy-4-(naphth-2-ylmethoxy)benzoate in 54% yield, m.p. 86°-87° C. Following the procedures described in the portion of Example 6 which is concerned with the preparation of starting materials the product so obtained was reacted with thiazol-2-yl-lithium and the resultant product was reacted with ethylmagnesium iodide to give the required starting material as an oil in 20% yield, m.p. 124°-126° C. (recrystallised from a mixture of hexane and ethyl acetate).

z. The product was obtained by the removal of the tert-butyldimethylsilyl group from 2-[1-(3-tert-butyldimethylsilyloxy-4-(naphth-2-ylmethoxy)phenyl)-1-methoxypropyl]thiazole using the conditions described in the 4th paragraph of the portion of Example 6 which is concerned with the preparation of starting materials. There was thus obtained the corresponding 3-hydroxy-substituted thiazole in 64% yield, m.p. 131°–132° C.

The 2-[1-(3-tert-butyldimethylsilyloxy.4-(naphth-2-ylmethoxy)phenyl)-1-hydroxypropyl]thiazole used as the starting material for the methylation reaction was obtained as follows:

Ethyl 3-hydroxy-4-(naphth-2-ylmethoxy)benzoate, m.p. 155°–157° C., obtained in 51% yield from ethyl 3,4-dihydroxybenzoate and 2-bromomethylnaphthalene, was reacted with tert-butyldimethylsilyl chloride using the conditions described in the 1st paragraph of the portion of Example 6 which is concerned with the preparation of starting materials and the product so obtained was reacted with thiazol-2-yl-lithium following the procedure described in the portion of Example 3 which is concerned with the preparation of starting materials to give 3-tert-butyldimethylsilyloxy-4-(naphth-2-ylmethoxy)phenyl 2-thiazolyl ketone, m.p. 97°–99° C., in 19% yield from ethyl 3-hydroxy-4-(naphth-2-ylmethoxy)benzoate. The product so obtained was reacted with ethylmagnesium iodide following the procedure described in the portion of Example 3 which is concerned with the preparation of starting materials to give the required starting material in 99% yield as an oil.

This starting material was methylated using the procedure described in Example 3 to give 2-[1-(3-(tert-butyldimethylsilyloxy)-4-(naphth-2-ylmethoxy)-phenyl)-1-methoxypropyl]thiazole as an oil, in 76% yield.

aa. The 2-[1-(3-cyano-4-(naphth-2-ylmethoxy)-phenyl)-1-hydroxypropyl]thiazole used as a starting material was obtained as follows:

2-Bromomethylnaphthalene was reacted with methyl 5-iodosalicylate using the procedure described in Example 1 to give methyl 5-iodo-2-(naphth-2-ylmethoxy)benzoate in 68% yield. Using conventional procedures the ester was hydrolysed with base to give the corresponding acid, the acid chloride was prepared by reaction with thionyl chloride and the acid chloride was reacted with ethanolic ammonia to give 5-iodo-2-(naphth-2-ylmethoxy)benzamide in 84% yield from the ester, m.p. 163° C. The benzamide was converted to the corresponding benzonitrile in 72% yield, m.p. 108°–110° C., using the conditions described below in Example 27.

The product so obtained was reacted with ethyl 2-thiazolyl ketone using the conditions described in Note u. above to give the required starting material in 82% yield, m.p. 131°–134° C. (recrystallised from a mixture of methylene chloride and ethyl acetate).

bb. The 2-[1-(3-tert-butoxycarbonyl-4-(naphth-2-ylmethoxy)phenyl)-1-hydroxypropyl]thiazole used as a starting material was obtained as follows:

A mixture of 5-iodosalicylic acid (10 g), N,N-dimethylformamide di-tert-butyl acetal (31 g) and toluene (50 ml) was heated to 85° C. for 30 minutes. The mixture was evaporated and the residue was partitioned between ethyl acetate and a saturated aqueous sodium bicarbonate solution. The organic phase was washed with water, dried (MgSO$_4$) and evaporated to give tert-butyl 5-iodosalicylate as a solid (9 g). The product so obtained was reacted with 2-bromomethylnaphthalene using the procedure described in Example 1 to give tert-butyl 5-iodo-2-(naphth-2-ylmethoxy)benzoate in 44% yield, m.p. 90° C.

The product so obtained was reacted with ethyl 2-thiazolyl ketone using the conditions described in Note u. above to give the required starting material as an oil in 25% yield. The material gave the following characteristic NMR signals: (CDCl$_3$, δ values) 0.9 (t, 3H), 1.5 (s, 9H), 2.3–2.5 (m, 2H), 3.5 (OH), 5.3 (s, 2H).

cc. The 2-[1-hydroxy-1-[5-(naphth-2-ylmethoxy)pyrid-3-yl]ethyl]thiazole used as a starting material was obtained as follows:

The procedure described in the 2nd paragraph of the portion of Example 4 which is concerned with the preparation of starting materials was repeated except that methyl 2-thiazolyl ketone was used in place of ethyl 2-thiazolyl ketone. There was thus obtained the required starting material in 67% yield, m.p. 151°–152° C.

dd. The 2-[1-(5-benzyloxypyrid-3-yl)-1-hydroxypropyl]thiazole used as a starting material was obtained as follows:

The procedure described in the portion of Example 4 which is concerned with the preparation of starting materials was repeated except that benzyl alcohol was used in place of 2-naphthylmethanol. There was thus obtained the required starting material as an oil, in 30% yield.

ee. The 2-[1-hydroxy-1-(5-((E)-cinnamyloxy)pyrid-3-yl)propyl]thiazole used as a starting material was obtained as follows:

The procedure described in the portion of Example 4 which is concerned with the preparation of starting materials was repeated except that (E)-cinnamyl alcohol was used in place of 2-naphthylmethanol. There was thus obtained the required starting material as an oil in 14% yield.

ff. The 2-[1-hydroxy-1-[6-(naphth-2-ylmethoxy)pyrid-2-yl]propyl]thiazole used as a starting material was obtained as follows:

The procedure described in the portion of Example 4 which is concerned with the preparation of starting materials was repeated except that 2,6-dibromopyridine was used in place of 3,5-dibromopyridine. There were thus obtained in turn 2-bromo-6-(naphth-2-ylmethoxy)-pyridine in quantitative yield, m.p. 67°–69° C., and the required starting material in 37% yield, m.p. 98°–100° C.

gg. The 2-[1-hydroxy-1-[4-(naphth-2-ylmethoxy)pyrid-2-yl]propyl]thiazole used as a starting material was obtained as follows:

2-Naphthylmethanol was reacted with 2-bromo-4-nitropyridine (Chem. Abstracts, 1951, 45, 9536) using the conditions described in the first paragraph of the portion of Example 4 which is concerned with the preparation of starting materials except that the reaction mixture was stirred at ambient temperature for 2 hours. There was thus obtained 2-bromo-4-(naphth-2-ylmethoxy)pyridine in 80% yield, m.p. 99°–100° C.

The product so obtained was reacted with ethyl 2-thiazolyl ketone using the conditions described in Example 4 to give an impure sample of the required starting material contaminated with 2-bromo-4-(naphth-2-ylmethoxy)pyridine. The mixture was used in the methylation reaction and the final product was purified by column chromatography.

hh. The 2-[1-hydroxy-1-[6-(naphth-2-ylmethoxy)pyrid-3-yl]propyl]thiazole used as a starting material was obtained as follows:

The procedure described in the portion of Example 4 which is concerned with the preparation of starting materials was repeated except that 2,5-dibromopyridine was used in place of 3,5-dibromopyridine. There were thus obtained in turn 5-bromo-2-(naphth-2-ylmethoxy)-pyridine in 72% yield, m.p. 83°-85° C., and the required starting material in 67% yield as an oil.

ii. The product gave the following NMR spectrum: (CDCl$_3$, δ values) 0.78 (t, 3H), 2.7 (q, 2H), 3.28 (s, 3H), 5.6(s, 2H), 7.24 (s, 1H), 7.32, (d, 1H), 7.46-7.58 (m, 3H), 7.77 (d, 1H), 7.8-7.95 (m, 4H), 8.79 (s, 1H), The 2-[1-hydroxy-1-[6-(naphth-2-ylmethoxy)pyrimidin-4-yl]propyl]thiazole used as a starting material was obtained as follows:

2-Naphthylmethanol was reacted with 4,6-diiodopyrimidine (*J. Med. Pharm. Chem.* 1962, 1335) using the conditions described in the first paragraph of the portion of Example 4 which is concerned with the preparation of starting materials except that the reaction mixture was stirred at ambient temperature for 2 hours. There was thus obtained 6-iodo-4-(naphth-2-ylmethoxy)pyrimidine as an oil in 39% yield.

The product so obtained was reacted with ethyl 2-thiazolyl ketone using the procedure described in Example 4 except that the lithiation step and addition of the above-mentioned ketone were conducted at −110° C. The mixture was stirred at −110° C. for 30 minutes and then allowed to warm to −20° C. The mixture was poured into a saturated aqueous ammonium chloride solution. The remaining procedure was as described in Example 4. There was thus obtained the required starting material as an oil in 42% yield.

jj. The product gave the following NMR data: (CDCl$_3$, δ values) 0.8 (t, 3H), 2.4 (m, 1H), 2.7 (m, 1H), 3.2 (s, 3H), 3.85 (s, 3H), 5.1 (s, 2H), 6.8 (d, 1H), 6.9 (d, 1H), 7.0 (d, 1H), 7.25 (d, 1H), 7.3-7.45 (m, 5H), 7.7 (d, 1H).

The 2-[1-(4-benzyloxy-3-methoxyphenyl)-1-hydroxypropyl]thiazole used as a starting material was obtained as follows:

Benzyl bromide was reacted with ethyl vanillate using the conditions described in Example 1 to give ethyl 4-benzyloxy-3-methoxybenzoate in 97% yield m.p. 72°-74° C. Following the procedures described in the portion of Example 6 which is concerned with the preparation of starting materials the product so obtained was reacted with thiazol-2-yl-lithium and the resultant product was reacted with ethylmagnesium iodide to give the required starting material as an oil in 20% yield.

kk. The product gave the following NMR data: (CDCl$_3$, δ values) 0.8 (t, 3H), 2.4 (m, 1H), 2.7 (m, 1H), 3.2 (s, 3H), 3.85 (s, 3H), 4.96 (s, 2H), 7.0 (m, 3H), 7.3 (m, 4H), 7.45 (m, 2H), 7.7 (d, 1H).

The 2-[1-(4-(3-phenylprop-2-ynyloxy)-3-methoxyphenyl)-1-hydroxypropyl]thiazole used as a starting material was obtained as follows:

3-Phenylprop-2-ynyl bromide was reacted with ethyl vanillate using the conditions described in Example 1 to give ethyl 4-(3-phenylprop-2-ynyloxy)-3-methoxybenzoate in 70% yield, m.p. 62°-65° C. Following the procedures described in the portion of Example 6 which is concerned with the preparation of starting materials the product so obtained was reacted with thiazol-2-yl-lithium and the resultant product was reacted with ethylmagnesium iodide to give the required starting material as an oil in 61% yield.

EXAMPLE 10

A solution of 2-[1-methoxy-1-(3-prop-2-ynyloxyphenyl)ethyl]thiazole (0.55 g) in acetonitrile (1 ml) was added in one portion to a stirred mixture of iodobenzene (0.23 ml), triethylamine (0.27 ml), bis(triphenylphosphine)palladium chloride (0.02 g), cuprous iodide (0.02 g) and acetonitrile (2.5 ml), the mixture was stirred at ambient temperature for 15 minutes, and then heated to 60° C. for 2.5 hours. The mixture was cooled to ambient temperature, poured into water (50 ml) and neutralised by the addition of dilute hydrochloric acid solution. The mixture was extracted with diethyl ether (2×50 ml). The combined extracts were washed with water, dried (MgSO$_4$) and evaporated. The residue was purified by column chromatography using increasingly polar mixtures of hexane and ethyl acetate as eluent. There was thus obtained 2-[1-methoxy-1-(3-(3-phenylprop-2-ynyloxy)phenyl)ethyl]thiazole (0.33 g, 47%) as an oil.

NMR Spectrum (CDCl$_3$, δ values) 2.05 (s, 3H), 3.3 (s, 3H), 4.9 (s, 2H), 7.3 (d, 1H, thiazole H), 7.7 (d, 1H, thiazole H), 6.9-7.4 (m, 9H).

The 2-[1-methoxy-1-(3-prop-2-ynyloxyphenyl)ethyl]thiazole used as a starting material was obtained as follows:

A mixture of 2-[1-(3-hydroxyphenyl)-1-methoxyethyl]thiazole (11.8 g), 2-propynyl bromide (80% w/v solution in toluene, 15 ml), potassium carbonate (13 g) and acetone (150 ml) was stirred and heated to reflux for 5 hours. The mixture was cooled to ambient temperature and filtered. The filtrate was evaporated and the residue was partitioned between diethyl ether and water. The organic layer was dried (MgSO$_4$) and evaporated to give the required starting material as an oil in 62% yield which was used without further purification.

EXAMPLE 11

Using a similar procedure to that described in Example 10 using the appropriate substituted-iodobenzene and 2-[1-methoxy-1-(3-prop-2-ynyloxyphenyl)propyl]thiazole in place of the corresponding 2-ethylthiazole there were obtained the compounds described in the following table:

TABLE V

Ar$^1$—C≡C—CH$_2$—O—[phenyl]—CH$_2$—[thiazole N/S]

| Ex. 11 Compd. No. | Ar$^1$ | Yield (%) | Note |
|---|---|---|---|
| 1 | o-tolyl | 29 | a. |
| 2 | m-tolyl | 36 | b. |
| 3 | 2-cyanophenyl | 43 | |
| 4 | 2-methoxyphenyl | 34 | c. |
| 5 | 3-methoxyphenyl | 29 | d. |
| 6 | 4-methoxyphenyl | 50 | e. |
| 7 | 2-fluorophenyl | 62 | |
| 8 | 3-fluorophenyl | 50 | |
| 9 | 4-fluorophenyl | 60 | |
| 10 | 1-naphthyl | 39 | f. |
| 11 | 2-aminophenyl | 19 | |
| 12 | 3-aminophenyl | 44 | |
| 13 | 4-aminophenyl | 31 | |
| 14 | 3-hydroxyphenyl | 43 | |
| 15 | 2-methylthiophenyl | 19 | g. |
| 16 | 2-methylsulphinylphenyl | 49 | h. |
| 17 | 2-methylsulphonylphenyl | 30 | i |
| 18 | 2-formylphenyl | 45 | j. |

TABLE V-continued

Ar¹—C≡C—CH₂—O—[phenyl]—CH₂—[thiazole with N, S]

| Ex. 11 Compd. No. | Ar¹ | Yield (%) | Note |
|---|---|---|---|
| 19 | 3-methoxycarbonylphenyl | 78 | k. |

Notes

The 2-[1-methoxy-1-(3-prop-2-ynyloxyphenyl)propyl]thiazole used as a starting material was obtained by the reaction of 2-propynyl bromide with 2-[1-(3-hydroxyphenyl)-1-methoxypropyl]thiazole using the conditions described in the portion of Example 10 which is concerned with the preparation of starting materials. The material was purified by column chromatography using a 1:1 v/v mixture of hexane and ethyl acetate as eluent. There was thus obtained the required starting material as an oil, in 94% yield.

The products were all obtained as oils which were characterized by way of their NMR spectral data and by mass spectral data. Full NMR spectral data is given below for Compound No. 1 of Example 11. Much of the corresponding data for the other compounds was very similar as expected, therefore only characteristic signals are given. All of the compounds were dissolved in CDCl₃ and chemical shift values are given on the δ scale.

a. 0.76 (t, 3H, CH₂$CH_3$), 2.32 (s, 3H, o-CH₃), 2.45 and 2.65 (2 m's, 2H, $CH_2$CH₃), 3.2 (s, 3H, OCH₃), 4.9 (s, 2H, CH₂O), 7.2 and 7.7 (2 d's, 2H, thiazole H's), 6.9–7.4 (m, 8H, aromatic).
b. 2.3 (s, 3H, m-CH₃).
c. 3.85 (s, 3H, o-OCH₃).
d. 3.80 (s, 3H, m-OCH₃).
e. 3.80 (s, 3H, p-OCH₃).
f. 6.9–8.2 (m's, 13H, aromatics).
g. 2.45 (s, 3H, SCH₃).
h. 2.55 (s, 3H, SOCH₃).
i. 3.0 (s, 3H, SO₂CH₃).
j. 10.4 (s, 1H, CHO).
k. 3.9 (s, 3H, CO₂CH₃).

EXAMPLE 12

A mixture of 2-[1-(3-(4-methylthiobenzyloxy)-phenyl)-1-methoxypropyl]thiazole (Example 5, Compound No. 7; 0.25 g), sodium metaperiodate (0.17 g), methanol (10 ml) and water (1 ml) was stirred at ambient temperature for 16 hours. A second portion of sodium metaperiodate (0.1 g) was added and the mixture was stirred for a further 24 hours. The mixture was partitioned between ethyl acetate and water. The organic layer was washed with a saturated aqueous sodium chloride solution, dried (MgSO₄) and evaporated. The residue was purified by column chromatography using ethyl acetate as eluent. There was thus obtained 2-[1-(3-(4-methylsulphinylbenzyloxy)phenyl)-1-methoxypropyl]thiazole as a gum (0.22 g).

NMR Spectrum (CDCl₃, δ values) 0.77 (t, 3H), 2.3–2.52 (m, 1H), 2.31–2.61 (m, 1H), 2.72 (s, 3H), 3.21 (s, 3H), 5.10 (s, 2H), 6.84 (doublet of doublets, 1H), 7.03–7.3 (m, 4H), 7.53–7.72 (m, 5H).

EXAMPLE 13

Titanium trichloride (30% w/v in aqueous hydrochloric acid; 5 ml) was added over 15 minutes to a mixture of (E)-2-[1-methoxy-1-(3-(3-(4-nitrophenyl)-prop-2-enyloxy)phenyl)propyl]thiazole (0.7 g) and tetrahydrofuran (10 ml) and the mixture was stirred at ambient temperature for 2 hours. The mixture was poured onto a mixture of ethyl acetate, concentrated sodium hydroxide solution and ice. The organic phase was separated, washed with water and with a saturated aqueous sodium chloride solution, dried (MgSO₄) and evaporated. The residue was purified by column chromatography using a 4:1 v/v mixture of toluene and ethyl acetate as eluent. There was thus obtained (E)-2-[1-(3-(3-(4-aminophenyl)prop-2-enyloxy)phenyl)-1-methoxypropyl]-thiazole as a gum (0.38 g).

NMR Spectrum (CDCl₃, δ values) 0.8 (t, 3H), 2.3–2.5 (m, 1H), 2.6–27 (m, 1H), 3.2 (s, 3H), 3.2–4.0 (broad hump, 2H), 4.6 (m, 2H), 6.1–6.2 (2 t's, 1H, olefinic), 6.6 (d, 1H, olefinic), 6.6–7.3 (m, 9H), 7.7 (d, 1H, thiazole H).

The (E)-2-[1-methoxy-1-(3-(3-(4-nitrophenyl)prop-2-enyloxy)phenyl)propyl]thiazole used as a starting material was obtained by the reaction of (E)-3-(4-nitrophenyl)prop-2-en-1-yl bromide [obtained from (E)-3-(4-nitrophenyl)propenoic acid using the procedure described in Example 5] with 2-[1-(3-hydroxyphenyl)-1-methoxypropyl]thiazole using the procedure described in Example 5. There was thus obtained the required starting material in 63% yield as an oil.

NMR Spectrum (CDCl₃, δ values), 0.8 (t, 3H), 2.3–2.5 (m, 1H), 2.6–2.8 (m, 1H), 3.2 (s, 3H), 4.7 (m, 2H), 6.5–6.6 (d, 1H), 6.7–6.9 (d, 1H), 6.8–7.7 (m, 8H), 8.2 (d, 2H).

EXAMPLE 14

A mixture of 2-[1-methoxy-1-(3-(naphth-2-ylmethoxy)-5-nitrophenyl)propyl]thiazole (Example 9, Compound No. 23; 29.6 g), activated iron (66 g; obtained by stirring a mixture of iron powder and 2N hydrochloric acid solution for 10 minutes, filtering the mixture and washing and drying the solid), water (340 ml) and methanol (1.16 liters) was stirred vigorously and heated to reflux for 4 hours. A second portion of iron (66 g) and ferrous sulphate (13 g) were added and the mixture was heated to reflux for 16 hours. The mixture was cooled to ambient temperature and filtered. The residue was concentrated and partitioned between ethyl acetate and water. The organic phase was washed with a saturated aqueous sodium chloride solution, dried (MgSO₄) and evaporated. There was thus obtained 2-[1-(5-amino-3-(naphth-2-ylmethoxy)phenyl)-1-methoxypropyl]-thiazole (18.9 g, 69%), m.p. 126°–127° C. (recrystallised from ethyl acetate).

EXAMPLE 15

Acetyl chloride (0.1 ml) was added to a mixture of 2-[1-(5-amino-3-(naphth-2-ylmethoxy)phenyl)-1-methoxypropyl]thiazole (0.48 g), triethylamine (0.2 ml) and methylene chloride (15 ml) which had been cooled to 0° C. and the mixture was stirred at this temperature for 15 minutes. The mixture was partitioned between methylene chloride and water. The organic phase was washed with a saturated aqueous sodium chloride solution, dried (MgSO₄) and evaporated. The residue was recrystallised from a mixture of petroleum ether (b.p. 60°–80° C.) and ethyl acetate. There was thus obtained 2-[1-(5-acetamido-3-(naphth-2-ylmethoxy)phenyl)-1-methoxypropyl]thiazole (0.32 g, 60%), m.p. 144°–146° C.

EXAMPLE 16

Methanesulphonyl chloride (0.315 g) was added to a mixture of 2-[1-(5-amino-3-(naphth-2-ylmethoxy)-phenyl)-1-methoxypropyl]thiazole (1.01 g), triethylamine (0.505 g) and methylene chloride (5 ml) and the mixture was stirred at ambient temperature for 18 hours. The mixture was partitioned between methylene chloride and water. The organic phase was washed with a saturated aqueous sodium chloride solution, dried (MgSO₄) and evaporated. The residue was purified by column chromatography using a 1:1 v/v mixture of hexane and ethyl acetate as eluent. There was thus obtained 2-[1-methoxy-1-(5-methanesulphonamido-3-

(naphth-2-ylmethoxy)phenyl)propyl]thiazole as an oil (0.624 g) in 52% yield.

NMR Spectrum (CDCl₃, δ values) 0.78 (t, 3H), 2.31 (m, 1H), 2.58 (m, 1H), 2.84 (s, 3H), 3.13 (s, 3H), 5.10 (s, 2H), 6.60 (s, 1H), 6.75 (t, 1H), 6.83 (t, 1H), 6.86 (t, 1H), 7.27 (d, 1H), 7.40 (m, 3H), 7.61 (d, 1H), 7.75 (m, 4H).

EXAMPLE 17

Ethyl isocyanate (2 ml) was added to a solution of 2-[1-(3-(3-(3-aminophenyl)prop-2-ynyloxy)phenyl)-1-methoxypropyl]thiazole (1.15 g; Example 11, Compound No. 12) in toluene (5 ml) and the mixture was heated to 90° C. for 3 hours. The mixture was cooled to ambient temperature and partitioned between ethyl acetate and water. The organic phase was washed with a saturated sodium chloride solution, dried (MgSO₄) and evaporated. The residue was purified by column chromatography using a 1:1 v/v mixture of hexane and ethyl acetate as eluent. There was thus obtained 2-[1-(3-(3-(3-(3-ethylureido)phenyl)prop-2-ynyloxy)phenyl)-1-methoxypropyl]thiazole as an oil (0.4 g) in 29% yield.

NMR Spectrum (CDCl₃, δ values) 0.8 (t, 3H), 1.1 (t, 3H), 2.4 (m, 1H), 2.65 (m, 1H), 3.2 (q, 2H), 3.2 (s, 3H), 4.8 (s, 2H), 5.3 (broad, 1H), 6.85-7.4 (m, 9H), 7.65 (d, 1H, thiazole H).

EXAMPLE 18

Acetyl chloride (0.193 g) was added to a mixture of 2-[2-hydroxy-1-methoxy-1-(3-naphth-2-ylmethoxy)-phenyl)ethyl]thiazole (0.646 g; Example 9, Compound No. 8), triethylamine (0.166 g) and methylene chloride (10 ml) and the mixture was stirred at ambient temperature for 15 hours. The mixture was evaporated and the residue was purified by column chromatography using a 19:1 v/v mixture of methylene chloride and acetone as eluent. There was thus obtained 2-[2-acetoxy-1-methoxy-1-(3-(naphth-2-ylmethoxy)phenyl)ethyl]-thiazole (0.35 g, 49%), m.p. 100°-101° C. [Example 18, Compound No. 1].

In a similar procedure 2-[1-hydroxy-1-(3-(naphth-2-ylmethoxy)phenyl)ethyl]thiazole (Example 9, Note i.) was reacted with acetic anhydride in the presence of pyridine to give 2-[1-acetoxy-1-(3-naphth-2-ylmethoxy)phenyl)ethyl]thiazole as a gum in 74% yield [Example 18, Compound No. 2].

NMR Spectrum (CDCl₃, δ values) 2.1 (s, 3H), 2.35 (s, 3H), 5.2 (s, 2H), 6.0-7.1 (m, 3H), 7.1-7.3 (m, 2H), 7.5 (m, 3H), 7.7 (d, 1H), 7.8-7.9 (m, 4H).

EXAMPLE 19

A mixture of 2-[1-(3-cinnamyloxyphenyl)-1-methoxypropyl]thiazole (0.25 g; Example 5, Compound No. 11), palladium-on-calcium carbonate catalyst (30 mg) and methanol (5 ml) was stirred at ambient temperature under an atmosphere of hydrogen for 2 hours. The mixture was filtered and the filtrate was evaporated. The residue was purified by column chromatography using increasingly polar mixtures of methylene chloride and diethyl ether as eluent. There was thus obtained 2-[1-methoxy-1-(3-(3-phenylpropoxy)phenyl)propyl]-thiazole as an oil (0.22 g) in 87% yield.

NMR Spectrum (CDCl₃, δ values) 0.78 (t, 3H), 1.75-3.0 (m, 6H), 3.22 (s, 3H), 3.95 (t, 2H), 6.6-7.75 (m, 11H).

EXAMPLE 20

2-[1-(5-Hydroxy-3-(naphth-2-ylmethoxy)phenyl)-1-methoxypropyl]thiazole (Example 9, Compound No. 22) was reacted with ethyl bromoacetate using the conditions described in Example 1. The product was purified by column chromatography using a 10:1 v/v mixture of methylene chloride and ethyl acetate as eluent. There was thus obtained 2-[1-(5-ethoxycarbonylmethoxy-3-(naphth-2-ylmethoxy)phenyl)-1-methoxypropyl]thiazole (Example 20, Compound No. 1) as a gum, in 63% yield.

NMR Spectrum (CDCl₃, δ values) 0.75 (t, 3H), 1.3 (t, 3H), 2.4 (m, 1H), 2.6 (m, 1H), 3.25 (s, 3H), 4.2 (q, 2H), 4.55 (s, 2H), 5.2 (s, 2H), 6.5-7.9 (m, 12H).

The procedure described above was repeated except that chloroacetonitrile was used in place of ethyl bromoacetate. There was thus obtained 2-[1-(5-cyanomethoxy-3-(naphth-2-ylmethoxy)phenyl-1-methoxypropyl]thiazole (Example 20, Compound No. 2) as a gum, in 58% yield.

NMR Spectrum (CDCl₃, δ values) 0.76 (t, 3H), 2.4 (m, 1H), 2.65 (m, 1H), 3.21 (s, 3H), 4.72 (s, 2H), 5.18 (s, 2H), 6.5-7.9 (m, 12H).

The procedure described above was repeated except that iodoacetamide was used in place of ethyl bromoacetate. There was thus obtained 2-[1-(5-carbamoylmethoxy-3-(naphth-2-ylmethoxy)phenyl)-1-methoxypropyl]thiazole (Example 20, Compound No. 3) in 16% yield, m.p. 141°-143° C.

EXAMPLE 21

2-[1-(3-Hydroxy-4-(naphth-2-ylmethoxy)phenyl)-1-methoxypropyl]thiazole (Example 9, Compound No. 28) was reacted with chloroacetonitrole using the conditions described in Example 1. The product was purified by column chromatography using increasingly polar mixtures of methylene chloride and ethyl acetate as eluent. There was thus obtained 2-[1-(3-ethoxycarbonylmethoxy-4-(naphth-2-ylmethoxy)phenyl)-1-methoxypropyl]thiazole (Example 21, Compound No. 1 as a gum, in 59% yield.

NMR Spectrum (CDCl₃, δ values) 0.75 (t, 3H), 2.3-2.45 (m, 1H), 2.6-2.75 (m, 1H), 3.23 (s, 3H), 4.8 (s, 2H), 5.25 (s, 2H), 6.5-7.9 (m, 12H).

The procedure described above was repeated except that allyl bromide was used in place of chloroacetonitrile. There was thus obtained 2-[1-(3-allyloxy-4-(naphth-2-ylmethoxy)phenyl-1-methoxypropyl]thiazole (Example 21, Compound No. 2) as a gum, in 84% yield.

NMR Spectrum (CDCl₃, δ values) 0.75 (t, 3H), 2.3-2.45 (m, 1H), 2.6-2.75 (m, 1H), 3.2 (s, 3H), 4.6 (d, 2H), 5.2-5.5 (q, 2H), 5.25 (s, 2H), 6.0-6.15 (m, 1H), 6.9-7.9 (m, 12H).

The procedure described above was repeated except that ethyl iodide was used in place of chloroacetonitrile. There was thus obtained 2-[1-(3-ethoxy-4-(naphth-2-ylmethoxy)phenyl)-1-methoxypropyl]thiazole (Example 21, Compound No. 3) as a gum in 83% yield.

NMR Spectrum (CDCl₃, δ values) 0.75 (t, 3H), 1.45 (t, 3H), 2.3-2.45 (m, 1H), 2.6-2.7, (m, 1H)), 3.2 (s, 3H), 4.05-4.15 (q, 2H), 5.35 (s, 2H), 6.9-7.9 (m, 12H).

EXAMPLE 22

A mixture of 2-[1-(5-amino-3-(naphth-2-ylmethoxy)-phenyl)-1-methoxypropyl]thiazole (1.01 g; Example 14), ethyl bromoacetate (0.501 g), potassium carbonate (0.692 g) and N,N-dimethylacetamide (12 ml) was stirred and heated to 80° C. for 4 hours. The mixture was cooled to ambient temperature and partitioned between methylene chloride and water. The organic phase was washed with a saturated aqueous sodium chloride solution, dried (MgSO$_4$) and evaporated. The residue was purified by column chromatography using a 4:1 v/v mixture of hexane and ethyl acetate as eluent. There was thus obtained 2-[1-(5-ethoxycarbonylmethylamino-3-(naphth-2-ylmethoxy)phenyl)-1-methoxypropyl]thiazole (Example 22, Compound No. 1) as a glass (0.877 g), in 72% yield.

NMR Spectrum (CDCl$_3$, δ values) 0.77 (t, 3H), 1.28 (t, 3H), 2.38 (m, 1H), 2.67 (m, 1H), 3.18 (s, 3H), 3.86 (s, 3H), 4.22 (q, 2H), 5.15 (s, 2H), 6.15 (t, 1H), 6.91 (t, 1H), 6.54 (t, 1H), 7.21 (d, 1H), 7.50 (m, 3H), 7.66 (d, 1H), 7.80 (m, 4H).

The procedure described above was repeated except that iodoacetamide was used in place of ethyl bromoacetate and the mixture was heated to 80° C. for 24 hours. There was thus obtained 2-[1-(5-carbamoylmethylamino-3-(naphth-2-ylmethoxy)phenyl)-1-methoxypropyl]thiazole (Example 22, Compound No. 2) as a glass (0.502 g) in 54% yield.

NMR Spectrum (CDCl$_3$, δ values) 0.76 (t, 3H), 2.37 (m, 1H), 2.63 (m, 1H), 3.18 (s, 3H), 3.73 (s, 2H), 5.14 (s, 2H), 5.52 (broad s, 1H), 6.14 (t, 1H), 6.42 (t, 1H), 6.51 (broad s, 1H), 6.58 (t, 1H), 7.21 (d, 1H), 7.45–7.83 (m, 8H).

The procedure described above was repeated except that iodoacetonitrile was used in place of ethyl bromoacetate and the mixture was heated to 80° C. for 30 hours. There was thus obtained 2-[1-(5-cyanomethylamino-3-(naphth-2-ylmethoxy)phenyl-1-methoxypropyl]thiazole (Example 22, Compound No. 3) as a gum (0.585 g), in 66% yield.

NMR Spectrum (CDCl$_3$, δ values) 0.77 (t, 3H), 2.39 (m, 1H), 2.67 (m, 1H), 3.21 (s, 3H), 4.04 (s, 2H), 5.16 (s, 2H), 6.24 (t, 1H), 6.5–7.9 (m, 11H).

A solution of 2-[1-(5-ethoxycarbonylmethylamino-3-(naphth-2-ylmethoxy)phenyl)-1-methoxypropyl]-thiazole (0.877 g; Compound No. 1 immediately above) in diethyl ether (40 ml) was added to a stirred suspension of lithium aluminium hydride (0.3 g) in diethyl ether (20 ml) and the mixture was stirred at ambient temperature for 2.5 hours. Water (30 ml) was carefully added and the mixture was stirred for 30 minutes and filtered. The organic phase was washed with a saturated aqueous sodium chloride solution, dried (MgSO$_4$) and evaporated. There was thus obtained 2-[1-(5-(2-hydroxyethyl)amino-3-(naphth-2-ylmethoxy)phenyl-1-methoxypropyl]thiazole as a gum (0.545 g), in 68% yield [Example 22, Compound No. 4].

NMR Spectrum (CDCl$_3$, δ values) 0.78 (t, 3H), 2.37 (m, 1H), 2.64 (m, 1H), 3.19 (s, 3H), 3.26 (t, 2H), 3.79 (t, 2H), 5.15 (s, 2H), 6.22 (t, 1H), 6.43 (t, 1H), 6.52 (t, 1H), 7.20 (d, 1H), 7.5–7.8 (m, 8H).

EXAMPLE 23

Trifluoroacetic anhydride (0.165 ml) was added dropwise to a mixture of 2-[1-(5-amino-3-(naphth-2-ylmethoxy)phenyl-1-methoxypropyl]thiazole (0.43 g; Example 14), triethylamine (0.165 ml) and methylene chloride (20 ml) which had been cooled to 5° C. The mixture was stirred at 5° C. for 30 minutes and then partitioned between methylene chloride and water. The organic layer was dried (MgSO$_4$) and evaporated. A mixture of the trifluoroacetanilide so obtained, methyl iodide (0.27 ml, 4 equivalents) and acetone (5 ml) was heated almost to reflux. Powdered potassium hydroxide (0.24 g, 4 equivalents) was added and the mixture was heated to reflux for 5 minutes. The mixture was evaporated, water (10 ml) and acetone (10 ml) were added to the residue and the mixture was heated to reflux for 10 minutes. The mixture was concentrated and the residue was extracted with ethyl acetate (3×50 ml). The combined extracts were washed with water, dried (MgSO$_4$) and evaporated. The residue was recrystallised from a mixture of petroleum ether (b.p. 60°–80° C.) and methylene chloride. There was thus obtained 2-[1-methoxy-1-(5-methylamino-3-(naphth-2-ylmethoxy)phenyl)-propyl]-thiazole (0.183 g, 41%), m.p. 137° C. [Example 23, Compound No. 1].

The procedure described above was repeated except that the amount of each of the methyl iodide and potassium hydroxide was increased to 10 equivalents. The product so obtained was purified by column chromatography using a 1:1 v/v mixture of hexane and ethyl acetate as eluent. There was thus obtained 2-[1-(5-dimethylamino-3-(naphth-2-ylmethoxy)phenyl)-1-methoxypropyl]thiazole as a gum, in 31% yield [Example 23, Compound No. 2].

NMR Spectrum (CDCl$_3$, δ values) 0.78 (t, 3H), 2.40 (m, 1H), 2.67 (m, 1H), 2.91 (s, 6H), 3.20 (s, 3H), 5.17 (s, 2H), 6.30 (m, 1H), 6.53 (m, 2H), 7.19 (d 1H), 7.5–7.9 (m, 8H).

EXAMPLE 24

A mixture of 2-[1-(3-cyano-4-(naphth-2-ylmethoxy)-phenyl)-1-methoxypropyl]thiazole (0.65 g; Example 9, Compound No. 29), powdered potassium hydroxide (0.324 g) and tert-butanol (4 ml) was heated to reflux for 2 hours. The mixture was cooled to ambient temperature and partitioned between ethyl acetate and water. The organic layer was washed with a saturated aqueous sodium chloride solution, dried (MgSO$_4$) and evaporated. The residue was recrystallised from a mixture of petroleum ether (b.p. 60°–80° C.) and methylene chloride. There was thus obtained 2-[1-(3-carbamoyl-4-(naphth-2-ylmethoxy)phenyl)-1-methoxypropyl]-thiazole (0.35 g, 52%), m.p. 177°–179° C.

EXAMPLE 25

A mixture of 2-[1-(ethoxycarbonylmethoxy)-1-(5-methoxy-3-(naphth-2-ylmethoxy)phenyl)propyl]-thiazole (0.67 g; Example 9, Compound No. 17), sodium hydroxide (0.2 g), water (3 ml) and methanol (15 ml) was stirred at ambient temperature for 18 hours. The mixture was acidified by the addition of 5N hydrochloric acid solution and the methanol was evaporated. The residue was partitioned between ethyl acetate and water. The organic phase was dried (MgSO$_4$) and evaporated. There was thus obtained 2-[1-carboxymethoxy-1-(5-methoxy-3-(naphth-2-ylmethoxy)phenylpropyl]-thiazole (0.56 g, 90%), m.p. 160°–161° C.

EXAMPLE 26

A mixture of 2-[1-methoxycarbonylmethoxy-1-(5-methoxy-3-(naphth-2-ylmethoxy)phenyl)propyl]-thiazole (0.66 g; obtained in 56% yield using the procedure described for the preparation of Compound No. 17 of Example 9 except that methyl iodoacetate was used as the alkylating agent) and a saturated solution of ammonia in methanol (50 ml) was stirred at ambient temperature for 3 hours. The mixture was evaporated and the residue was purified by column chromatography using increasingly polar mixtures of petroleum ether (b.p. 60°–80° C.) and ethyl acetate as eluent. There was thus obtained 2-[1-carbamoylmethoxy-1-(5-methoxy-3-(naphth-2-ylmethoxy)phenyl)propyl]thiazole (0.5 g, 78%), m.p. 60°–62° C.

EXAMPLE 27

Trifluoroacetic anhydride (0.153 ml) was added to a mixture of 2-[1-carbamoylmethoxy-1-(5-methoxy-3-(naphth-2-ylmethoxy)phenyl)propyl]thiazole (0.462 g, Example 26), pyridine (0.16 ml) and dimethoxyethane (2 ml) which had been cooled to 0° C. The mixture was stirred at ambient temperature for 3 hours and partitioned between diethyl ether and water. The organic layer was washed with 2N hydrochloric acid solution and with water, dried (MgSO$_4$) and evaporated. The residue was purified by column chromatography using increasingly polar mixtures of petroleum ether (b.p. 60°-80° C.) and ethyl acetate as eluent. There was thus obtained 2-[1-cyanomethoxy-1-(5-methoxy-3-(naphth-2-ylmethoxy)phenyl)propyl]thiazole as a gum (0.33 g) in 75% yield.

NMR Spectrum (CDCl$_3$, δ values) 0.82 (t, 3H), 2.4 (m, 2H), 3.78 (s, 3H), 4.13 (s, 2H), 5.18 (s, 2H), 6.52 (t, 1H), 6.61 (t, 1H), 6.67 (t, 1H), 7.3 (d, 1H), 7.46-7.9 (m, 8H).

EXAMPLE 28

Trifluoroacetic acid (0.2 ml) was added to amixture of 2-[1-(3-tert-butoxycarbonyl-4-(naphth-2-ylmethoxy)phenyl)-1-methoxypropyl]thiazole (1.9 g; Example 9, Compound No. 30) and methylene chloride (50 ml) and the mixture was stirred at ambient temperature for 2 hours. The mixture was evaporated and the residue was partitioned between ethyl acetate and water. The organic layer was washed with a saturated aqueous sodium hydrogen carbonate solution and with water, dried (MgSO$_4$) and evaporated. The residue was purified by column chromatography using increasingly polar mixtures of methylene chloride and ethyl acetate as eluent. There was thus obtained 2-[1-(3-carboxy-4-(naphth-2-ylmethoxy)phenyl)-1-methoxypropyl]thiazole (0.7 g).

A mixture of the product so obtained and oxalyl chloride (5 ml) was stirred at ambient temperature for 30 minutes. The mixture was evaporated and a solution of the residue in methylene chloride (10 ml) was added to a saturated solution of dimethylamine in methanol (5 ml). The mixture was stirred at ambient temperature for 30 minutes. The mixture was partitioned between ethyl acetate and water. The organic layer was washed with 2N hydrochloric acid solution and with water, dried (MgSO$_4$) and evaporated. The residue was purified by column chromatography using increasingly polar mixtures of petroleum ether (b.p. 60°-80° C.) and ethyl acetate as eluent. There was thus obtained 2-[1-(3-dimethylcarbamoyl-4-(naphth-2-ylmethoxy)phenyl)-1-methoxypropyl]thiazole as an oil, in 20% yield (Example 28, Compound No. 1).

NMR Spectrum (CDCl$_3$, δ values) 0.75 (t, 3H), 2.4 (m, 1H), 2.65 (m, 1H), 2.8 (s, 3H), 3.1 (s, 3H), 3.2 (s, 3H), 5.25 (s, 2H), 6.95 (d, 1H), 7.25 (d, 1H), 7.4-7.55 (m, 5H), 7.7 (d, 1H), 7.8-7.9 (m, 4H).

In a similar procedure for the conversion of an appropriate acid to an amide, a mixture of 2-[1-(3-(3-(3-carboxyphenyl)prop-2-ynyloxy)phenyl)-1-methoxypropyl]thiazole (0.4 g) and oxalyl chloride (4 ml) was stirred at ambient temperature for 30 minutes. The mixture was evaporated and the residue was dissolved in tetrahydrofuran (2 ml). A concentrated aqueous ammonium hydroxide solution (4 ml) was added and the mixture was stirred at ambient temperature for 10 minutes. The mixture was partitioned between diethyl ether and water. The organic layer was washed with water, dried (MgSO$_4$) and evaporated. The residue was purified by column chromatography using a 3:1 v/v mixture of ethyl acetate and hexane. There was thus obtained 2-[1-(3-(3-(3-carbamoylphenyl)prop-2-ynyloxy)phenyl)-1-methoxypropyl]thiazole as an oil in 70% yield (Example 28, Compound No. 2).

NMR Spectrum (CDCl$_3$, δ values) 0.76 (t, 3H), 2.45 (m, 1H), 2.65 (m, 1H), 3.2 (s, 3H), 4.9 (s, 2H), 5.8-6.5 (broad lump, 2H), 7.2 (d, 1H), 6.9-8.2 (m, 9H).

The 2-[1-(3-(3-(3-carboxyphenyl)prop-2-ynyloxy)phenyl)-1-methoxypropyl]thiazole used as a starting material was obtained by basic hydrolysis of the corresponding 3-methoxycarbonyl-substituted compound (Example 11, Compound No. 9) using the procedure described in Example 25. There was thus obtained the required starting material as an oil in 93% yield.

EXAMPLE 29

Using a similar procedure to that described in Example 1 except that the reaction duration was 30 minutes (E)-cinnamyl bromide was reacted with 2-[1-(3,5-dihydroxyphenyl)-1-methoxypropyl]thiazole. The product was purified by column chromatography using a 5:1 v/v mixture of petroleum ether (b.p. 60°-80° C.) and ethyl acetate as eluent. There was thus obtained 2-[1-(3-(E)-cinnamyloxy-5-hydroxyphenyl)-1-methoxypropyl]thiazole (0.06 g, 11%), m.p. 137°-138° C. The 2-[1-(3,5-dihydroxyphenyl)-1-methoxypropyl]thiazole used as a starting material was obtained as follows:

Water (1 ml) was added to a mixture of 2-[1-(5-tert-butoxydimethylsilyloxy-3-(naphth-2-ylmethoxy)phenyl)-1-methoxypropyl]thiazole (1.25 g; Example 9, Note t.) and trifluoroacetic acid (6 ml) which had been cooled to 0° C. The mixture was stirred and allowed to warm to ambient temperature. The mixture was partitioned between ethyl acetate and a saturated aqueous ammonium chloride solution. The organic phase was washed with a saturated aqueous sodium bicarbonate solution, with a saturated aqueous sodium chloride solution dried (MgSO$_4$) and evaporated. The residue was purified by column chromatography using increasingly polar mixtures of petroleum ether (b.p. 60°-80° C.) and ethyl acetate as eluent. There was thus obtained the required starting material as an oil (0.5 g) in 78% yield.

EXAMPLE 30

Using a similar procedure to that described in Example 3, except that the appropriate 2-, 4- or 5-substituted thiazole was used in place of 2-[1-hydroxy-1-[3-methoxy-5-(naphth-2-ylmethoxy)phenyl]thiazole, there were obtained the compounds described in the following table.

TABLE VI

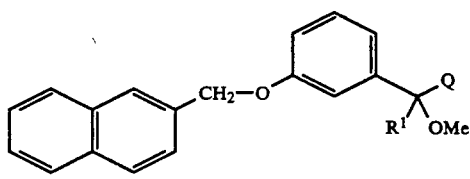

| Ex. 30 Compd. No. | R$^1$ | Q | m.p. (°C.) | Yield (%) |
|---|---|---|---|---|
| 1$^a$ | Et | 5-methylthiazol-2-yl | 69-71 | 83 |
| 2$^b$ | Et | 4,5-dimethylthiazol-2yl | 99-100 | 70 |

TABLE VI-continued

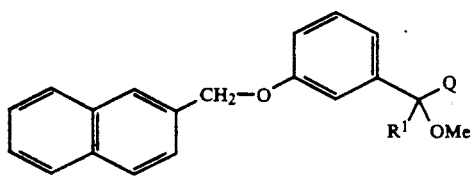

| Ex. 30 Compd. No. | R[1] | Q | m.p. (°C.) | Yield (%) |
|---|---|---|---|---|
| 3[c] | Me | 4-thiazolyl | 124 | 94 |
| 4[d] | Et | 4-thiazolyl | 93-94 | 71 |
| 5[e] | H | 5-thiazolyl | oil | 69 |
| 6[f] | Et | 5-thiazolyl | 88-90 | 80 |

Notes a. The product was purified by recrystallisation from pentane.

The 2-[1-hydroxy-1-(3-naphth-2-ylmethoxy)phenyl)-propyl]-5-methylthiazole used as a starting material was obtained as follows:

The procedure described in the 4th paragraph of the portion of Example 1 which is concerned with the preparation of starting materials was used to react 3-(naphth-2-ylmethoxy)propiophenone with 5-methylthiazol-2-yl-lithium except that the reaction was carried out at a temperature of −78° C. and the mixture was stirred at −78° C. for 30 minutes. There was thus obtained the required starting material in 74% yield, m.p. 97°-100° C. (recrystallised from carbon tetrachloride).

The 3-(naphth-2-ylmethoxy)propiophenone used as a starting material was obtained by reacting 2-bromomethylnaphthalene with 3-cyanophenol using the conditions described in Example 1 and thereafter reacting the product so obtained with ethylmagnesium bromide using the procedure described in Organic Synthesis, Collect. Vol. III, p. 26. There was thus obtained the required starting material in 58% yield, m.p. 56°-57° C.

b. The product was purified by recrystallisation from pentane.

The 2-[1-hydroxy-1-(3-naphth-2-ylmethoxy)phenyl)-propyl]-4,5-dimethylthiazole used as a starting material was obtained by repeating the procedure described in Note a. immediately above except that 4,5-dimethyl-thiazol-2-yl-lithium was used in place of 5-methyl-thiazol-2-yl-lithium. There was thus obtained the required starting material in 70% yield, m.p. 88°-91° C. (recrystallised from pentane).

c. A catalytic amount (0.1 equivalents) of 1,4,7,10,13,16-hexaoxacyclooctadecane (18-Crown-6) was added to the reaction mixture. The product was recrystallised from a mixture of pentane and diethyl ether.

The 4-[1-hydroxy-1-(3-(naphth-2-ylmethoxy)phenyl)ethyl]thiazole used as a starting material was obtained as follows:

A solution of methyl 4-thiazolyl ketone (Chem. Abs. 89, 197387 y) in tetrahydrofuran was added to an equimolar amount of a Grignard reagent prepared by the reaction of 3-(naphth-2-ylmethoxy)bromobenzene and magnesium under tetrahydrofuran. The reaction mixture was stirred at ambient temperature for 15 minutes, poured into a saturated ammonium chloride solution and extracted with ethyl acetate. The organic layer was dried (MgSO$_4$) and evaporated. There was thus obtained the required starting material in 38% yield as an oil.

The 2-(naphth-2-ylmethoxy)bromobenzene used as a starting material was obtained by the reaction of 2-bromomethylnaphthalene and 3-bromophenol using the conditions described in Example 1. There was thus obtained the required bromobenzene in 68% yield, m.p. 109°-111° C. (recrystallised from a mixture of ethanol and ethyl acetate).

d. A catalytic amount of 18-crown-6 was added to the reaction mixture. The product was recrystallised from a mixture of pentane and diethyl ether.

The 4-[1-hydroxy-1-(3-naphth-2-ylmethoxy)phenyl)-propyl]thiazole used as a starting material was obtained using the procedure described in Note c. above except that ethyl 4-thiazolyl ketone was used in place of methyl 4-thiazolyl ketone. There was thus obtained the required starting material in 50% yield, m.p. 82°-83° C. (recrystallised from a mixture of pentane and diethyl ether).

Ethyl 4-thiazolyl ketone used as a starting material was obtained using the following procedure:

Ethylmagnesium bromide [2M in tetrahydrofuran, 4 ml] was added dropwise to a mixture of N,N-dimethyl-thiazole-4-carboxamide (0.936 g: Tetrahedron, 1977, 33, 1337) and tetrahydrofuran (10 ml) which had been cooled to 0° C. Water (5 ml) was added and the mixture was acidified to pH2 by the addition of 2N hydrochloric acid solution and extracted with diethyl ether (2×100 ml). The combined extracts were dried (MgSO$_4$) and evaporated. The residue was purified by column chromatography using methylene chloride as eluent. There was thus obtained the required ketone as an oil, in 27% yield.

e. The reaction was carried out at a reaction temperature of −5° to −10° C. The reaction mixture was stirred at this temperature for 1 hour. The product was purified by column chromatography using a 5:1 v/v mixture of toluene and ethyl acetate as eluent. The product gave the following NMR data: (CDCl$_3$, δ values) 3.3 (s, 3H), 5.3 (s, 2H), 5.7 (s, 1H), 6.9-7.3 (m, 4H), 7.5-7.6 (m, 3H), 7.8 (s, 1H), 7.9-9.0 (m, 4H), 9.0 (s, 1H).

The 5-[α-hydroxy-3-(naphth-2-ylmethoxy)benzyl]-thiazole used as a starting material was obtained as follows:

A mixture of ethyl thiazole-5-carboxylate (8.5 g), 2N sodium hydroxide solution (28 ml) and ethanol (50 ml) was stirred at ambient temperature for 2.5 hours. The mixture was concentrated and partitioned between diethyl ether and water. The aqueous layer was acidified by the addition of 2N hydrochloric acid solution and extracted with methylene chloride (6×50 ml). The combined extracts were dried (MgSO$_4$) and evaporated to give thiazole-5-carboxylic acid (4 g, 57%), m.p. 214°-216° C.

Ethyl chloroformate (1.36 ml) was added to a mixture of a portion (1.8 g) of the acid so obtained, triethylamine (2.04 ml) and tetrahydrofuran (30 ml) which had been cooled to −15° C. and the mixture was stirred at this temperature for 20 minutes. The mixture was then cooled to −40° C. and a solution in tetrahydrofuran of 3-(naphth-2-ylmethoxy)phenylmagnesium bromide [prepared by stirring a mixture of 3-(naphth-2-ylmethoxy)phenyl bromide (5 g), magnesium (0.44 g), iodine (1 crystal), 1,2-dibromoethane (3 drops) and tetrahydrofuran (20 ml)] was cooled to 0° C. and added dropwise. The resultant mixture was stirred at −40° C. for 1 hour and at 0° C. for 2 hours. The mixture was poured onto a mixture of ice and dilute hydrochloric acid solution and a diethyl ether extract was taken. The organic layer was washed with a saturated aqueous sodium chloride solution, dried (MgSO₄) and evaporated. The residue was purified by column chromatography using a 9:1 v/v mixture of toluene and ethyl acetate as eluent. There was thus obtained 3-(naphth-2-ylmethoxy)phenyl 5-thiazolyl ketone (1.78 g, 37%), m.p. 109°–110° C.

A solution in tetrahydrofuran of ethylmagnesium bromide [prepared from bromoethane (2.2 g), magnesium (0.445 g) and tetrahydrofuran (12 ml)] was added to a portion (1.28 g) of the ketone so obtained and the mixture was heated to reflux for 3 hours. The mixture was cooled to ambient temperature and partitioned between ethyl acetate and a saturated aqueous ammonium chloride solution. The organic phase was dried (MgSO₄) and evaporated. The residue was purified by column chromatography using a 7:3 v/v mixture of toluene and ethyl acetate as eluent. There were thus obtained in turn 5-[1-hydroxy-1-(3-(naphth-2-ylmethoxy)phenyl)propyl]thiazole as a gum (0.41 g), in 29% yield (starting material for Example 30, Compound No. 6) and 5-[α-hydroxy-3-(naphth-2-ylmethoxy)benzyl]-thiazole as a solid (0.41 g), in 32% yield.

f. The reaction was carried out at a reaction temperature of −5° to −10° C. for 1 hour. The product was purified by column chromatography using a 9:1 v/v mixture of toluene and ethyl acetate as eluent.

EXAMPLE 31

A solution of 2-[1-methoxy-1-(3-(naphth-2-ylmethoxy)phenyl)propyl]thiazole (1.56 g) in diethyl ether (32 ml) was added dropwise to a mixture of n-butyl-lithium (1.6M in hexane, 4 ml) and diethyl ether (32 ml) which had been cooled to −78° C. and the mixture was stirred at this temperature for 1 hour. A solution of p-toluenesulphonyl chloride (1.22 g) in diethyl ether (6 ml) was added dropwise. The mixture was stirred at −78° C. for 30 minutes and at ambient temperature for 2 hours. The mixture was partitioned between diethyl ether and water. The organic layer was dried (MgSO₄) and evaporated. The residue was purified by column chromatography using a 4:1 v/v mixture of methylene chloride and petroleum ether (b.p. 60°–80° C.) as eluent. There was thus obtained 5-chloro-2-[1-methoxy-1-(3-(naphth-2-ylmethoxy)phenyl)propyl]thiazole (0.5 g, 30%), m.p. 82°–85° C. [Example 31, Compound No. 1].

The procedure described above was repeated except that acetyl chloride was used in place of p-toluenesulphonyl chloride. There was thus obtained 5-acetyl-2-[1-methoxy-1-(3-(naphth-2-ylmethoxy)phenyl)propyl]-thiazole in 20% yield, m.p. 93°–94° C. [Example 31, Compound No. 2].

EXAMPLE 32

A mixture of 2-[1-methoxy-1-(3-naphth-2-ylmethoxy)phenyl)propyl]thiazole-2-carboxylic acid (0.5 g) and thionyl chloride (5 ml) was heated to reflux for 30 minutes. The mixture was evaporated. A mixture of the residue so obtained, methanol (5 ml), triethylamine (1 ml) and methylene chloride (10 ml) was stirred at 0° C. for 1 hour. The mixture was partitioned between methylene chloride and 2N hydrochloric acid. The organic layer was separated, washed with water, dried (MgSO₄) and evaporated. There was thus obtained methyl 2-[1-methoxy-1-(3-(naphth-2-ylmethoxy)phenyl)propyl]-thiazole-2-carboxylate in 76% yield, m.p. 92°–95° C.

The 2-[1-methoxy-1-(3-(naphth-2-ylmethoxy)phenyl)propyl]-thiazole-2-carboxylic acid used as a starting material was obtained as follows:

A solution of 2-[1-methoxy-1-(3-(naphth-2-ylmethoxy)phenyl)propyl]thiazole (1.56 g) in diethyl ether (32 ml) was added dropwise to a mixture of n-butyl-lithium (1.6M in hexane, 4 ml) and diethyl ether (32 ml) which had been cooled to −78° C. and the mixture was stirred at this temperature for 1 hour. An excess of solid carbon dioxide was added and the mixture was allowed to warm to ambient temperature and stirred for 1.5 hours. The mixture was partitioned between diethyl ether and 0.1N sodium hydroxide solution. The aqueous phase was acidified by the addition of 2N hydrochloric acid solution and extracted with a 1:1 v/v mixture of diethyl ether and ethyl acetate. The organic phase was dried (MgSO₄) and evaporated. There was thus obtained the required starting material (1.15 g, 66%), m.p. 161°–163° C.

EXAMPLE 33

Diphenylphosphoryl azide (0.587 ml) was added to a stirred suspension of 2-[1-methoxy-1-(3-(naphth-2-ylmethoxy)phenyl)propyl]-thiazole-2-carboxylic acid (1.08 g) in dimethylformamide (3 ml) which had been cooled to 0° C. The mixture was stirred at 0° C. for 30 minutes and at ambient temperature for 2.5 hours. Ethanol (2 ml) was added and the mixture was heated to reflux for 2 hours. The mixture was partitioned between diethyl ether and water. The organic phase was washed with water and with a saturated aqueous sodium chloride solution, dried (MgSO₄) and evaporated. The residue was purified by column chromatography using increasingly polar mixtures of methylene chloride and diethyl ether as eluent. There was thus obtained 5-ethoxycarbonylamino-2-[1-methoxy-1-(3-(naphth-2-ylmethoxy)phenyl)propyl]thiazole (0.3 g, 25%), m.p. 68°–70° C. (crystallised under water).

EXAMPLE 34

The procedure described in Example 3 was repeated except that 2-[1-hydroxy-1-(3-(naphth-2-ylthio)phenyl)-propyl]thiazole was used in place of 2-[1-hydroxy-1-[3-methoxy-5-(naphth-2-ylmethoxy)phenyl]propyl]-thiazole. The reaction product was purified by column chromatography using increasingly polar mixtures of hexane and ethyl acetate as eluent. There was thus obtained 2-[1-methoxy-1-(3-(naphth-2-ylthio)phenyl)-propyl]thiazole as an oil, in 86% yield.

NMR Spectrum (CDCl₃, δ values) 0.75 (t, 3H), 2.4 (m, 1H), 2.65 (m, 1H), 3.2 (s, 3H), 7.2–7.58 (m, 8H), 7.65–7.85 (m, 5H).

The 2-[1-hydroxy-1-(3-(naphth-2-ylthio)phenyl)-propyl]-thiazole used as a starting material was obtained as follows A mixture of 2-naphthalenethiol (12.94 g), 3-bromopropiophenone (17.35 g), cuprous oxide (5.83 g), sodium hydroxide (3.24 g) and dimethylformamide (130 ml) was heated to reflux for 18 hours. The mixture was concentrated and the residue was partitioned between diethyl ether and water. The organic phase was dried (MgSO₄) and evaporated. The residue was dissolved in a mixture of ethyl acetate and hexane and treated with charcoal. The solution was filtered and evaporated. The residue was recrystallised from a mixture of methanol and water to give 3-(naphth-2-ylthio)propiophenone (5.23 g, 22%), m.p. 90°–91° C.

A solution in tetrahydrofuran (5 ml) of a portion (1 g) of the product so obtained was treated with thiazol-2-yl-lithium [prpeared from thiazole (0.29 g) and n-butyl-lithium (1.6M in hexane, 2.2 ml)] using the conditions described in the 4th paragraph of the portion of Example 1 which is concerned with the preparation of starting materials. The product was purified by column chromatography using increasingly polar mixtures of hexane and ethyl acetate as eluent. There was thus obtained the required starting material (0.61 g, 48%) as an oil.

NMR Spectrum (CDCl$_3$, $\delta$ values) 0.89 (t, 3H), 2.35 (m, 2H), 3.5 (broad s, 1H), 7.2–7.55 (m, 7H), 7.63–7.85 (m, 6H).

EXAMPLE 35

A solution of potassium peroxymonosulphate (0.78 g) in water (3 ml) was added to a solution of 2-[1-methoxy-1-(3-(naphth-2-ylthio)phenyl)propyl]thiazole (0.49 g) in ethanol (10 ml) which had been cooled to 0° C. The mixture was stirred at 0° C. for 15 minutes. The mixture was partitioned between chloroform and water. The organic phase was dried (MgSO$_4$) and evaporated. The residue was purified by column chromatography using increasingly polar mixtures of hexane and ethyl acetate as eluent. There was thus obtained 2-[1-methoxy-1-(3-(naphth-2-ylsulphinyl)phenyl)propyl]thiazole as an oil (0.35 g), in 67% yield.

NMR Spectrum (CDCl$_3$, $\delta$ values) 0.7 (t, 3H), 2.4 (m, 1H), 2.65 (m, 1H), 3.18 (d, 3H), 7.22 (m, 1H), 7.35–7.65 (m, 7H), 7.8–7.95 (m, 4H), 8.35 (s, 1H).

EXAMPLE 36

The procedure described in Example 35 was repeated except that a solution of potassium peroxymonosulphate (1.16 g) in water (6 ml) was employed. There was thus obtained 2-[1-methoxy-1-(3-(naphth-2-ylsulphonyl)-phenyl)propyl]thiazole (0.33 g, 60%), m.p. 103°–107° C.

EXAMPLE 37

Using a similar procedure to that described in Example 4, 2-[1-hydroxy-1-(5-(naphth-2-yloxy)pyrid-3-yl)propyl]thiazole was reacted with methyl iodide to give 2-[1-methoxy-1-(5-(naphth-2-yloxy)pyrid-3-yl)propyl]thiazole as an oil in 54% yield.

NMR Spectrum (CDCl$_3$, $\delta$ values) 0.8(t, 3H), 2.47(m, 1H), 2.67(m, 1H), 3.28(s, 3H), 7.22 (doublet of doublets, 1H), 7.32(d, 1H), 7.33(d, 1H), 7.4–7.53(m, 2H), 7.62(t, 1H), 7.68(doublet of doublets, 1H), 7.7(d, NMR Spectrum (CDCl$_3$, $\delta$ values) 0.8 (t, 3H), 2.47 (m, 1H), 2.67 (m, 1H), 3.28 (s, 3H), 7.22 (doublet of doublets, 1H), 7.32 (d, 1H), 7.33 (d, 1H), 7.4–7.53 (m, 2H), 7.62 (t, 1H), 7.68 (doublet of doublets, 1H), 7.7 (d, 1H), 7.85 (m, 2H), 8.29 (d, 1H), 8.49 (d, 1H).

The 2-[1-hydroxy-1-(5-naphth-2-yloxy)pyrid-3-yl)propyl]thiazole used as a starting material was obtained as follows:

The procedure described in the portion of Example 4 which is concerned with the preparation of starting materials was repeated except that 2-naphthol was used in place of 2-naphthylmethanol. There were thus obtained in turn 3-bromo-5-(naphth-2-yloxy)pyridine in 35% yield, m.p. 74°–75° C., and the required starting material as an oil, in 70% yield.

EXAMPLE 38

The following illustrate representative pharmaceutical dosage forms containing the compound of formula I, or a (1-4C)alkoxycarbonyl derivative thereof, or a pharmaceutically-acceptable salt salt thereof (hereafter compound X), for therapeutic or prophylactic use in humans:

| (a) Tablet I | mg/tablet |
|---|---|
| Compound X | 100 |
| Lactose Ph. Eur. | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur. | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 mg |
| Lactose Ph. Eur. | 488.5 |
| Magnesium stearate | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate EP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |

-continued

| | |
|---|---|
| Dichlorotetrafluoroethane | 191.6 |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE $$Ar^1-A-X-Ar^2-\underset{OR^2}{\overset{R^1}{\underset{|}{\overset{|}{C}}}}-Q \qquad I$$

$$H-X-Ar^2-\underset{OR^2}{\overset{R^1}{\underset{|}{\overset{|}{C}}}}-Q \qquad II$$

$$R^3-X-Ar^2-\underset{OR^2}{\overset{R^1}{\underset{|}{\overset{|}{C}}}}-Q \qquad III$$

$$R^3-X-Ar^2-\underset{OH}{\overset{R^1}{\underset{|}{\overset{|}{C}}}}-Q \qquad IV$$

$$Ar^1-A-X-Ar^2-\underset{R^1}{\overset{OH}{\underset{|}{\overset{|}{C}}}}-Q \qquad V$$

$$\equiv-A^1-X-Ar^2-\underset{OR^2}{\overset{R^1}{\underset{|}{\overset{|}{C}}}}-Q \qquad VI$$

What we claim is:

1. A method of treating a disease or medical condition mediated alone or in part by one or more leukotrienes which comprises administering to a warm-blooded animal requiring such treatment an effective amount of a thiazole of the formula I $$Ar^1-A-X-Ar^2-\underset{OR^2}{\overset{R^1}{\underset{|}{\overset{|}{C}}}}-Q$$

wherein $Ar^1$ is phenyl or naphthyl which may optionally bear one or more substituents selected from halogeno, amino, hydroxy, cyano, formyl, carbamoyl, (1-6C)alkyl, (2-6C)alkenyl, (2-6C)alkynyl, (1-6C)alkoxy, (1-6C)alkylthio, (1-6C)alkylsulphinyl, (1-6C)alkylsulphonyl, (1-6C)alkylamino, di-[(1-4C)alkyl]amino, (1-4C)alkoxycarbonyl, N-[(1-6C)alkyl]carbamoyl, N,N-di[(1-4C)alkyl]carbamoyl, (2-6C)alkanoyl, (2-6C)alkanoylamino, (1-4C)alkylureido, hydroxy-(1-4C)alkyl and fluoro-(1-4C)alkyl;

wherein A is a direct link to X, or is (1-6C)alkylene, (3-6C)alkenylene, (3-6C)alkynylene or cyclo(-3-6C)alkylene;

wherein X is oxy, thio, sulphinyl, sulphonyl or imino;

wherein $Ar^2$ is phenylene which may optionally bear one or two substituents selected from halogeno, hydroxy, amino, nitro, cyano, carbamoyl, (1-6C)alkyl, (1-6C)alkoxy, (3-4C)alkenyloxy, (1-6C)alkylthio, (1-6C)alkylsulphinyl, (1-6C)alkylsulphonyl, (1-6C)alkylamino, di-[(1-4C)alkyl]amino, (1-4C)alkoxycarbonyl, N-[(1-6C)alkyl]carbamoyl, N,N-di-[(1-4C)alkyl]carbamoyl, (2-6C)alkanoylamino, fluoro-(1-4C)alkoxy, hydroxy-(2-4C)alkoxy, (1-4C)alkoxy-(2-4C)alkoxy, amino-(2-4C)alkoxy, cyano-(1-4C)alkoxy, carbamoyl-(1-4C)alkoxy, (1-6C)alkylamino-(2-4C)alkoxy, di-[(1-4C)alkyl]amino-(2-4C)alkoxy, (1-4C)alkoxycarbonyl-(1-4C)alkoxy, N-[(1-6C)alkyl]carbamoyl-(1-4C)alkoxy, N,N-[di-(1-4C)alkyl]carbamoyl-(1-4C)alkoxy, fluoro-(1-4C)alkyl, hydroxy-(1-4C)alkyl, amino-(1-4C)alkyl, cyano-(1-4C)alkyl, (1-4C)alkyl, (1-4C)alkylamino-(1-4C)alkyl, di-[(1-4C)alkyl]amino-(1-4C)alkyl, (2-6C)alkanoylamino-(1-4C)alkyl, (1-4C)alkoxycarbonyl-(1-4C)-alkylamino, carbamoyl-(1-4C)alkylamino, cyano-(1-4C)alkylamino, hydroxy-(2-4C)alkylamino and (1-4C)alkylsulphonamido, or $Ar^2$ is 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene which may optionally bear one or two substituents selected from halogeno, hydroxy, amino, cyano, (1-6C)alkyl, (1-6C)alkoxy, (1-6C)alkylamino and di-[(1-4C)alkyl]amino;

wherein $R^1$ is (1-6C)alkyl, (2-6C)alkenyl, (2-6C)alkynyl, fluoro-(1-4C)alkyl, cyano-(1-4C)alkyl, hydroxy-(1-4C)alkyl, (1-4C)alkoxy-(1-4C)alkyl and (2-4C)alkanoyloxy-(1-4C)alkyl;

wherein $R^2$ is hydrogen, (1-6C)alkyl, (3-6C)alkenyl, (3-6C)alkynyl, fluoro-(1-4C)alkyl, (1-4C)alkylthio-(1-4C)alkyl, cyano-(1-4C)alkyl, (1-4C)alkoxycarbonyl-(1-4C)alkyl, carboxy-(1-4C)alkyl, carbamoyl-(1-4C)alkyl or (2-6C)alkanoyl or $R^2$ is benzoyl which may optionally bear a substituent selected from halogeno, (1-6C)alkyl or (1-6C)alkoxy; and wherein Q is thiazolyl which may optionally bear one or two substituents selected from halogeno, amino, nitro, cyano, (1-6C)alkyl, (1-6C)alkoxy, (1-6C)alkylamino, di-[(1-4C)alkyl]amino, (1-4C)alkoxycarbonyl, (2-6C)alkanoyl, (2-6C)alkanoylamino, (1-4C)alkoxycarbonylamino, fluoro-(1-4C)alkyl and hydroxy-(1-4C)alkyl;

or a pharmaceutically-acceptable salt thereof.

2. A method as claimed in claim 1 involving a thiazole of the formula I wherein $Ar^1$ is phenyl, naphth-1-yl or naphth-2-yl which may optionally bear one, two or three substituents selected from fluoro, chloro, amino, hydroxy, cyano, formyl, carbamoyl, methyl, methoxy, -3-methylthio, methylsulphinyl, methylsulphonyl, methoxycarbonyl, acetamido, difluoromethyl and trifluoromethyl;

A is a direct link to X, or is methylene, 1-propenylene, 2-methylprop-1-enylene or 1-propynylene;

X is oxy, thio, sulphinyl or sulphonyl;

Ar² is 1,3-phenylene or 1,4-phenylene which may optionally bear one substituent selected from fluoro, hydroxy, amino, nitro, cyano, carbamoyl, methyl, methoxy, allyloxy, methylamino, dimethylamino, tert-butoxycarbonyl, acetamido, cyanomethoxy, carbamoylmethoxy, ethoxycarbonylmethoxy, trifluoromethyl, carbanoylmethylamino, cyanomethylamino, 2-hydroxyethlamino and methanesulphonamido, or Ar² is 2,4-, 2,5- or 3,5-pyridylene, or 4,6-pyrimidinylene;

R¹ is methyl, ethyl, propyl, vinyl, ethynyl, 2-propynyl, trifluoromethyl, cyanomethyl, hydroxymethyl, methoxymethyl or acetoxymethyl;

R² is methyl, ethyl, allyl, 2-propynyl, 2-fluoroethyl, 2,2-difluoroethyl, methylthiomethyl or cyanomethyl; and Q is 2-, 4- or 5-thiazolyl which may optionally bear one substituent selected from chloro, methyl and methoxycarbonyl;

or a pharmaceutically-acceptable salt thereof.

3. A method as claimed in claim 1 involving a thiazole of the formula I wherein

Ar¹ is phenyl, naphth-2-yl, 3,4-dichlorophenyl, 3-iodophenyl, 3-cyanophenyl, 3,4-dimethoxyphenyl, 3,4,5-trimethoxyphenyl, 4-methylthiophenyl, 4-methylsulphinylphenyl, 3-trifluoromethylphenyl, 6-fluoronaphth-2-yl or 5-cyanonaphth-2-yl;

A is methylene, 1-propenylene, 2-methylprop-1-enylene or 1-propynylene;

X is oxy;

Ar² is 1,3-phenylene, 5-hydroxy-1,3-phenylene, 5-amino-1,3-phenylene, 5-nitro-1,3-phenylene, 4-methyl-1,3-phenylene, 5methoxy-1,3-phenylene, 5-cyanomethoxy-1,3-phenylene, 5-carbamoylmethoxy-1,3-phenylene, 2,5-pyridylene, 3,5-pyridylene, 2,6-pyridylene or 4,6-pyrimidinylene;

R¹ is methyl, ethyl, propyl, vinyl, trifluoromethyl, hydroxymethyl, methoxymethyl or acetoxymethyl;

R² is hydrogen or methyl; and

Q is 2-thiazolyl or 4-thiazolyl;

or a pharmaceutically-acceptable salt thereof.

4. A method as claimed in claim 1 involving a thiazole of the formula I wherein

Ar¹ is phenyl, naphth-1-yl, naphth-2-yl, 2-fluorophenyl, 3-fluorophenyl, 4-fluorophenyl, 3,4-difluorophenyl, 6-fluoronaphth-2-yl, 7-fluoronaphth-2-yl, 2-chlorophenyl, 3-chlorophenyl, 2-tolyl, 6-methylnaphth-2-yl, 2-methoxyphenyl, 3-methoxyphenyl, 4-methoxyphenyl, 2-methylthiophenyl, 3-methoxycarbonylphenyl, 2-trifluoromethylphenyl, 3-trifluoromethylphenyl or 7-difluoromethylnaphth-2-2-yl;

A is a direct link to X, or is methylene, 1-propenylene or 1-propynylene;

X is oxy or thio;

Ar² is 1,3-phenylene, 5-fluoro-1,3-phenylene, 5-methoxy-1,3-phenylene, 2-methoxy-1,4-phenylene, 5-cyanomethoxy-1,3-phenylene, 5-trifluoromethyl-1,3-phenylene or 3,5-pyridylene;

R¹ is methyl or ethyl;

R² is methyl, ethyl, allyl, 2-propynyl or cyanomethyl; and

Q is 2-thiazolyl;

or a pharmaceutically-acceptable salt thereof.

5. A method as claimed in claim 1 involving a thiazole of the formula I wherein

Ar¹ is phenyl, naphth-1-yl, 2-fluorophenyl, 3-fluorophenyl, 4-fluorophenyl, 3,4-difluorophenyl, 2-chlorophenyl, 3-chlorophenyl, 2-tolyl, 2-methoxyphenyl, 3-methoxyphenyl, 4-methoxyphenyl, 3-methoxycarbonylphenyl, 2-trifluoromethylphenyl or 3-trifluoromethylphenyl;

A is 1-propynylene;

X is oxy;

Ar² is 1,3-phenylene, 5-fluoro-1,3-phenylene, 5-methoxy-1,3-phenylene, 2-methoxy-1,4-phenylene or 5-trifluoromethyl-1,3-phenylene;

R¹ is methyl or ethyl; R² is methyl; and

Q is 2-thiazolyl;

or a pharmaceutically-acceptable salt thereof.

* * * * *